(12) United States Patent
Yao et al.

(10) Patent No.: US 7,687,665 B2
(45) Date of Patent: Mar. 30, 2010

(54) 2-METHYLPROP ANAMIDES AND THEIR USE AS PHARMACEUTICALS

(75) Inventors: Wenqing Yao, Kennett Square, PA (US); Colin Zhang, Ambler, PA (US); Jincong Zhuo, Boothwyn, PA (US); Meizhong Xu, Hockessin, DE (US); Konstantinos Agrios, Exton, PA (US); Brian Metcalf, Moraga, CA (US)

(73) Assignee: Incyte Corporation, Wilmington, DE (US)

( * ) Notice: Subject to any disclaimer, the term of this patent is extended or adjusted under 35 U.S.C. 154(b) by 905 days.

(21) Appl. No.: 11/159,865

(22) Filed: Jun. 23, 2005

(65) Prior Publication Data

US 2005/0288329 A1 Dec. 29, 2005

Related U.S. Application Data

(60) Provisional application No. 60/582,477, filed on Jun. 24, 2004.

(51) Int. Cl.
C07C 233/05 (2006.01)
A61K 31/165 (2006.01)

(52) U.S. Cl. ............... 564/162; 564/182; 514/617; 514/618

(58) Field of Classification Search ........... 564/162, 564/182; 514/617, 618
See application file for complete search history.

(56) References Cited

U.S. PATENT DOCUMENTS

| | | | |
|---|---|---|---|
| 3,097,209 A | 7/1963 | Janssen et al. | |
| 3,328,156 A | 6/1967 | Hopkins | |
| 3,666,860 A | 5/1972 | Berkelhammer | |
| 3,770,748 A | 11/1973 | Borck et al | |
| 3,849,403 A | 11/1974 | Yardley et al. | |
| 3,933,829 A | 1/1976 | Archibald et al. | |
| 4,001,422 A | 1/1977 | Danilewicz et al. | |
| 4,013,445 A | 3/1977 | Bellus et al. | |
| 4,076,819 A | 2/1978 | Maffrand | |
| 4,145,435 A * | 3/1979 | Szmuszkovicz | 514/429 |
| 4,439,606 A | 3/1984 | Du et al. | |
| 5,076,961 A | 12/1991 | Nakamura et al. | |
| 5,244,894 A | 9/1993 | George et al. | |
| 5,292,745 A | 3/1994 | Heaulme | |
| 5,442,064 A | 8/1995 | Pieper et al. | |
| 5,614,534 A | 3/1997 | Binet et al. | |
| 5,633,247 A | 5/1997 | Baldwin et al. | |
| 5,668,138 A | 9/1997 | Baziard-Mouysset et al. | |
| 5,693,567 A | 12/1997 | Weisfield et al. | |
| 5,817,678 A | 10/1998 | Kim et al. | |
| 5,852,029 A | 12/1998 | Fisher et al. | |
| 5,981,754 A | 11/1999 | Badone et al. | |
| 6,547,958 B1 | 4/2003 | Elomari | |
| 7,074,788 B2 | 7/2006 | Kurz et al. | |
| 7,119,091 B2 | 10/2006 | Habashita et al. | |
| 7,122,532 B2 | 10/2006 | Walker et al. | |
| 2003/0203922 A1 | 10/2003 | Patel et al. | |
| 2003/0229119 A1 | 12/2003 | Kym et al. | |
| 2003/0236286 A1 | 12/2003 | Deorazio et al. | |
| 2004/0072802 A1 | 4/2004 | Duan et al. | |
| 2004/0188324 A1 | 9/2004 | Elomari | |
| 2005/0020645 A1 | 1/2005 | Ohta et al. | |
| 2005/0080078 A1 | 4/2005 | Aquila et al. | |
| 2005/0282858 A1 | 12/2005 | Yao et al. | |
| 2005/0288317 A1 | 12/2005 | Yao et al. | |
| 2005/0288329 A1 | 12/2005 | Yao et al. | |
| 2005/0288338 A1 | 12/2005 | Yao et al. | |
| 2006/0004049 A1 | 1/2006 | Yao et al. | |
| 2006/0009471 A1 | 1/2006 | Yao et al. | |
| 2006/0009491 A1 | 1/2006 | Yao et al. | |
| 2006/0019977 A1 | 1/2006 | Habashita et al. | |
| 2006/0106045 A1 | 5/2006 | Hughes et al. | |
| 2006/0116382 A1 | 6/2006 | Yao et al. | |
| 2006/0122197 A1 | 6/2006 | Yao et al. | |
| 2006/0122210 A1 | 6/2006 | Yao et al. | |
| 2006/0149070 A1 | 7/2006 | Rohde et al. | |
| 2006/0199816 A1 | 9/2006 | Gillespie et al. | |
| 2007/0066584 A1 | 3/2007 | Yao et al. | |
| 2007/0129345 A1 | 6/2007 | Zhuo et al. | |
| 2007/0179142 A1 | 8/2007 | Yao et al. | |
| 2007/0197506 A1 | 8/2007 | Yao et al. | |
| 2007/0197530 A1 | 8/2007 | Li et al. | |
| 2007/0208001 A1 | 9/2007 | Zhuo et al. | |
| 2007/0213311 A1 | 9/2007 | Li et al. | |

(Continued)

FOREIGN PATENT DOCUMENTS

DE     2623567     12/1976

(Continued)

OTHER PUBLICATIONS

Coutts et al, J. Chem. Soc. Perk. Trans. I, 1990, (3), 767-771.*

(Continued)

*Primary Examiner*—Shailendra Kumar
(74) *Attorney, Agent, or Firm*—Fish & Richardson P.C.

(57) ABSTRACT

The present invention relates to inhibitors of 11-β hydroxyl steroid dehydrogenase type 1, antagonists of the mineralocorticoid receptor (MR), and pharmaceutical compositions thereof. The compounds of the invention can be useful in the treatment of various diseases associated with expression or activity of 11-β hydroxyl steroid dehydrogenase type 1 and/or diseases associated with aldosterone excess.

28 Claims, No Drawings

U.S. PATENT DOCUMENTS

| | | |
|---|---|---|
| 2007/0270424 A1 | 11/2007 | Li et al. |
| 2007/0275990 A1 | 11/2007 | Ohmoto et al. |
| 2007/0293529 A1 | 12/2007 | Li et al. |
| 2008/0255154 A1 | 10/2008 | Yao et al. |
| 2008/0318991 A1 | 12/2008 | Yao et al. |

FOREIGN PATENT DOCUMENTS

| | | |
|---|---|---|
| DE | 136963 | 8/1979 |
| EP | 0 141 419 | 5/1985 |
| EP | 0 273 659 | 7/1988 |
| EP | 0 404 039 | 12/1990 |
| EP | 0 498 718 | 8/1992 |
| EP | 0 520 883 | 12/1992 |
| EP | 0 743 312 | 11/1996 |
| EP | 0 921 125 | 6/1999 |
| EP | 1683797 | 7/2006 |
| ES | 427 013 A1 | 7/1976 |
| FR | 1 600 908 | 8/1970 |
| FR | 2289498 | 5/1976 |
| JP | 60149562 | 8/1985 |
| JP | 04-334357 | 11/1992 |
| RU | 2002117652 | 1/2004 |
| WO | WO 9711940 | 4/1997 |
| WO | WO 9741102 | 11/1997 |
| WO | WO 9964004 | 12/1999 |
| WO | WO 0001702 | 1/2000 |
| WO | WO 0023076 | 4/2000 |
| WO | WO 0059874 | 10/2000 |
| WO | WO 0105790 | 1/2001 |
| WO | WO 0130780 | 5/2001 |
| WO | WO 0170673 | 9/2001 |
| WO | WO 0204425 | 1/2002 |
| WO | WO 0204465 | 1/2002 |
| WO | WO 0206868 | 1/2002 |
| WO | WO 0222572 | 3/2002 |
| WO | WO 0246156 | 6/2002 |
| WO | WO 02058690 | 8/2002 |
| WO | WO 02069973 | 9/2002 |
| WO | WO 02078641 | 10/2002 |
| WO | WO 02092585 | 11/2002 |
| WO | WO 03010138 | 2/2003 |
| WO | WO 03022809 | 3/2003 |
| WO | WO 03037271 | 5/2003 |
| WO | WO 03037847 | 5/2003 |
| WO | WO 03041641 | 5/2003 |
| WO | WO 03045912 | 6/2003 |
| WO | WO 03049736 | 6/2003 |
| WO | WO 03051840 | 6/2003 |
| WO | WO 03053915 | 7/2003 |
| WO | WO 03057698 | 7/2003 |
| WO | WO 03065983 | 8/2003 |
| WO | WO 03072197 | 9/2003 |
| WO | WO 03077847 | 9/2003 |
| WO | WO 03099821 | 12/2003 |
| WO | WO 03104207 | 12/2003 |
| WO | WO 03104233 | 12/2003 |
| WO | WO 2004000789 | 12/2003 |
| WO | WO 2004005295 | 1/2004 |
| WO | WO 2004/017961 | 3/2004 |
| WO | WO 2004/018479 | 3/2004 |
| WO | WO 2004/022554 | 3/2004 |
| WO | WO 2004033427 | 4/2004 |
| WO | WO 2004033440 | 4/2004 |
| WO | WO 2004/058727 | 7/2004 |
| WO | WO 2004056745 | 7/2004 |
| WO | WO 2004056789 | 7/2004 |
| WO | WO 2004058253 | 7/2004 |
| WO | WO 2004058715 | 7/2004 |
| WO | WO 2004058727 | 7/2004 |
| WO | WO 2004065351 | 8/2004 |
| WO | WO 2004/082687 | 9/2004 |
| WO | WO 2004072197 | 9/2004 |
| WO | WO 2004076418 | 9/2004 |
| WO | WO 2004089470 | 10/2004 |
| WO | WO 2004089896 | 10/2004 |
| WO | WO 2004096139 | 11/2004 |
| WO | WO 2004098589 | 11/2004 |
| WO | WO 2004/103995 | 12/2004 |
| WO | WO 2004106294 | 12/2004 |
| WO | WO 2005032472 | 4/2005 |
| WO | WO 2005037814 | 4/2005 |
| WO | WO 2005044192 | 5/2005 |
| WO | WO 2005044797 | 5/2005 |
| WO | WO 2005047286 | 5/2005 |
| WO | WO 2005058890 | 6/2005 |
| WO | WO 2005060963 | 7/2005 |
| WO | WO 2005061499 | 7/2005 |
| WO | WO 2005063745 | 7/2005 |
| WO | WO 2005068460 | 7/2005 |
| WO | WO 2005070407 | 8/2005 |
| WO | WO 2005084667 | 9/2005 |
| WO | WO 2005095350 | 10/2005 |
| WO | WO 2005108359 | 11/2005 |
| WO | WO 2005110992 | 11/2005 |
| WO | WO 2006002349 | 1/2006 |
| WO | WO 2006002350 | 1/2006 |
| WO | WO 2006002361 | 1/2006 |
| WO | WO 2006/020598 | 2/2006 |
| WO | WO 2006012173 | 2/2006 |
| WO | WO 2006012226 | 2/2006 |
| WO | WO 2006012227 | 2/2006 |
| WO | WO 2006/047176 | 5/2006 |
| WO | WO 2006/047196 | 5/2006 |
| WO | WO 2006053024 | 5/2006 |
| WO | WO 2006053120 | 5/2006 |
| WO | WO 2006055752 | 5/2006 |
| WO | WO 2006080533 | 8/2006 |
| WO | WO 2006094633 | 9/2006 |
| WO | WO 2006130986 | 12/2006 |
| WO | WO 2006138512 | 12/2006 |
| WO | WO 2007038138 | 4/2007 |
| WO | WO 2007051810 | 5/2007 |
| WO | WO 2007067504 | 6/2007 |
| WO | WO 2007084314 | 7/2007 |
| WO | WO 2007089683 | 8/2007 |
| WO | WO 2007101270 | 9/2007 |
| WO | WO 2007103719 | 9/2007 |

OTHER PUBLICATIONS

Database CAPLUS on STN (Columbus, OH, USA) No. 126:317635, "Alpha-amino acids derived from ornithine as building blocks for peptide synthesis" abstract, Gescrinier et al. j. Pep. Res. ' 49(2):183-189 (1997).

Database CAPLUS on STN (Columbus, OH, USA) No. 143:78479, "Preparation of amino acid derivatives as novel M3 muscarinic acetylcholine receptor antagonists" abstract, Busch et al. (2005), see RN 902149-23-9 and 854750-92-8.

International Search Report for PCT/US05/28201.

Gu et al., "Discovery of 4-heteroarylbicyclo[2.2.2]octyltriazoles as potent and selective inhibitors of 11β-HSD1: Novel therapeutic agents for the treatment of metabolic syndrome," *Bioorg. Med. Chem. Lett.*, 15:5266-5269 (2005).

Yeh et al., "Discovery of orally active butyrolactam 11β-HSD1 inhibitors," *Bioorg. Med. Chem. Lett.*, 16:5555-5560 (2006).

Yeh et al., "Synthesis and biological evaluation of heterocycle containing adamantine 11β-HSD1 inhibitors," *Bioorg. Med. Chem. Lett.*, 16:5414-5419 (2006).

Buzas, A. et al., *Chimica Therapeutica, Eur. J. Med. Chem.*, 1972, 7(5), pp. 361-426.

Bursavich et al., *Org. Lett.*, 2001, 3, 2625.

Bydal et al. "Inhibition of type 2 17b-hydroxysteroid dehydrogenase by estradiol derivatives bearing a lactone on the D-ring: structure-activity relationships", Steroids, 2004, 69, 325-342.
Chem. Abs. 79:31890.
Chem. Abs. 82:156099.
Chem. Abs. 92:174158.
Chem. Abs. 118:254748.
Chem. Abs. 126:277320.
Chem. Abs. 129:148842.
Chem. Abs. 1985:78786.
Chem. Abs. 1987:598246.
Chem. Abs. 2006:768409.
Cheng et al., Eur. J. Med. Chem., 1991, 26(2), pp. 125-128.
Combs, et al., J. Comb. Chem. 2002, 4, 179.
Conroy, et al.,"Using the electrostatic field effect to design a new class of inhibitors for cysteine proteases", J. Am. Chem. Soc., 1997, vol. 119, pp. 4285-4291.
Coutts et al., "The conversion of phenols to primary and secondary aromatic amines via a Smiles rearrangement", Database CA [Online], Chemical Abstracts Service, Columbus, Ohio, US; Database Accession No. 1990:514704.
Cuiban., "Reductive cyclization .alpha.- and .beta.-(o-nitrophenyl)-substituted amides", Database CA [Online], Chemical Abstracts Service, Columbus, Ohio, US, Database Accession No. 1972:539925.
Dankwardt, et al., Tetrahedron Lett. 1995, 36, 4923.
Database CAPLUS on STN (Columbus, OH, USA) No. 108:131815, Preparation and testing of f7-amino-1,3-dihydro-2H-imidazo[4,5-b]quinolin-2-ones as phosphodiesterase and bloodplatelet aggregation inhibitors', abstract, Meanwell, et al. (1988) see RN 113288-90-7.
Database CAPLUS on STN (Columbus, OH, USA) No. 118:255342, {re[artopm pf M-heterpcuc;u;carbpmu;a,omp acids and analogs as prolylendopeptidase inhibotors' abstract, Hosoda et al. (1993) see RN 147635-61-8.
Hosoda et al., "Preparation of N-(heterocyclylcarbonyl)amino acids and analogs as prolyl endopeptidase inhibitors", Database CAPLUS on STN (Columbus, OH, USA) No. 118:255342, Abstract, (1993) see RN 147635-61-8.
Huber, "11βHSD1 Inhibitors for Type 2 Diabetes: A Systematic Development Strategy to Assess Pharmacodynamic Activity and Obtain Proof-of-Concept in Man," IBC's 5th Annual Targeting Metabolic Disorders Conference, Feb. 26-27, 2007.
Hughes, et al., "The Total Synthesis of (-)-Amathaspiramide F**," Angew. Chem. Int. Ed., 2002, 41(23) 4556-4559.
Irikura et at., "New antiulcer agents. I. Synthesis and biological activities of 1- acyl-2-, -3-, and -4-substituted benzamidopiperidines." J. Med. Chem. 1971, 14, pp. 357-361. (Chem. Abs. 92:174158).
Knochel et al. Angew. Chem. Int. Ed. 2003, 42, 4302 -4320.
Knoops et al., "Generation of 3-piperidine(methan)amines and cyclic 3-piperidinemethanamines as potential substance P antagonists", Tetrahedron, (1997), vol. 53, pp. 12699-12716.
"Known 2-iodomethylbenzoates", 168 pages.
Leonardi, A. et al., "Synthesis, Pharmacological Evaluation, and Structure—Activity Relationship and Qunatitative Structure—Activity Relationship Studies on Novel Derivatives of 2,4-Diamino-6,7-dimethoxyquinazoline alphal-Adrenoceptor Antagonists" J. Med. Chem. 42(3):427-437 (1999).
Lewis et al. J. Chem. Soc. Perkin Trans. 2, 1991, vol. 10. pp. 1625-1630.
Li et al. Syntheses and SAR of piperidin-3-yl ureas as potent and selective 11β-HSD-1 inhibitors, MEDI 54 Abstract of Presentation at the 233rd ACS National Meeting, Chicago, IL, Mar. 25-29, 2007.
Li et al. Syntheses and SAR of Piperidin-3-yl Ureas as Potent and Selective 11β-HSD-1 inhibitors, Presentation at the 233rd ACS National Meeting, Chicago, IL, Mar. 25-29, 2007.
Louie, et al., Tetrahedron Lett., 1995, 36, 3609.
Mallams, A.K. et al, "Inhibitors of Farnesyl Protein Transferase, 4-Amido, 4-Carbamoyl, and 4-Carboxamido Derivatives of 1-(8-Chloro-6,11-dihydro-5H-benzo[5,6]-cyclohepta[1,2-b]pyridin-11-yl)piperazine and 1-(3-Bromo-8-chloro-6,11-dihydro-5H-benzo[5,6]cyclohepta[1,2-b]pyridin-11-yl)piperazine" J. Med. Chem. 41(6):877-893 (1998).

Markees et al., J. Am. Chem. Soc., 1949, vol. 71, pp. 2031-2035.
Martin-Martinez et al., "Synthesis and stereochemical structure-activity relationships of 1,3-dioxoperhydropyrido[1,2-c]pyrimidine derivatives: Potent and selective cholecystokinin-A receptor antagonists", J. Med. Chem., 1997, vol. 40, pp. 3402-3407.
Martin, et al. "Do Structurally Similar Molecules Have Similar Biological Activity?", J. Med. Chem., 2002, 45, 4350-4358.
Matsumoto et al., "Direkte Aminolyse von nicht aktivierten Estern bei hohm Druck," Angew. Chem., 1996, 98, 569-570.
Meanwell, et al., "Preparation and testing of 7-amino-1,3-dihydro-2H-imidazo [4,5-b]quinolin-2-ones as phosphodiesterase and blood platelet aggregation inhibitors", Database CAPLUS on STN (Columbus, OH, USA) No. 108:131815, Abstract, (1988) see RN 113288-90-7.
Mehrotra et al., "Discovery of Novel 2,8-Diazaspiro[4,5]decanes as orally Active Glycoprotein IIb-IIIa Antagonist", J. Med. Chem., 2004, 47, pp. 2037-2061.
Messinger et al., "New inhibitors of 17b-hydroxysteroid dehydrogenasse type 1", Molecular and Cellular Endocrinology, 2006, 248, 192-198.
Mishani, et al. Tetrahedron Lett., 1996, 37, 319.
Miyabe et al., "The total synthesis of (-)-balanol", Synlett., 1997, pp. 580-582 (Chem. Abs. 130:38227).
Moeller, K.D. et al., "Anodic Amide Oxidations in the Presence of Electron-Rich Phenyl Rings: Evidence for an Intramolecular Electron-Transfer Mechanism" J. Org. Chem., 1991, vol. 56(3):1058-1067 (1991).
Morris, et al., "Amathaspiramides A-F, Novel Brominated Alkaloids from the Marine Bryozoan," J. Nat. Prod, 1999, 62, 688-693.
Morton et al. (2001) J. Biol. Chem. 276: 41293-41300.
Morton et al. (2004) Diabetes 53: 931-938.
Moya et al., "Synthesis and Biological Evaluation of New Analogies of the Active Fungal Metabolites N-(2-Methyl-3-oxodecanoyl)-2-pyrroline and N-(2-Methyl-3-oxodec-8-enoyl)-2-pyrroline," J. Agric. Food Chem., 1999, 47, 3866-3871.
Nojima, et al., Spiro Compounds Formation by the Reaction of Cycloalkene with Friedel-Crafts Catalyst. I. Reaction of Cyclohexene with Aluminum Chloride. The Rearrangement of Cyclohexylcyclohexene, J. Org. Chem., 1966, 31 (12), pp. 3966-3969.
Ogura, et al., "[1,4] Addition of (Methylthio p-Tolyl Sulfone to α,β-Unaturated Carbonyl Compounds", J. Org. Chem., 1986, 51, pp. 508-512.
Ohta et al., "Preparation of heterocyclyl moiety-containing diamine derivatives as factor Xa inhibitors"; Chem. Abs. 141:106461.
Olivier et al., "Binding to albumin of spin-labeled derivatives of clofibric acid", Database CA [Online], Chemical Abstracts Service, Columbus, Ohio, US; retrieved from STN Database Accession No. 1986:45271.
Pekala et al., "Synthesis of N-acyl derivatives of DL-trans-1,2-cyclohexanol", Database CA [Online], Chemical Abstracts Service, Columbus, Ohio, US; retrieved from STN, Database Accession No. 1995:459419.
Poirier et al. "Inhibitors of type II 17b-hydroxysteroid dehydrogenase" Molecular and Cellular Endocrinology 2001, 171, 119-128.
RN 147635-61-8 structure, abstract, and patent family details (3 pages).
RN 113288-90-7 structure, abstract, and patent family details (3 pages).
Sandeep et al., Proc. Natl. Acad. Sci. USA, 2004, 101, 6734-6739.
Schelsinger et al., "N-Substituted-Amides," J. Am. Chem. Soc., 1956, 78: 6123-6127.
Scott, F. L. et al., "Synthesis and Reactions of Trihalogeno-Diazabutadienes—New Versatile Synthetic Intermediates", Tetrahedron Letters, 47, pp. 4079-4082, 1970.
Shridhar et al., "Synthesis of new 3-methoxy-4-(acylamino)phenyl isothiocyanates and 4'-(isothiocyanatophenoxy)acetamides/ isobutyramides as possible anthelmintic agents", Retrieved from STN, Database Accession No. 1987:554038.
Suess, R. Helvetica Chimica Acta vol. 60(5), 1977-Nr.165.

Taylor et al., "On the ritter reaction of cyclic hydroxyamines: synthesis of conformationally-restricted reduced amide dipeptide isosteres", *Tetrahedron Letters*, (1996), vol. 37, pp. 1297-1300.
Wajchenberg (2000) Endocr. Rev. 21: 697-738.
von Geldern et al., *Biorg. Med. Chem. Lett.*, 2005, 15, 195.
Wheatley et al., "Basic Ethers Derived from β-Hydroxyphenethylamines," *J. Org. Chem.*, 1958, 23, 1360-1363.
Wojcik et al., "Catalytic Hydrogenation of Amides to Amines," *J. Am. Chem. Soc.*, 1934, 56, 2419-2424.
Wolff, "Burger's Medicinal Chemistry, 5ed, Part I", John Wiley & Sons, 1995, pp. 975-977.
Woolven et al. *J. Med. Chem.*, 2003, 46, 4428.
Xu et al., "Synthesis of Aza/Oxaspiro-y-lactams by Radical Translocation Cyclization Reastions," *Synlett*, 2005, 12, 1865-1868.
Yao, et al. Discovery of potent and selective 11β-HSD-1 Inhibitors, MEDI 228 Abstract of Presentation at the 233rd ACS National Meeting, Chicago, IL, Mar. 25-29, 2007.
Yao, Discovery of Potent and Orally Active Inhibitors of 11β-Hydroxysteroid Dehydrogenase I, presentation at the 233rd ACS National Meeting, Chicago, IL, Mar. 27, 2007.
Yao et al., "Preparation of cycloalkylearbonylammes and heteroeyeloalkylcarbonylammes as 11β hydroxysteroid dchydrogenase type I inhibitors and mineraloeorticoid receptor antagonist and their use as pharmaceutical", Caplus English Abstract DN 144.6815, Nov. 2005.
Yokoyama et al., "The First Effective Syntheses of Cyanoflurormethylated Amides, Thioamides, and Phosphorus Compunds Using 2-Cyano-2-fluoro-2-phenylacetonitrile and $ET_3GeNa$," *Synthesis*, 8: 1319-1324 (1999).
Zhuo. et al. Discovery and synthesis of nipecotic amide as novel, potent and selective 11β-HSD-1- inhibitors MEDI 48 Abstract, 233rd ACS National Meeting, Chicago, IL, Mar. 25-29, 2007.
Zhuo et al. Discovery of Nipecotic Amides as Novel, Potent and Selective 11βHSD1 Inhibitors, poster at the 233rd ACS National Meeting, Chicago, IL, Mar. 25-29, 2007.
Amendment and Response in Reply to Office Action of Mar. 29, 2007 submitted Jun. 28, 2007 in connection with U.S. Appl. No. 11/281,648 (US20060122210A1).
Amendment in Reply to Action of Jul. 31, 2007 submitted Oct. 30, 2007 in connection with U.S. Appl. No. 11/281,648 (US20060122210A1).
Ex Parte Quayle Action—U.S. Appl. No. 11/122,309 (US20050282858) dated Dec. 14, 2006.
Final Office Action U.S. Appl. No. 11/281,648 (US20060122210A1) dated Dec. 13, 2007.
Interview Summary U.S. Appl. No. 11/784,450 dated Jul. 14, 2008.
Int'l Preliminary Report on Patentability—Int'l App. No. PCT/US05/15559 (WO2005/110992) dated Nov. 7, 2006.
Int'l Preliminary Report on—Int. App. No. PCT/US05/041763 (WO/2006/055752).
Int'l Preliminary Report on Patentability—Int'l App. No. PCT/US05/22170 (WO2006/012173) dated Jan. 11, 2007.
Int'l Preliminary Report on Patentability—Int'l App. No. PCT/US05/22307 (WO2006/012226) dated Dec. 28, 2006.
Int'l Preliminary Report on Patentability—Int'l App. No. PCT/Us05/22411 (WO/2006/002349) dated Dec. 28, 2006.
Int'l Preliminary Report on Patentability—Int'l App. No. PCT/US05/22412 (WO2006/002350) dated Dec. 28, 2006.
Int'l Preliminary Report on Patentability—Int'l App. No. PCT/US05/022434 (WO2006/002361) dated Dec. 28, 2006.
Int'l Preliminary Report on Patentability—Int'l App. No. PCT/US05/028201 (WO2006/020598) dated Feb. 13, 2007.
Int'l Preliminary Report on Patentability—Int'l App. No. PCT/US05/040550 (WO2006/053024 dated May 30, 2007.
Int'l Preliminary Report on Patentability—Int'l App. No. PCT/US06/036652 WO2007/038138 dated Mar. 28, 2008.
Int'l Preliminary Report on Patentability—Int'l App. No. PCT/US06/46309 (WO2007/067504) dated Jun. 11, 2008.
Alberts et al. Endocrinology (2003) 144: 4755-4762.
Albiston et al. (1994) Mol. Cell. Endocrin. 105: R11-R17.
Barf et al. (2002) J. Med. Chem. 45: 3813-3815.
Bellows et al. (1998) Bone 23: 119-125.
Bhargava et al., (2001), Endo 142: 1587-1594.

Billaudel and Sutter (1979) Horm. Metab. Res. 11: 555-560.
Bioreversible Carriers in Drug Design, ed. Edward B. Roche, American Pharmaceutical Association and Pergamon Press, 1987.
Blum, et al., (2003) Prog. Nucl, Acid Res. Mol. Biol. 75:173-216.
Bujalska et al. (1997) Lancet 349: 1210-1213.
Canalis (1996) J. Clin. Endocrinol. Metab. 81: 3441-3447.
Conn, (1955), J. Lab. Clin. Med. 45: 6-17.
Cooper et al. (2000) Bone 27: 375-381.
Davani et al. (2000) J. Biol. Chem. 275: 34841-34844.
Draper et al. (2003) Nat. Genet. 34: 434-439.
Edwards et al. (1988) Lancet 2: 986-989.
Engeli, et al., (2004) Obes. Res. 12: 9-17.
Funder et al. (1988), Science 242: 583-585.
Greene, et al., Protective Groups in Organic Synthesis, 2d. Ed., Wiley & Sons, 1991.
Jausons-Loffreda et al. J. Biolumin and Chemilumin, 9:217-221 (1994).
Journal of Pharmaceutical Science, 66, 2 (1977).
Kotelevstev et al. (1997) Proc. Natl. Acad. Sci. 94: 14924-14929.
Kurulculasuriya , et al., (2003) Curr. Med. Chem. 10: 123-53.
Lindsay et al. (2003) J. Clin. Endocrinol. Metab. 88: 2738-2744.
Livingstone et al. (2000) Endocrinology 131: 560-563.
Low et al. (1994) J. Mol. Endocrin. 13: 167-174.
Lupien et al. (1998) Nat. Neurosci. 1: 69-73.
Masuzaki et al. (2001) Science 294: 2166-2170.
Masuzaki et al. (2003) J. Clinical Invest. 112: 83-90.
Masuzaki, et al., (2003) Curr. Drug Targets Immune Endocr. Metabol. Disord. 3: 255-62.
Matsuzawa et al. (1999) Ann. N. Y. Acad. Sci. 892: 146-154.
McEwen and Sapolsky (1995) Curr. Opin. Neurobiol. 5: 205-216.
Miller and Chrousos (2001) Endocrinology and Metabolism, eds. Felig and Frohman (McGraw-Hill, New York), 4th Ed.: 387-524.
Ogawa et al. (1992) J. Clin. Invest. 90: 497-504.
Pitt et al., New England J. Med. (1999), 341: 709-719.
Pitt et al., New England J. Med. (2003), 348: 1309-1321.
Rajan et al. (1996) J. Neurosci. 16: 65-70.
Rask et al. (2001) J. Clin. Endocrinol. Metab. 86: 1418-1421.
Rauz et al. (2001) Invest. Ophthalmol. Vis. Sci. 42: 2037-2042.
Reaven (1993) Ann. Rev. Med. 44: 121-131.
Remington's Pharmaceutical Sciences, 17th ed., Mack Publishing Company, Easton, Pa., 1985, p. 1418.
Stokes et al. (2000) Invest. Ophthalmol. Vis. Sci. 41: 1629-1683.
T. Higuchi and V. Stella, "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press, 1987.
Wake et al. (2003) J. Clin. Endocrinol. Metab. 88: 3983-3988.
Walker et al. (1979) Hypertension 1: 287-291.
Wilson et al. (1998) Proc. Natl. Acad. Sci. 95: 10200-10205.
Yau et al. (2001) Proc. Natl. Acad. Sci. 98: 4716-4721.
Coutts, I.G.C. et al., *J. Chem. Soc. Perk. Trans.*, 1(3), pp. 767-771, 1990.
Database CAPLUS on STN (Columbus, OH, USA) No. 2004:802077, "Zeolite SSZ-65 synthesis, properties, and use as petroleum and hydrocarbon refining catalysts", abstract, XP002514477.
Database CAPLUS on STN (Columbus, OH, USA) No. 1983: 107002, "1-(4-chlorophenyl)-1-cyclopentanecarboxylic acid derivatives", abstract, XP002514476.
Dorwald, F.A. Side Reactions in Organic Synthesis, Wiley-VCH, Weinheirn, p. IX of Preface, pp. 1-16, and pp. 40-41.
Huber, R. "11βHSD1 Inhibition as an Entrée to Cardio-Metabolic Benefit in Type 2 Diabetes," presentation at Discovery on Target: Targeting Diabetes with Novel Therapeutics. Boston, MA, Oct. 22, 2008.
Huber, R. "INCB013739, a Selective Inhibitor of 11b-Hydroxysteroid Dehydrogenase Type 1 (11βHSD1), Improves Insulin Sensitivity and Lowers Plasma Cholesterol Over 28 Days in Patients with Type 2 Diabetes Mellitus." American Diabetes Association 68th Scientific Sessions, San Francisco, CA Jun. 9, 2008.
Huber, R. "Incyte 11βHSD1 Inhibitor Program in Type 2, Diabetes Mellitus." 2008 Therapeutic Area Partnerships Conference. Philadelphia, PA Nov. 4, 2008.

Huber, R. "Proof-of-Concept for 11beta-HSD1 Inhibition in Man: Evidence for Metabolic Improvements in Type 2 Diabetic Subjects after Short-Term INCB013739 Therapy." Presentation at Targeting Metabolic Disorders, Chapel Hill, NC Mar. 18, 2008.
International Search Report and Written Opinion for PCT/US05/41763, dated Apr. 24, 2007.
International Search Report for PCT/US2007/069033, dated Apr. 28, 2008.
International Search Report for PCT/US2007/063050, dated Jul. 9, 2007.
International Search Report for PCT/US2007/067753, dated Oct. 2, 2007.
International Search Report for PCT/US2006/046309, dated Sep. 7, 2007.
International Search Report for PCT/US05/22170, dated Nov. 17, 2005.
International Search Report for PCT/US05/22307, dated Apr. 25, 2006.
International Search Report for PCT/US05/22411, dated Oct. 20, 2005.
International Search Report for PCT/US05/22434, dated Mar. 31, 2005.
International Search Report for PCT/US05/40550, dated May 11, 2007.
International Search Report for PCT/US2006/036652, dated Apr. 2, 2007.
International Search Report for PCT/US20061046306, dated Jan. 28, 2008.
International Search Report for PCT/US20071000695, dated Jan. 31, 2008.
International Search Report for PCT/US2007/002360, dated Jun. 19, 2007.
"Known 2-iodomethylbenzoates", 168 pages. Results of a Chemical Abstracts Search Examiner David O'Dell and cited in an Office Action dated Jul. 31, 2007 for U.S. Appl. No. 11/281,648. (2007).
Supplementary Partial European Search Report dated Feb. 11, 2009 in connection with EP App. No. 05745656.8.
Li, Y. et al. Syntheses and SAR of piperidin-3-yl ureas as potent and selective 11β-HSD-1 inhibitors, MEDI 54 Abstract of Presentation at the 234$^{th}$ ACS National Meeting, Boston, MA Aug. 19-23, 2007.
Li, Y. et al Syntheses and SAR of Piperidin-3-yl Ureas as Potent and Selective 11β-HSD-1 inhibitors, Presentation at the 234$^{th}$ ACS National Meeting, Boston, MA Aug. 19-23, 2007.
Manthorpe, J.M. et al., Angew. Chem. Int., vol. 41, No. 13, pp. 2338-2341, 2002.
Written Opinion of the International Searching Authority mailed Apr. 24, 2007 in connection with Int. App. No. PCT/US05/41763.
Zhuo, J. et al. Discovery and synthesis of nipecotic amide as novel, potent and selective 11β-HSD-1-inhibitors MEDI 48 Abstract, 234$^{th}$ ACS National Meeting, Boston, MA Aug. 19-23, 2007.
Zhuo, J. et al. Discovery of Nipecotic Amides as Novel, Potent and Selective 11βHDS1 Inhibitors, poster at the 234$^{th}$ ACS National Meeting, Boston, MA Aug. 19-23, 2007.
Ammar et al., "Synthesis of 7,7-dimethylaporphine alkaloids", Database CA [Online], Chemical Abstracts Service, Ohio, US; retrieved from STN Database Accession No. 1983:198499.
Atwell et al., "Relationships between structure and kinetics of cyclization of 2-aminoaryl amides: potential prodrugs of cyclization-activated aromatic mustards", Database CA [Online], Chemical Abstracts Service, Ohio, US; retrieved from STN Database Accession No. 1994:216381.
Banker, G.S. et al., "Modern Pharmaceutics, 3ed.", Marcel Dekker, New York, 1996, pp. 451 and 596.
Ben et al., "Synthesis of Opticaly Active α-Amino Esters via Dynamic Kinetic Resolution: A Mechanistic Study," J. Org. Chem. 64: 7700-7706 (1999).
Binet et al., "Structure Activity Relationships of New Inhibitors of Mammalian 2,3-oxklosqualene Cyclase," Chem. Pharm. Bull., 2002, 50(3), 316-329.
Bolm, C. et al. J. Org. Chem. 2005, 70, 2346.
Borthwick, A.D. et al., J. Med. Chem., 2003, 46, 4428.
Buzas, A. et al., Chimica Therapeutica, Eur. J. Med. Chem., 1972, 7(5), pp. 361-426.

Bydal et al. "Inhibition of type 2 17b-hydroxysteroid dehydrogenase by estradiol derivatives bearing a lactone on the D-ring: structure-activity relationships", Steroids, 2004, 69, 325-342.
Chem. Abs. 79:31890, 1973.
Chem. Abs. 82:156099, 1974.
Chem. Abs. 92:174158, 1979.
Chem. Abs. 118:254748, 1992.
Chem. Abs. 126:277320, 1997.
Chem. Abs. 129:148842, 1998.
Cheng et al., Eur. J. Med. Chem., 1991, 26(2), pp. 125-128.
Conroy, et al., "Using the electrostatic field effect to design a new class of inhibitors for cysteine proteases", J. Am. Chem. Soc., 1997, vol. 119, pp. 4285-4291.
Coutts et al., "The conversion of phenols to primary and secondary aromatic amines via a Smiles rearrangement", Database CA [Online], Chemical Abstracts Service, Columbus, Ohio, US; Database Accession No. 1990:514704.
Cuiban., "Reductive cyclization .alpha.- and .beta.-(o-nitrophenyl)-substituted amides", Database CA [Online], Chemical Abstracts Service, Columbus, Ohio, US, Database Accession No. 1972:539925.
Database CAPLUS on STN (Columbus, OH, USA) No, 108:131815, Preparation and testing of f7-amino-1,3-dihydro-2H-imidazo[4,5-b]quinolin-2-ones as phosphodiesterase and bloodplatelet aggregation inhibitors' abstract, Meanwell, et al. (1988) see RN 113288-90-7.
Database CAPLUS on STN (Columbus, OH, USA) No. 118:255342, {re[artopm pf M-heterpcuc;u;carbpmu;a,omp acids and analogs as prolylendopeptidase inhibotors' abstract, Hosoda et al. (1993) see RN 147635-61-8.
Database CAPLUS, on STN (Columbus, OH, USA), 1987:598246, No.107:198246, "Pyperazine derivatives. XVII. Synthesis and Tuberculostatic Activity of Pyrazinyl-1, 3, 4-oxadiazole Derivatives", abstract, Pancechowska-Ksepko et al., 1986, see RN 10953 8-74-1, XP-002464725.
Database CAPLUS, on STN (Columbus, OH, USA) 1985:78786, No. 102:78786, 102:12353a,12356a, "Some Reactions of 5-(3- or 4-pyridyl) -1,3, 4-oxidiazoles with Amines and Hydrazines", abstract, Zayed, S.A. et al., et al., 1984, see RN 94696-15-8, 94696-16-91. XP-002464726.
Database CAPLUS, on STN (Columbus, OH, USA) 2006:768409, No. 145:211047, "Preparation of 3-amino-1,2,4-triazole derivatives as 11.beta.-hydroxysteroid dehydrogenase type 1 inhibitors", abstract, Manabu, I. et al, see RN 904321-63-7, 904321- 80-8, 904321-81-9. XP-002464555.
Database CAPLUS on STN (Columbus, OH, USA) No. 143:7612, "Preparation of Heterocyclic Spiro Compounds for Treatment of Stress Related Diseases", RN 64097-78-5, (2005).
Database CAPLUS on STN (Columbus, OH, USA) No. 135:257227, "Preparation of pyrrolidinone derivatives having .sigma.-receptor affinity", RN-362518-14-7, RN 362518- 16-9, RN 362518-15-8, RN 363518-17-0; (2001).
Database CAPLUS on STN (Columbus, OH, USA) No. 55:87498, "Synthetic drugs. VI. A new type of spirosuccinimade", RN-64097-71-8; RN-102654-82-0; RN- 113251-47-1, RN-113687-61-9, RN-114509-25-0; (1961).
Database CAPLUS ACS on STN, 2006, CAPLUS English Abstract US 2005288317, Dec. 29, 2005, see: RN 872412-08-3 structure, abstract, and patent family details (2 pages).
Database CAPLUS ACS on STN, 2006, DN 144:6815,See RN869970-58-1, 2005 sstructure, abstract, and patent family (1 pages).
Database CA (Online) Chemical Abstracts Service, Columbus, Ohio, US; "Amides of 2-(p-chlorophenoxy)-2- acid" retrieved from STN Database accession No. 1977:72243.
De Costa et al., J. Med. Chem., (1990), vol. 33(11), pp. 3100-3110.
Dorwald, Side Reactions in Organic Synthesis, 2005, Wiley: VCH, Weinheim p. IX of Preface pp. 1-15.
Felig and Frohman, Endocrinology and Metabolism, (McGraw-Hill, New York), 4$^{th}$ Ed. 387-524, 2001.
Gomez-Monterrey., et al. "Stereospecific synthesis of (21t, 3S)-3-amino-2-piperidineacetic acid derivatives for use as a conformational constraint in peptides" Tetrahedron Lett., 1993, 34, 3593-3594.

Grundy et al., Diagnosis and Management of the Metabolic Syndrome, *Circulation*, 2005, 112, 2735-2752.

Hermanowski-Vosatka et al. *J. Exp. Med.*, 2005, 202, 517-527.

Hosoda et al., "Preparation of N-(heterocyclylcarbonyl)amino acids and analogs as prolyl endopeptidase inhibitors", Database CAPLUS on STN (Columbus, OH, USA) No. 118:255342, Abstract, (1993) see RN 147635-61-8.

Huber, "11βHSD1 Inhibitors for Type 2 Diabetes: A Systematic Development Strategy to Assess Pharmacodynamic Activity an Obtain Proof-of-Concept in Man," IBC's 5$^{th}$ Annual Targeting Metabolic Disorders Conference, Feb. 26-27, 2007.

Hughes, et al., "The Total Synthesis of (-)-Amathaspiramide F**," *Angew. Chem. Int. Ed.*, 2002, 41(23) 4556-4559.

Irikura et at., "New antiulcer agents. I. Synthesis and biological activities of 1- acyl-2-, -3-, and -4-substituted benzamidopiperidines." *J. Med. Chem.* 1971, 14, pp. 357-361. (Chem. Abs. 92:174158).

Knoops et al., "Generation of 3-piperidine(methan)amines and cyclic 3-piperidine-methanamines as potential substance P antagonists", *Tetrahedron*, (1997), vol. 53, pp. 12699-12716.

"Known 2-iodomethylbenzoates", 168 pages, 2007.

Leonardi, A. et al., "Synthesis, Pharmacological Evaluation, and Structure—Activity Relationship and Qunatitative Structure—Activity Relationship Studies on Novel Derivatives of 2,4-Diamino-6,7-dimethoxyquinazoline alpha1-Adrenoceptor Antagonists" J. Med. Chem. 42(3):427-437 (1999).

Lewis et al. *J. Chem. Soc. Perkin Trans.* 2, 1991, vol. 10. pp. 1625-1630.

Li et al. Syntheses and SAR of piperidin-3-yl ureas as potent and selective 11β-HSD-1 inhibitors, MEDI 54 Abstract of Presentation at the 233rd ACS National Meeting, Chicago, IL, Mar. 25-29, 2007.

Li et al. Syntheses and SAR of Piperidin-3-yl Ureas as Potent and Selective 11β-HSD-1 inhibitors, Presentation at the 233rd ACS National Meeting, Chicago, IL, Mar. 25-29, 2007.

Louie, et al., *Tetrahedron Lett.*, 1995, 36, 3609.

Mallams, A.K. et al, "Inhibitors of Farnesyl Protein Transferase, 4-Amido, 4-Carbamoyl, and 4-Carboxamido Derivatives of 1-(8-Chloro-6,11-dihydro-5H-benzo[5,6]-cyclohepta[1,2-b]pyridin-11-yl)piperazine and 1-(3-Bromo-8-chloro-6,11-dihydro-5H-benzo[5,6]cyclohepta[1,2-b]pyridine-11-yl)piperazine" J. Med. Chem. 41 (6):877-893 (1998).

Markees et al., *J. Am. Chem. Soc.*, 1949, vol. 71, pp. 2031-2035.

Martin-Martinez et al., "Synthesis and stereochemical structure-activity relationships of 1,3-dioxoperhydropyrido[1,2-c]pyrimidine derivatives: Potent and selective cholecystokinin-A receptor antagonists", *J. Med. Chem.*, 1997, vol. 40, pp. 3402-3407.

Martin, et al. "Do Structurally Similar Molecules Have Similar Biological Activity?", *J. Med. Chem.*, 2002, 45, 4350-4358.

Matsumoto et al., "Direkte Aminolyse von nicht aktivierten Estern bei hohm Druck," *Angew. Chem.*, 1996, 98, 569-570.

Meanwell, et al., "Preparation and testing of 7-amino-1,3-dihydro-2H-imidazo [4,5- b]quinolin-2-ones as phosphodiesterase and blood platelet aggregation inhibitors", Database CAPLUS on STN (Columbus, OH, USA) No. 108:131815, Abstract, (1988) see RN 113288-90-7.

Mehrotra et al., "Discovery of Novel 2,8-Diazaspiro[4,5]decanes as orally Active Glycoprotein IIb-IIIa Antagonist", *J. Med. Chem.*, 2004, 47, pp. 2037-2061.

Messinger et al., "New inhibitors of 17b-hydroxysteroid dehydrogenasse type 1", *Molecular and Cellular Endocrinology*, 2006, 248, 192-198.

Mishani, et al. *Tetrahedron Lett.*, 1996, 37, 319.

Miyabe et al., "The total synthesis of (-)-balanol", *Synlett.*, 1997, pp. 580-582 (Chem. Abs. 130:38227).

Moeller, K.D. et al., "Anodic Amide Oxidations in the Presence of Electron-Rich Phenyl Rings: Evidence for an Intramolecular Electron-Transfer Mechanism" J. Org. Chem., 1991, vol. 56(3):1058-1067 (1991).

Morris, et al., "Amathaspiramides A-F, Novel Brominated Alkaloids from the Marine Bryozoan," *J. Nat. Prod*, 1999, 62, 688-693.

Moya et al., "Synthesis and Biological Evaluation of New Analogies of the Active Fungal Metabolites N-(2-Methyl-3-oxodecanoyl)-2-pyrroline and N-(2-Methyl-3-oxodec-8-enoyl)- 2-pyrroline," *J. Agric. Food Chem.*, 1999, 47, 3866-3871.

Nojima, et al., Spiro Compounds Formation by the Reaction of Cycloalkene with Friedel-Crafts Catalyst. I. Reaction of Cyclohexene with Aluminum Chloride. The Rearrangement of Cyclohexylcyclohexene, *J. Org. Chem.*, 1966, 31 (12), pp. 3966-3969.

Ogura, et al., "[1,4] Addition of (Methylthio p-Tolyl Sulfone to α,β-Unaturated Carbonyl Compounds", *J. Org. Chem.*, 1986, 51, pp. 508-512.

Ohta et al., "Preparation of heterocyclyl moiety-containing diamine derivatives as factor Xa inhibitors"; Chem. Abs. 141:106461, 2004.

Olivier et al., "Binding to albumin of spin-labeled derivatives of clofibric acid", Database CA [Online], Chemical Abstracts Service, Columbus, Ohio, US; retrieved from STN Database Accession No. 1986:45271.

Pekala et al., "Synthesis of N-acyl derivatives of DL-trans-1,2-cyclohexanol", Database CA [Online], Chemical Abstracts Service, Columbus, Ohio, US; retrieved from STN, Database Accession No. 1995:459419.

Poirier et al. "Inhibitors of type II 17b-hydroxysteroid dehydrogenase" Molecular and Cellular Endocrinology 2001, 171, 119-128.

RN 113288-90-7 structure, abstract, and patent family details (3 pages), 1988.

Schelsinger et al., "N-Substituted-Amides," *J. Am. Chem. Soc.*, 1956, 78: 6123-6127.

Scott, F. L. et al., "Synthesis and Reactions of Trihalogeno-Diazabutadienes—New Versatile Synthetic Intermediates", *Tetrahedron Letters*, 47, pp. 4079-4082, 1970.

Shridhar et al., "Synthesis of new 3-methoxy-4-(acylamino)phenyl isothiocyanates and 4'-(isothiocyanatophenoxy)acetamides/isobutyramides as possible anthelmintic agents", Retrieved from STN, Database Accession No. 1987:554038.

Taylor et al., "On the ritter reaction of cyclic hydroxyamines: synthesis of conformationally-restricted reduced amide dipeptide isosteres", *Tetrahedron Letters*, (1996), vol. 37, pp. 1297-1300.

von Geldern et al., *Biorg. Med. Chem. Lett.*, 2005, 15, 195.

Wheatley et al., "Basic Ethers Derived from β-Hydroxyphenethylamines," *J. Org. Chem.*, 1958, 23, 1360-1363.

Wojcik et al., "Catalytic Hydrogenation of Amides to Amines," *J. Am. Chem. Soc.*, 1934, 56, 2419-2424.

Wolff, "Burger's Medicinal Chemistry, 5ed, Part I", John Wiley & Sons, 1995, pp. 975-977.

Xu, et al., "Synthesis of Aza/Oxaspiro-y-lactams by Radical Translocation Cyclization Reastions," *Synlett*, 2005, 12, 1865-1868.

Yao, et al. Discovery of potent and selective 11β-HSD-1 Inhibitors, MEDI 228 Abstract of Presentation at the 233rd ACS National Meeting, Chicago, IL, Mar. 25-29, 2007.

Yao, Discovery of Potent and Orally Active Inhibitors of 11β-Hydroxysteroid Dehydrogenase I, presentation at the 233rd ACS National Meeting, Chicago, IL, Mar. 27, 2007.

Yao et al., "Preparation of cycloalkylearbonylammes and heteroeyeloalkylcarbonylammes as 11β hydroxysteroid dchydrogenase type I inhibitors and mineraloeorticoid receptor antagonist and their use as pharmaceutical", Caplus English Abstract DN 144.6815, Nov. 2005.

Yokoyama et al., "The First Effective Syntheses of Cyanoflurormethylated Amides, Thioamides, and Phosphorus Compunds Using 2-Cyano-2-fluoro-2-phenylacetonitrile and ET$_3$GeNa," *Synthesis*, 8: 1319-1324 (1999).

Zhuo. et al. Discovery and synthesis of nipecotic amide as novel, potent and selective 11β-HSD-1- inhibitors MEDI 48 Abstract, 233rd ACS National Meeting, Chicago, IL, Mar. 25-29, 2007.

Zhuo et al. Discovery of Nipecotic Amides as Novel, Potent and Selective 11βHSD1 Inhibitors, poster at the 233rd ACS National Meeting, Chicago, IL, Mar. 25-29, 2007.

Amendment and Response in Reply to Office Action of Mar. 29, 2007 submitted Jun. 28, 2007 in connection with U.S. Appl. No. 11/281,648 (US20060122210A1).

Amendment in Reply to Action of Jul. 31, 2007 submitted Oct. 30, 2007 in connection with U.S. Appl. No. 11/281,648 (US20060122210A1).

Ex Parte Quayle Action— U.S. Appl. No. 11/122,309 (US20050282858) dated Dec. 14, 2006.
Final Office Action U.S. Appl. No. 11/281,648 (US20060122210A1) dated Dec. 13, 2007.
Int'l Preliminary Report on Patentability— Int'l App. No. PCT/US05/15559 (WO2005/110992) dated Nov. 7, 2006.
Int'l Preliminary Report on—Int. App. No. PCT/US05/041763 (WO/2006/055752), 2007.
Int'l Preliminary Report on Patentability—Int'l App. No. PCT/US05/22170 (WO2006/012173) dated Jan. 11, 2007.
Int'l Preliminary Report on Patentability—Int'l App. No. PCT/US05/22307 (WO2006/012226) dated Dec. 28, 2006.
Int'l Preliminary Report on Patentability—Int'l App. No. PCT/US05/22411 (WO/2006/002349) dated Dec. 28, 2006.
Int'l Preliminary Report on Patentability—Int'l App. No. PCT/US05/22412 (WO2006/002350) dated Dec. 28, 2006.
Int'l Preliminary Report on Patentability—Int'l App. No. PCT/US05/022434 (WO 2006/002361) dated Dec. 28, 2006.
Int'l Preliminary Report on Patentability—Int'l App. No. PCT/US05/028201 (WO2006/020598) dated Feb. 13, 2007.
Int'l Preliminary Report on Patentability—Int'l App. No. PCT/US05/040550 (WO 2006/053024)dated May 30, 2007.
Int'l Preliminary Report on Patentability—Int'l App. No. PCT/US06/036652 (WO2007/038138) dated Mar. 28, 2008.
Int'l Preliminary Report on Patentability—Int'l App. No. PCT/US06/46309 (WO2007/067504) dated Jun. 11, 2008.
Int'l Preliminary Report on Patentability—Int'l App. No. PCT/US07/00695 (WO2007/084314) dated Jul. 15, 2008.
Int'l Preliminary Report on Patentability—Int'l App. No. PCT/US07/002360 (WO2007/089683) dated Aug. 5, 2008.
Int'l Search Report—Int'l App. No. PCT/US05/022434 (WO 2006/002361) dated Mar. 31, 2006.
Int'l Search Report—Int'l App. No. PCT/US05/040550 (WO2006/053024) dated Jul. 17, 2007.
Int'l Search Report—Int'l App. No. PCT/US05/041763 (WO2006/055752) dated Apr. 24, 2007.
Int'l Search Report—Int'l App. No. PCT/US05/15559 (WO2005/110992) dated Aug. 15, 2005.
Int'l Search Report—Int'l App. No. PCT/US05/22170 (WO2006/012173) dated Oct. 18, 2005.
Int'l Search Report—Int'l App. No. PCT/US05/22307 (WO2006/012226) dated Apr. 5, 2006.
Int'l Search Report—Int'l App. No. PCT/US05/22411 (WO/2006/002349) dated Oct. 20, 2005.
Int'l Search Report—Int'l App. No. PCT/US05/22412 (WO 2006/002350) dated Nov. 2, 2005.
Int'l Search Report—Int'l App. No. PCT/US06/036652 (WO2007/038138) dated Feb. 4, 2007.
Int'l Search Report—Int'l App. No. PCT/US06/46309 (WO2007/067504) dated Jul. 9, 2007.
Int'l Search Report—Int'l App. No. PCT/US07/002360 (WO2007/089683) dated Jun. 19, 2007.
Int'l Search Report for PCT/US05/22308 (WO 2006/012227), dated Dec. 2, 2005.
Int'l Search Report for PCT/US2006/046309 (WO2007/067504) dated Aug. 28, 2007.
Int'l Search Report—Int'l App. No. PCT/US07/00695 (WO2007/084314) dated Jan. 31, 2008.
Int'l Search Report—Int'l App. No. PCT/US07/063050 (WO2007/101270) dated Sep. 7, 2007.
Int'l Search Report—Int'l App. No. PCT/US07/063055 (WO2007/103719) dated Oct. 22, 2007.
Int'l Search Report—Int'l App. No. PCT/U507/067753 (WO2007/130898) dated Sep. 26, 2007.
Int'l Search Report—Int'l App. No. PCT/US07/0669033 (WO2007/137066) dated Jan. 24, 2008.
Non-Final Office Action U.S. Appl. No. 11/159,724 (US20060009471) dated Mar. 24, 2008.
Non-Final Office Action U.S. Appl. No. 11/159,862 (US20050288338) dated May 6, 2008.
Non-Final Office Action U.S. Appl. No. 11/159,865 (US20050288329) dated Apr 6, 2008.
Non-Final Office Action U.S. Appl. No. 11/199,763 (US20060122197) Mar. 4, 2008.
Non-Final Office Action U.S. Appl. No. 11/281,648 (US20060122210) dated Jul. 31, 2007.
Non-Final Office Action U.S. Appl. No. 11/281,648 (US20060122210) dated Mar. 29, 2007.
Non-Final Office Action U.S. Appl. No. 11/784,450 (US20070179142) dated Dec. 13, 2007.
Office Action—Chilean App. No. 3389-2006 dated Aug. 8, 2008.
Office Action—Eurasian App. No. 200602062/2006120048 dated Dec. 20, 2007.
Office Action—Eurasian App. No. 200700117 dated Mar. 27, 2008.
Office Action—Eurasian Patent App. No. 200700118 dated Mar. 20, 2008.
Office Action—Georgian App. No. AP2005 009823 dated Nov. 22, 2007.
Office Action—Georgian Patent App. No. AP2005009824 dated Nov. 22, 2007.
Office Action—Georgian App. No. AP2005010125 dated Feb. 11, 2008.
Opposition—Costa Rican App. No. 8793 dated Aug. 5, 2008.
Opposition—Ecuadorian App. No. Sp-Jun. 7114 dated May 23, 2007.
Preliminary Examination Results—Viet. App. No. 1-2006-02007 dated Apr. 27, 2007.
Search Report—Eurasian App. 200701036 dated Dec. 10, 2007.
Search Report—Georgian App. No. AP2005009920 dated Apr. 21, 2008.
Search Report—Singapore App. No. SG200607426 dated Dec. 14, 2007.
Search Report—Singapore App. No. 200700845-1 dated May 19, 2008.
Supplementary European Search Report 05763245.7 dated Apr. 9, 2008.
Supplementary Partial EP Search Report—Eur. App. No. 05762543.6 dated Nov. 30, 2007.
Supplementary European Search Report 05763380.2 dated Dec. 6, 2007.
Supplementary Partial EP Search Report—Eur. App. No. 05763383.6 dated Dec. 3, 2007.
Supplementary Partial EP Search Report—EP Appl. No. 05762850.5 dated Dec. 13, 2007.

* cited by examiner

2-METHYLPROPANAMIDES AND THEIR USE AS PHARMACEUTICALS

CROSS REFERENCE TO RELATED APPLICATIONS

This application claims benefit of U.S. Provisional Application Ser. No. 60/582,477, filed Jun. 24, 2004, the disclosure of which is incorporated herein by reference in its entirety.

FIELD OF THE INVENTION

The present invention relates to modulators of 11-β hydroxyl steroid dehydrogenase type 1 (11βHSD1) and/or mineralocorticoid receptor (MR), compositions thereof and methods of using the same.

BACKGROUND OF THE INVENTION

Glucocorticoids are steroid hormones that regulate fat metabolism, function and distribution. In vertebrates, glucocorticoids also have profound and diverse physiological effects on development, neurobiology, inflammation, blood pressure, metabolism and programmed cell death. In humans, the primary endogenously-produced glucocorticoid is cortisol. Cortisol is synthesized in the zona fasciculate of the adrenal cortex under the control of a short-term neuroendocrine feedback circuit called the hypothalamic-pituitary-adrenal (HPA) axis. Adrenal production of cortisol proceeds under the control of adrenocorticotrophic hormone (ACTH), a factor produced and secreted by the anterior pituitary. Production of ACTH in the anterior pituitary is itself highly regulated, driven by corticotropin releasing hormone (CRH) produced by the paraventricular nucleus of the hypothalamus. The HPA axis maintains circulating cortisol concentrations within restricted limits, with forward drive at the diurnal maximum or during periods of stress, and is rapidly attenuated by a negative feedback loop resulting from the ability of cortisol to suppress ACTH production in the anterior pituitary and CRH production in the hypothalamus.

Aldosterone is another hormone produced by the adrenal cortex; aldosterone regulates sodium and potassium homeostasis. Fifty years ago, a role for aldosterone excess in human disease was reported in a description of the syndrome of primary aldosteronism (Conn, (1955), J. Lab. Clin. Med. 45: 6-17). It is now clear that elevated levels of aldosterone are associated with deleterious effects on the heart and kidneys, and are a major contributing factor to morbidity and mortality in both heart failure and hypertension.

Two members of the nuclear hormone receptor superfamily, glucocorticoid receptor (GR) and mineralocorticoid receptor (MR), mediate cortisol function in vivo, while the primary intracellular receptor for aldosterone is the MR. These receptors are also referred to as 'ligand-dependent transcription factors,' because their functionality is dependent on the receptor being bound to its ligand (for example, cortisol); upon ligand-binding these receptors directly modulate transcription via DNA-binding zinc finger domains and transcriptional activation domains.

Historically, the major determinants of glucocorticoid action were attributed to three primary factors: 1) circulating levels of glucocorticoid (driven primarily by the HPA axis), 2) protein binding of glucocorticoids in circulation, and 3) intracellular receptor density inside target tissues. Recently, a fourth determinant of glucocorticoid function was identified: tissue-specific pre-receptor metabolism by glucocorticoid-activating and -inactivating enzymes. These 11-beta-hydroxysteroid dehydrogenase (11-β-HSD) enzymes act as pre-receptor control enzymes that modulate activation of the GR and MR by regulation of glucocorticoid hormones. To date, two distinct isozymes of 11-beta-HSD have been cloned and characterized: 11βHSD1 (also known as 11-beta-HSD type 1, 11betaHSD1, HSD11B1, HDL, and HSD11L) and 11βHSD2. 11βHSD1 and 11βHSD2 catalyze the interconversion of hormonally active cortisol (corticosterone in rodents) and inactive cortisone (11-dehydrocorticosterone in rodents). 11βHSD1 is widely distributed in rat and human tissues; expression of the enzyme and corresponding mRNA have been detected in lung, testis, and most abundantly in liver and adipose tissue. 11βHSD1 catalyzes both 11-beta-dehydrogenation and the reverse 11-oxoreduction reaction, although 11βHSD1 acts predominantly as a NADPH-dependent oxoreductase in intact cells and tissues, catalyzing the activation of cortisol from inert cortisone (Low et al. (1994) J. Mol. Endocrin. 13: 167-174) and has been reported to regulate glucocorticoid access to the GR. Conversely, 11βHSD2 expression is found mainly in mineralocorticoid target tissues such as kidney, placenta, colon and salivary gland, acts as an NAD-dependent dehydrogenase catalyzing the inactivation of cortisol to cortisone (Albiston et al. (1994) Mol. Cell. Endocrin. 105: R11-R17), and has been found to protect the MR from glucocorticoid excess, such as high levels of receptor-active cortisol (Blum, et al., (2003) Prog. Nucl. Acid Res. Mol. Biol. 75:173-216).

In vitro, the MR binds cortisol and aldosterone with equal affinity. The tissue specificity of aldosterone activity, however, is conferred by the expression of 11βHSD2 (Funder et al. (1988), Science 242: 583-585). The inactivation of cortisol to cortisone by 11βHSD2 at the site of the MR enables aldosterone to bind to this receptor in vivo. The binding of aldosterone to the MR results in dissociation of the ligand-activated MR from a multiprotein complex containing chaperone proteins, translocation of the MR into the nucleus, and its binding to hormone response elements in regulatory regions of target gene promoters. Within the distal nephron of the kidney, induction of serum and glucocorticoid inducible kinase-1 (sgk-1) expression leads to the absorption of $Na^+$ ions and water through the epithelial sodium channel, as well as potassium excretion with subsequent volume expansion and hypertension (Bhargava et al., (2001), Endo 142: 1587-1594).

In humans, elevated aldosterone concentrations are associated with endothelial dysfunction, myocardial infarction, left ventricular atrophy, and death. In attempts to modulate these ill effects, multiple intervention strategies have been adopted to control aldosterone overactivity and attenuate the resultant hypertension and its associated cardiovascular consequences. Inhibition of angiotensin-converting enzyme (ACE) and blockade of the angiotensin type 1 receptor (AT1R) are two strategies that directly impact the rennin-angiotensin-aldosterone system (RAAS). However, although ACE inhibition and AT1R antagonism initially reduce aldosterone concentrations, circulating concentrations of this hormone return to baseline levels with chronic therapy (known as 'aldosterone escape'). Importantly, co-administration of the MR antagonist Spironolactone or Eplerenone directly blocks the deleterious effects of this escape mechanism and dramatically reduces patient mortality (Pitt et al., New England J. Med. (1999), 341: 709-719; Pitt et al., New England J. Med. (2003), 348: 1309-1321). Therefore, MR antagonism may be an important treatment strategy for many patients with hypertension and cardiovascular disease, particularly those hypertensive patients at risk for target-organ damage.

Mutations in either of the genes encoding the 11-beta-HSD enzymes are associated with human pathology. For example, 11βHSD2 is expressed in aldosterone-sensitive tissues such as the distal nephron, salivary gland, and colonic mucosa where its cortisol dehydrogenase activity serves to protect the intrinsically non-selective MR from illicit occupation by cortisol (Edwards et al. (1988) Lancet 2: 986-989). Individuals with mutations in 11βHSD2 are deficient in this cortisol-inactivation activity and, as a result, present with a syndrome of apparent mineralocorticoid excess (also referred to as 'SAME') characterized by hypertension, hypokalemia, and sodium retention (Wilson et al. (1998) Proc. Natl. Acad. Sci. 95: 10200-10205). Likewise, mutations in 11βHSD1, a primary regulator of tissue-specific glucocorticoid bioavailability, and in the gene encoding a co-localized NADPH-generating enzyme, hexose 6-phosphate dehydrogenase (H6PD), can result in cortisone reductase deficiency (CRD), in which activation of cortisone to cortisol does not occur, resulting in adrenocorticotropin-mediated androgen excess. CRD patients excrete virtually all glucocorticoids as cortisone metabolites (tetrahydrocortisone) with low or absent cortisol metabolites (tetrahydrocortisols). When challenged with oral cortisone, CRD patients exhibit abnormally low plasma cortisol concentrations. These individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

The importance of the HPA axis in controlling glucocorticoid excursions is evident from the fact that disruption of homeostasis in the HPA axis by either excess or deficient secretion or action results in Cushing's syndrome or Addison's disease, respectively (Miller and Chrousos (2001) Endocrinology and Metabolism, eds. Felig and Frohman (McGraw-Hill, New York), $4^{th}$ Ed.: 387-524). Patients with Cushing's syndrome (a rare disease characterized by systemic glucocorticoid excess originating from the adrenal or pituitary tumors) or receiving glucocorticoid therapy develop reversible visceral fat obesity. Interestingly, the phenotype of Cushing's syndrome patients closely resembles that of Reaven's metabolic syndrome (also known as Syndrome X or insulin resistance syndrome) the symptoms of which include visceral obesity, glucose intolerance, insulin resistance, hypertension, type 2 diabetes and hyperlipidemia (Reaven (1993) Ann. Rev. Med. 44: 121-131). However, the role of glucocorticoids in prevalent forms of human obesity has remained obscure because circulating glucocorticoid concentrations are not elevated in the majority of metabolic syndrome patients. In fact, glucocorticoid action on target tissue depends not only on circulating levels but also on intracellular concentration, locally enhanced action of glucocorticoids in adipose tissue and skeletal muscle has been demonstrated in metabolic syndrome. Evidence has accumulated that enzyme activity of 11βHSD1, which regenerates active glucocorticoids from inactive forms and plays a central role in regulating intracellular glucocorticoid concentration, is commonly elevated in fat depots from obese individuals. This suggests a role for local glucocorticoid reactivation in obesity and metabolic syndrome.

Given the ability of 11βHSD1 to regenerate cortisol from inert circulating cortisone, considerable attention has been given to its role in the amplification of glucocorticoid function. 11βHSD1 is expressed in many key GR-rich tissues, including tissues of considerable metabolic importance such as liver, adipose, and skeletal muscle, and, as such, has been postulated to aid in the tissue-specific potentiation of glucocorticoid-mediated antagonism of insulin function. Considering a) the phenotypic similarity between glucocorticoid excess (Cushing's syndrome) and the metabolic syndrome with normal circulating glucocorticoids in the latter, as well as b) the ability of 11βHSD1 to generate active cortisol from inactive cortisone in a tissue-specific manner, it has been suggested that central obesity and the associated metabolic complications in syndrome X result from increased activity of 11βHSD1 within adipose tissue, resulting in 'Cushing's disease of the omentum' (Bujalska et al. (1997) Lancet 349: 1210-1213). Indeed, 11βHSD1 has been shown to be upregulated in adipose tissue of obese rodents and humans (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Additional support for this notion has come from studies in mouse transgenic models. Adipose-specific overexpression of 11βHSD1 under the control of the aP2 promoter in mouse produces a phenotype remarkably reminiscent of human metabolic syndrome (Masuzaki et al. (2001) Science 294: 2166-2170; Masuzaki et al. (2003) J. Clinical Invest. 112: 83-90). Importantly, this phenotype occurs without an increase in total circulating corticosterone, but rather is driven by a local production of corticosterone within the adipose depots. The increased activity of 11βHSD1 in these mice (2-3 fold) is very similar to that observed in human obesity (Rask et al. (2001) J. Clin. Endocrinol. Metab. 86: 1418-1421). This suggests that local 11βHSD1-mediated conversion of inert glucocorticoid to active glucocorticoid can have profound influences whole body insulin sensitivity.

Based on this data, it would be predicted that the loss of 11βHSD1 would lead to an increase in insulin sensitivity and glucose tolerance due to a tissue-specific deficiency in active glucocorticoid levels. This is, in fact, the case as shown in studies with 11βHSD1-deficient mice produced by homologous recombination (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). These mice are completely devoid of 11-keto reductase activity, confirming that 11βHSD1 encodes the only activity capable of generating active corticosterone from inert 11-dehydrocorticosterone. 11βHSD1-deficient mice are resistant to diet- and stress-induced hyperglycemia, exhibit attenuated induction of hepatic gluconeogenic enzymes (PEPCK, G6P), show increased insulin sensitivity within adipose, and have an improved lipid profile (decreased triglycerides and increased cardio-protective HDL). Additionally, these animals show resistance to high fat diet-induced obesity. Taken together, these transgenic mouse studies confirm a role for local reactivation of glucocorticoids in controlling hepatic and peripheral insulin sensitivity, and suggest that inhibition of 11βHSD1 activity may prove beneficial in treating a number of glucocorticoid-related disorders, including obesity, insulin resistance, hyperglycemia, and hyperlipidemia.

Data in support of this hypothesis has been published. Recently, it was reported that 11βHSD1 plays a role in the pathogenesis of central obesity and the appearance of the metabolic syndrome in humans. Increased expression of the 11βHSD1 gene is associated with metabolic abnormalities in obese women and that increased expression of this gene is suspected to contribute to the increased local conversion of cortisone to cortisol in adipose tissue of obese individuals (Engeli, et al., (2004) Obes. Res. 12: 9-17).

A new class of 11βHSD1 inhibitors, the arylsulfonamidothiazoles, was shown to improve hepatic insulin sensitivity and reduce blood glucose levels in hyperglycemic strains of mice (Barf et al. (2002) J. Med. Chem. 45: 3813-3815; Alberts et al. Endocrinology (2003) 144: 4755-4762). Furthermore, it was recently reported that selective inhibitors of 11βHSD1 can ameliorate severe hyperglycemia in genetically diabetic obese mice. Thus, 11βHSD1 is a promising pharmaceutical target for the treatment of the Metabolic Syndrome (Masuzaki, et al., (2003) Curr. Drug Targets Immune Endocr. Metabol. Disord. 3: 255-62).

A. Obesity and Metabolic Syndrome

As described above, multiple lines of evidence suggest that inhibition of 11βHSD1 activity can be effective in combating obesity and/or aspects of the metabolic syndrome cluster, including glucose intolerance, insulin resistance, hyperglycemia, hypertension, and/or hyperlipidemia. Glucocorticoids are known antagonists of insulin action, and reductions in local glucocorticoid levels by inhibition of intracellular cortisone to cortisol conversion should increase hepatic and/or peripheral insulin sensitivity and potentially reduce visceral adiposity. As described above, 11βHSD1 knockout mice are resistant to hyperglycemia, exhibit attenuated induction of key hepatic gluconeogenic enzymes, show markedly increased insulin sensitivity within adipose, and have an improved lipid profile. Additionally, these animals show resistance to high fat diet-induced obesity (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). Thus, inhibition of 11βHSD1 is predicted to have multiple beneficial effects in the liver, adipose, and/or skeletal muscle, particularly related to alleviation of component(s) of the metabolic syndrome and/or obesity.

B. Pancreatic Function

Glucocorticoids are known to inhibit the glucose-stimulated secretion of insulin from pancreatic beta-cells (Billaudel and Sutter (1979) Horm. Metab. Res. 11: 555-560). In both Cushing's syndrome and diabetic Zucker fa/fa rats, glucose-stimulated insulin secretion is markedly reduced (Ogawa et al. (1992) J. Clin. Invest. 90: 497-504). 11βHSD1 mRNA and activity has been reported in the pancreatic islet cells of ob/ob mice and inhibition of this activity with carbenoxolone, an 11βHSD1 inhibitor, improves glucose-stimulated insulin release (Davani et al. (2000) J. Biol. Chem. 275: 34841-34844). Thus, inhibition of 11βHSD1 is predicted to have beneficial effects on the pancreas, including the enhancement of glucose-stimulated insulin release.

C. Cognition and Dementia

Mild cognitive impairment is a common feature of aging that may be ultimately related to the progression of dementia. In both aged animals and humans, inter-individual differences in general cognitive function have been linked to variability in the long-term exposure to glucocorticoids (Lupien et al. (1998) Nat. Neurosci. 1: 69-73). Further, dysregulation of the FPA axis resulting in chronic exposure to glucocorticoid excess in certain brain subregions has been proposed to contribute to the decline of cognitive function (McEwen and Sapolsky (1995) Curr. Opin. Neurobiol. 5: 205-216). 11βHSD1 is abundant in the brain, and is expressed in multiple subregions including the hippocampus, frontal cortex, and cerebellum (Sandeep et al. (2004) Proc. Natl. Acad. Sci. Early Edition: 1-6). Treatment of primary hippocampal cells with the 11βHSD1 inhibitor carbenoxolone protects the cells from glucocorticoid-mediated exacerbation of excitatory amino acid neurotoxicity (Rajan et al. (1996) J. Neurosci. 16: 65-70). Additionally, 11βHSD1-deficient mice are protected from glucocorticoid-associated hippocampal dysfunction that is associated with aging (Yau et al. (2001) Proc. Natl. Acad. Sci. 98: 4716-4721). In two randomized, double-blind, placebo-controlled crossover studies, administration of carbenoxolone improved verbal fluency and verbal memory (Sandeep et al. (2004) Proc. Natl. Acad. Sci. Early Edition: 1-6). Thus, inhibition of 11βHSD1 is predicted to reduce exposure to glucocorticoids in the brain and protect against deleterious glucocorticoid effects on neuronal function, including cognitive impairment, dementia, and/or depression.

D. Intra-Ocular Pressure

Glucocorticoids can be used topically and systemically for a wide range of conditions in clinical ophthalmology. One particular complication with these treatment regimens is corticosteroid-induced glaucoma. This pathology is characterized by a significant increase in intra-ocular pressure (IOP). In its most advanced and untreated form, IOP can lead to partial visual field loss and eventually blindness. IOP is produced by the relationship between aqueous humour production and drainage. Aqueous humour production occurs in the non-pigmented epithelial cells (NPE) and its drainage is through the cells of the trabecular meshwork. 11βHSD1 has been localized to NPE cells (Stokes et al. (2000) Invest. Ophthalmol. Vis. Sci. 41: 1629-1683; Rauz et al. (2001) Invest. Ophthalmol. Vis. Sci. 42: 2037-2042) and its function is likely relevant to the amplification of glucocorticoid activity within these cells. This notion has been confirmed by the observation that free cortisol concentration greatly exceeds that of cortisone in the aqueous humour (14:1 ratio). The functional significance of 11βHSD1 in the eye has been evaluated using the inhibitor carbenoxolone in healthy volunteers (Rauz et al. (2001) Invest. Ophthalmol. Vis. Sci. 42: 2037-2042). After seven days of carbenoxolone treatment, IOP was reduced by 18%. Thus, inhibition of 11βHSD1 in the eye is predicted to reduce local glucocorticoid concentrations and IOP, producing beneficial effects in the management of glaucoma and other visual disorders.

E. Hypertension

Adipocyte-derived hypertensive substances such as leptin and angiotensinogen have been proposed to be involved in the pathogenesis of obesity-related hypertension (Matsuzawa et al. (1999) Ann. N.Y. Acad. Sci. 892: 146-154; Wajchenberg (2000) Endocr. Rev. 21: 697-738). Leptin, which is secreted in excess in aP2-11βHSD1 transgenic mice (Masuzaki et al. (2003) J. Clinical Invest. 112: 83-90), can activate various sympathetic nervous system pathways, including those that regulate blood pressure (Matsuzawa et al. (1999) Ann. N.Y. Acad. Sci. 892: 146-154). Additionally, the renin-angiotensin system (RAS) has been shown to be a major determinant of blood pressure (Walker et al. (1979) Hypertension 1: 287-291). Angiotensinogen, which is produced in liver and adipose tissue, is the key substrate for renin and drives RAS activation. Plasma angiotensinogen levels are markedly elevated in aP2-11βHSD1 transgenic mice, as are angiotensin II and aldosterone (Masuzaki et al. (2003) J. Clinical Invest. 112: 83-90). These forces likely drive the elevated blood pressure observed in aP2-11βHSD1 transgenic mice. Treatment of these mice with low doses of an angiotensin II receptor antagonist abolishes this hypertension (Masuzaki et al. (2003) J. Clinical Invest. 112: 83-90). This data illustrates the importance of local glucocorticoid reactivation in adipose tissue and liver, and suggests that hypertension may be caused or exacerbated by 11βHSD1 activity. Thus, inhibition of 11βHSD1 and reduction in adipose and/or hepatic glucocorticoid levels is predicted to have beneficial effects on hypertension and hypertension-related cardiovascular disorders.

F. Bone Disease

Glucocorticoids can have adverse effects on skeletal tissues. Continued exposure to even moderate glucocorticoid doses can result in osteoporosis (Cannalis (1996) J. Clin. Endocrinol. Metab. 81: 3441-3447) and increased risk for fractures. Experiments in vitro confirm the deleterious effects of glucocorticoids on both bone-resorbing cells (also known as osteoclasts) and bone forming cells (osteoblasts). 11βHSD1 has been shown to be present in cultures of human primary osteoblasts as well as cells from adult bone, likely a mixture of osteoclasts and osteoblasts (Cooper et al. (2000) Bone 27: 375-381), and the 11βHSD1 inhibitor carbenoxolone has been shown to attenuate the negative effects of glucocorticoids on bone nodule formation (Bellows et al. (1998) Bone 23: 119-125). Thus, inhibition of 11βHSD1 is predicted to decrease the local glucocorticoid concentration within osteoblasts and osteoclasts, producing beneficial effects in various forms of bone disease, including osteoporosis.

Small molecule inhibitors of 11βHSD1 are currently being developed to treat or prevent 11βHSD1-related diseases such as those described above. For example, certain amide-based inhibitors are reported in WO 2004/089470, WO 2004/089896, WO 2004/056745, and WO 2004/065351.

Antagonists of 11βHSD1 have been evaluated in human clinical trials (Kurukulasuriya, et al., (2003) Curr. Med. Chem. 10: 123-53).

In light of the experimental data indicating a role for 11βHSD1 in glucocorticoid-related disorders, metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS), therapeutic agents aimed at augmentation or suppression of these metabolic pathways, by modulating glucocorticoid signal transduction at the level of 11βHSD1 are desirable.

Furthermore, because the MR binds to aldosterone (its natural ligand) and cortisol with equal affinities, compounds that are designed to interact with the active site of 11βHSD1 (which binds to cortisone/cortisol) may also interact with the MR and act as antagonists. Because the MR is implicated in heart failure, hypertension, and related pathologies including atherosclerosis, arteriosclerosis, coronary artery disease, thrombosis, angina, peripheral vascular disease, vascular wall damage, and stroke, MR antagonists are desirable and may also be useful in treating complex cardiovascular, renal, and inflammatory pathologies including disorders of lipid metabolism including dyslipidemia or hyperlipoproteinaemia, diabetic dyslipidemia, mixed dyslipidemia, hypercholesterolemia, hypertriglyceridemia, as well as those associated with type 1 diabetes, type 2 diabetes, obesity, metabolic syndrome, and insulin resistance, and general aldosterone-related target-organ damage.

As evidenced herein, there is a continuing need for new and improved drugs that target 11βHSD1 and/or MR. The compounds, compositions and methods described herein help meet this and other needs.

SUMMARY OF THE INVENTION

The present invention provides, inter alia, compounds of Formulas I, II, IIa, IIaa, IIb, III, IIIa, IV and V:

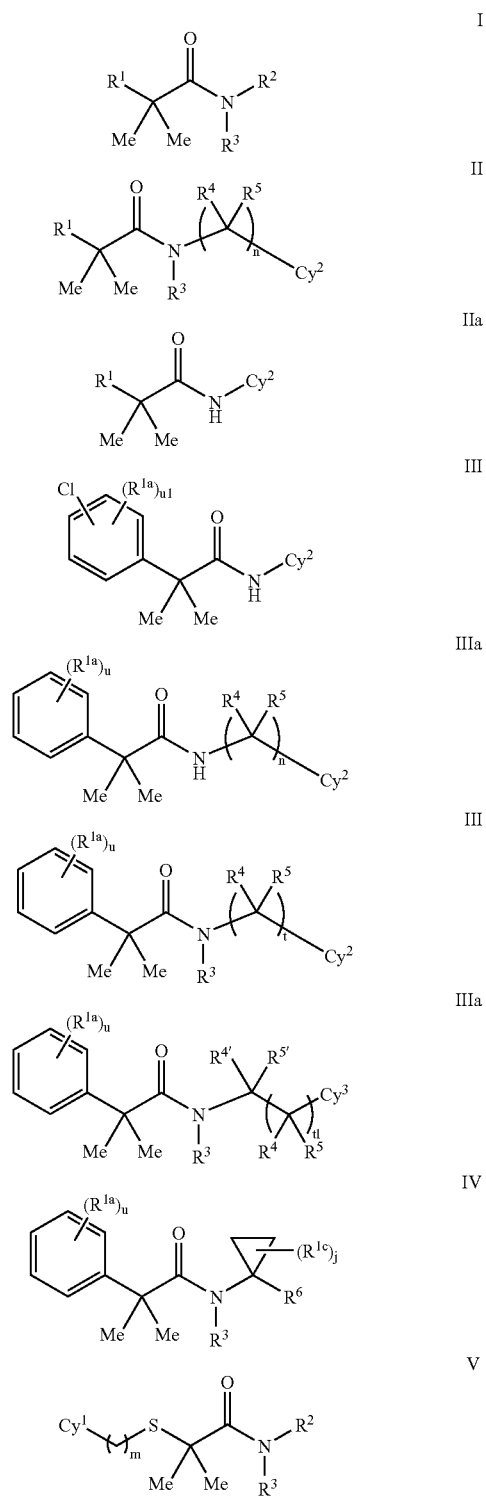

or pharmaceutically acceptable salts or prodrugs thereof, wherein constituent members are defined herein.

The present invention further provides compositions comprising compounds of the invention and a pharmaceutically acceptable carrier.

The present invention further provides methods of modulating 11βHSD1 or MR by contacting 11βHSD1 or MR with a compound of the invention.

The present invention further provides methods of inhibiting 11βHSD1 or MR by contacting 11βHSD1 or MR with a compound of the invention.

The present invention further provides methods of inhibiting the conversion of cortisone to cortisol in a cell by contacting the cell with a compound of the invention.

The present invention further provides methods of inhibiting the production of cortisol in a cell by contacting the cell with a compound of the invention.

The present invention further provides methods of treating diseases associated with activity or expression of 11βHSD1 or MR.

DETAILED DESCRIPTION

The present invention provides, inter alia, compounds of Formula I:

I $$R^1 \overset{O}{\underset{Me \ Me}{\diagdown}} N \diagdown R^2 \\ R^3$$

or pharmaceutically acceptable salts or prodrugs thereof, wherein:

$R^1$ is phenyl, $Cy^1$-$(CH_2)_m$—O— or $Cy^1$-$(CH_2)_m$—S—, wherein said phenyl is optionally substituted by 1, 2, 3, 4 or 5 $R^{1a}$;

$R^2$ is —$(CR^4R^5)_n Cy^2$, —$(CR^4R^5)_t Cy^3$, or $Cy^4$;

$R^3$ is H, $C_{1-6}$ alkyl or $C_{3-6}$ cycloalkyl;

$R^4$ and $R^5$ are each, independently, H, halo, OH, CN, $C_{1-4}$ alkyl, $C_{1-4}$ alkoxy, wherein said $C_{1-4}$ alkyl or $C_{1-4}$ alkoxy is optionally substituted with one or more $R^{4a}$;

$R^6$ is H or $C_{1-6}$ alkyl optionally substituted by one or more OH;

$R^{1a}$ and $R^{1b}$ are, each independently, halo, CN, $NO_2$, $OR^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)_2NR^cR^d$, $S(O)_2R^b$, or $S(O)_2NR^cR^d$;

$R^{1c}$ is halo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, phenyl, benzyl, $C(O)OR^g$ or $OR^g$;

$R^{4a}$ is halo, CN, $NO_2$, OH, $C_{1-4}$ alkoxy, $C_{1-4}$ haloalkoxy, amino, $C_{1-4}$ alkylamino or $C_{2-8}$ dialkylamino;

$Cy^1$ is aryl, heteroaryl, cycloalkyl or heterocycloalkyl, each optionally substituted by 1, 2, 3, 4 or 5-W—X—Y—Z;

$Cy^2$ is:

$Cy^3$ is phenyl optionally substituted by one or more $R^{1a}$;
$Cy^4$ is:

U is $CH_2$, NH or O;

W, W' and W" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-4}$ alkylenyl, $C_{2-6}$ alkenylenyl or $C_{2-6}$ alkynylenyl is each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

X, X' and X" are each, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

Y, Y' and Y" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z, Z' and Z" are each, independently, H, halo, CN, $NO_2$, OH, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein two —W—X—Y—Z together with two adjacent atoms to which they are attached optionally form a 3-20 membered cycloalkyl group or 3-20 membered heterocycloalkyl group, each optionally substituted by 1, 2 or 3-W"—X"—Y"—Z";

or wherein two —W—X—Y—Z together with two adjacent atoms to which they are attached optionally form a 5- or 6-membered aryl or 5- or 6-membered heteroaryl group, each optionally substituted by 1, 2 or 3-W"—X"—Y"—Z";

wherein two —W'—X'—Y'—Z' together with the atom to which they are both attached optionally form a 3-20 membered cycloalkyl group or 3-20 membered heterocycloalkyl group, each optionally substituted by 1, 2 or 3-W"—X"—Y"—Z";

wherein two —W'—X'—Y'—Z' together with two adjacent atoms to which they are attached optionally form a 3-20 membered cycloalkyl group or 3-20 membered heterocycloalkyl group, each optionally substituted by 1, 2 or 3-W"—X"—Y"—Z";

or wherein two —W'—X'—Y'—Z' together with two adjacent atoms to which they are attached optionally form a 5- or 6-membered aryl or 5- or 6-membered heteroaryl group, each optionally substituted by 1, 2 or 3-W"—X"—Y"—Z";

wherein —W—X—Y—Z is other than H;
wherein —W'—X'—Y'—Z' is other than H;
wherein —W"—X"—Y"—Z" is other than H;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^e$ and $R^f$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^e$ and $R^f$ together with the N atom to which they are attached form a 4-, 5-, 6- or 7-membered heterocycloalkyl group;

$R^g$ is H, $C_{1-6}$ alkyl, $C_{1-6}$ haloalkyl, $C_{2-6}$ alkenyl, $C_{2-6}$ alkynyl, aryl, heteroaryl, cycloalkyl, arylalkyl, heteroarylalkyl or cycloalkylalkyl;

j is 0, 1, 2, or 3;
m is 0, 1, or 2;
n is 0, 1, 2, or 3;
q1 is 0, 1, 2, 3 or 4;
q2 is 0, 1, 2 or 3;
q3 is 1, 2, 3, 4 or 5;
q is 0, 1, 2, 3, 4 or 5;
r is 1 or 2; and
t is 2 or 3.

In some embodiments, when $R^1$ is phenyl optionally substituted by 1, 2, 3, 4 or 5 $R^{1a}$ and $R^2$ is $(CR^4R^5)_tCy^3$, at least one of $R^4$ and $R^5$ is other than H.

In some embodiments, when $R^1$ is phenyl optionally substituted by 1, 2, 3, 4 or 5 $R^{1a}$ and $R^2$ is $Cy^2$, then $Cy^2$ is other than 1-[3-(2-methoxyphenoxy)benzyl]-piperidine-4-yl, 1-[3-(2-methoxyphenoxy)-benzyl]-pyrrolidin-3-yl, 1,2,2,6,6-pentamethyl-piperidin-4-yl or cyclohexyl substituted by one $NR^cR^d$.

In some embodiments, when $R^2$ is cyclohexyl, $R^1$ is other than 3,5-di-tert-butyl-4-hydroxyphenyl.

In some embodiments, $R^1$ is phenyl optionally substituted by 1, 2, 3, 4 or 5 halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, $C_{1-6}$ haloalkyl, aryl, cycloalkyl, heteroaryl or heterocycloalkyl.

In some embodiments, $R^1$ is phenyl substituted by 1, 2 or 3 halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-4}$ alkyl, $C_{2-4}$ alkenyl, $C_{2-6}$ alkynyl, $C_{1-6}$ haloalkyl, aryl, cycloalkyl, heteroaryl or heterocycloalkyl.

In some embodiments, $R^1$ is phenyl substituted by 1, 2 or 3 halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, or $C_{1-6}$ haloalkyl.

In some embodiments, $R^1$ is 4-chlorophenyl optionally substituted by 1 or 2 halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, or $C_{1-6}$ haloalkyl.

In some embodiments:
$R^2$ is $—(CR^4R^5)_nCy^2$;
$Cy^2$ is:

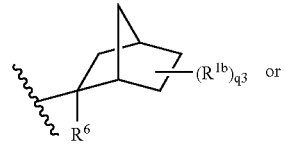 or

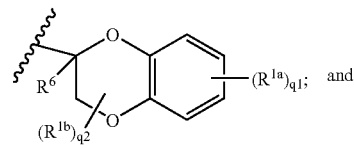 and $R^6$ is H.

In some embodiments, q1 is 0 or 1.
In some embodiments, q1 is 0.
In some embodiments, q2 is 0 or 1.
In some embodiments, q2 is 0.
In some embodiments, q3 is 1, 2 or 3.
In some embodiments, q3 is 1.
In some embodiments:
$R^2$ is $—(CR^4R^5)_nCy^2$;
$Cy^2$ is:

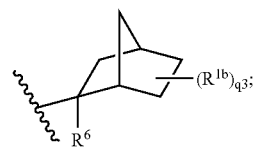

$R^{1b}$ is halo, CN, $NO_2$, OH, $C_{1-4}$ alkoxy optionally substituted by one or more OH, $C_{1-4}$ haloalkoxy, or $C_{1-6}$ alkyl optionally substituted by 1, 2, or 3 OH, $C_{1-4}$ alkoxy, halo, CN or $NO_2$; and q3 is 1, 2 or 3.

In some embodiments:

$R^2$ is —$(CR^4R^5)_nCy^2$; and $Cy^2$ is

[structure: 5-membered ring with $R^6$, N–$R^8$, (W'—X'—Y'—Z')$_{q1}$, subscript r]

$R^8$ is $C_{2-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{2-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by one or more halo or OH; and q1 is 0, 1, 2, 3 or 4.

In some embodiments:

$R^2$ is —$(CR^4R^5)_nCy^2$;

$R^6$ is H;

$R^8$ is $C_{2-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein $C_{2-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by one or more halo or OH;

$Cy^2$ is

[structure: 5-membered ring with $R^6$, N–$R^8$, (W'—X'—Y'—Z')$_{q1}$, subscript r]

W'—X'—Y'—Z' is independently halo, CN, $NO_2$, $OR^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, $C_{1-6}$ alkyl, $C_{2-6}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group; and q1 is 0, 1, 2, 3 or 4.

In some embodiments:

$R^2$ is —$(CR^4R^5)_nCy^2$;

$Cy^2$ is:

[structure: 5-membered ring with $R^6$, O, (W'—X'—Y'—Z')$_q$, subscript r]; and $R^6$ is H.

In some embodiments, r is 1.

In some embodiments, q is 0, 1 or 2.

In some embodiments:

$R^2$ is —$(CR^4R^5)_nCy^2$;

$Cy^2$ is:

[structure: 5-membered ring with $R^6$, O, (W'—X'—Y'—Z')$_q$, subscript r]

W'—X'—Y'—Z' is independently halo, CN, $NO_2$, $OR^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; and $R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group.

In some embodiments:

$R^2$ is —$(CR^4R^5)_nCy^2$;

$Cy^2$ is:

[structure: 5-membered ring with $R^6$, (W'—X'—Y'—Z')$_q$] or

[structure: 6-membered ring with $R^6$, (W'—X'—Y'—Z')$_v$];

W'—X'—Y'—Z' is independently halo, CN, NO$_2$, OR$^a$, C$_{1-4}$ alkoxy, C$_{1-4}$ haloalkoxy, amino, C$_{1-4}$ alkylamino, C$_{2-8}$ dialkylamino, C$_{1-6}$ alkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl, wherein said C$_{1-4}$ alkoxy, C$_{1-4}$ haloalkoxy, C$_{1-6}$ alkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

R$^a$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^b$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^c$ and R$^d$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group; and v is 2, 3, 4 or 5.

In some embodiments, v is 2 or 3.

In some embodiments:
R$^2$ is —(CR$^4$R$^5$)$_n$Cy$^2$;
Cy$^2$ is:

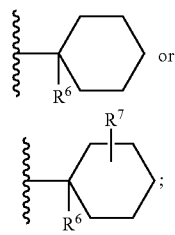

R$^7$ is halo, CN, NO$_2$, OH, OR$^a$, SR$^a$, C(O)R$^b$, C(O)NR$^c$R$^d$, C(O)OR$^a$, OC(O)R$^b$, OC(O)NR$^c$R$^d$, S(O)R$^b$, S(O)NR$^c$R$^d$, S(O)$_2$R$^b$, S(O)$_2$NR$^c$R$^d$, C$_{1-4}$ alkoxy, C$_{1-6}$ alkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl, wherein said C$_{1-4}$ alkoxy, C$_{1-4}$ alkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

R$^a$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^b$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl; and R$^c$ and R$^d$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group.

In some embodiments, when R$^2$ is —(CR$^4$R$^5$)$_n$Cy$^2$, n is 0 and Cy$^2$ is cyclohexyl, then R$^1$ is other than 3,5-di-tert-butyl-4-hydroxyphenyl.

In some embodiments:
R$^2$ is —(CR$^4$R$^5$)$_n$Cy$^2$;
Cy$^2$ is:

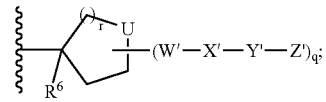

q is 2, 3, 4 or 5; and two —W'—X'—Y'—Z' together with the atom to which they are both attached to form a 3-20 membered cycloalkyl group or 3-20 membered heterocycloalkyl group optionally substituted by 1, 2 or 3-W"—X"—Y"—Z".

In some embodiments:
R$^2$ is —(CR$^4$R$^5$)$_n$Cy$^2$;
Cy$^2$ is:

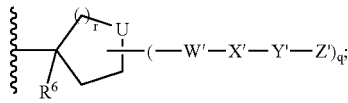

q is 2, 3, 4 or 5; and two —W'—X'—Y'—Z' together with two adjacent atoms to which they are attached optionally form a 5- or 6-membered aryl or 5- or 6-membered heteroaryl group, each optionally substituted by 1, 2 or 3-W"—X"—Y"—Z".

In some embodiments:
R$^2$ is —(CR$^4$R$^5$)$_n$Cy$^2$;
R$^6$ is H or C$_{1-6}$ alkyl optionally substituted by one or more OH;
Cy$^2$ is:

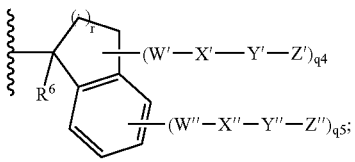

r is 1 or 2;

—W'—X'—Y'—Z' and —W"—X"—Y"—Z" are each halo, CN, NO$_2$, OR$^a$, C$_{1-4}$ alkoxy, C$_{1-4}$ haloalkoxy, amino, C$_{1-4}$ alkylamino, C$_{2-8}$ dialkylamino, C$_{1-6}$ alkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl, wherein said C$_{1-4}$ alkoxy, C$_{1-4}$ haloalkoxy, C$_{1-6}$ alkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

R$^a$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^b$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

q4 is 0, 1, 2 or 3; and q5 is 0, 1, 2 or 3.

In some embodiments, q4 is 0 or 1.

In some embodiments, q5 is 0 or 1.

In some embodiments, $R^2$ is $(CR^4R^5)_n Cy^2$ and n is 0.

In some embodiments, $R^2$ is $(CR^4R^5)_n Cy^2$, and n is 1, 2 or 3.

In some embodiments, $R^2$ is $(CR^4R^5)_n Cy^2$ and n is 1.

In some embodiments, $R^2$ is $(CR^4R^5)_t Cy^3$ and t is 2.

In some embodiments, $R^2$ is $(CR^4R^5)_t Cy^3$ and t is 3.

In some embodiments:

$R^2$ is $(CR^4R^5)(CR^4R^5)_{t1} Cy^3$;

$R^{4'}$ is halo, OH, CN, $C_{1-4}$alkyl, $C_{1-4}$ alkoxy, wherein said $C_{1-4}$ alkyl or $C_{1-4}$ alkoxy is optionally substituted with one or more halo, CN, $NO_2$, OH, $C_{1-4}$ alkoxy, or $C_{1-4}$ haloalkoxy;

$R^{5'}$ is, H, halo, OH, CN, $C_{1-4}$alkyl, $C_{1-4}$ alkoxy, wherein said $C_{1-4}$ alkyl or $C_{1-4}$ alkoxy is optionally substituted with one or more halo, CN, $NO_2$, OH, $C_{1-4}$ alkoxy, $C_{1-4}$ haloalkoxy, amino, $C_{1-4}$ alkylamino or $C_{2-8}$ dialkylamino; and t1 is 1 or 2.

In some embodiments, t1 is 1.

In some embodiments, t1 is 2.

In some embodiments, $R^{4'}$ is OH, $C_{1-4}$alkyl, $C_{1-4}$ alkoxy or $C_{1-4}$alkyl optionally substituted by OH or $C_{1-4}$ alkoxy.

In some embodiments, $R^{5'}$ is H, OH, $C_{1-4}$alkyl, $C_{1-4}$ alkoxy or $C_{1-4}$alkyl optionally substituted by OH or $C_{1-4}$ alkoxy.

In some embodiments, $R^2$ is

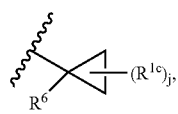

and $R^6$ is H or $C_{1-6}$ alkyl.

In some embodiments, j is 0 or 1.

In some embodiments, $R^3$ is H or $C_{1-6}$ alkyl.

In some embodiments, $R^3$ is H.

In some embodiments, $R^4$ and $R^5$ are each, independently, H, OH, $C_{1-4}$alkyl, $C_{1-4}$ alkoxy or $C_{1-4}$alkyl optionally substituted by OH or $C_{1-4}$ alkoxy.

In some embodiments, $R^6$ is H.

In some embodiments, $R^6$ is $C_{1-6}$ alkyl optionally substituted by OH.

In some embodiments, $R^6$ is $C_{1-4}$ alkyl.

In some embodiments, $R^6$ is $C_{1-4}$ alkyl substituted by OH.

In some embodiments, $R^{1a}$ and $R^{1b}$ are each, independently, halo, CN, OH, $C_{1-6}$ alkyl or $C_{1-4}$ alkoxy, wherein said $C_{1-6}$ alkyl or $C_{1-4}$ alkoxy is optionally substituted by one or more OH, CN, halo, $C_{1-6}$ alkyl or $C_{1-4}$ alkoxy.

In some embodiments, $R^{1a}$ is halo, OH, $C_{1-6}$ alkyl or $C_{1-4}$ alkoxy, wherein said $C_{1-6}$ alkyl or $C_{1-4}$ alkoxy is optionally substituted by one or more OH, halo, $C_{1-6}$ alkyl or $C_{1-4}$ alkoxy.

In some embodiments, $R^{1b}$ is halo, OH, $C_{1-6}$ alkyl or $C_{1-4}$ alkoxy, wherein said $C_{1-6}$ alkyl or $C_{1-4}$ alkoxy is optionally substituted by one or more OH, halo, $C_{1-6}$ alkyl or $C_{1-4}$ alkoxy.

In some embodiments, $R^{1c}$ is halo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, phenyl or benzyl.

In some embodiments, $R^{1c}$ is $C_{1-4}$ alkyl, phenyl or benzyl.

In some embodiments, —W'—X'—Y'—Z' and —W"—X"—Y"—Z" are each halo, CN, $NO_2$, $OR^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$.

In some embodiments, the compounds of the invention have Formula II:

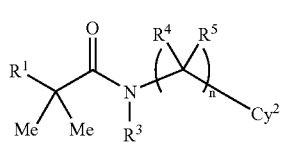

II or pharmaceutically acceptable salts or prodrugs thereof, wherein constituent variables are defined herein above:

$R^1$ is phenyl optionally substituted by 1, 2, 3, 4 or 5 $R^{1a}$;

$R^3$ is H, $C_{1-6}$ alkyl or $C_{3-6}$ cycloalkyl;

$R^4$ and $R^5$ are each, independently, H, halo, OH, CN, $C_{1-4}$ alkyl, $C_{1-4}$ alkoxy, wherein said $C_{1-4}$ alkyl or $C_{1-4}$ alkoxy is optionally substituted with one or more $R^{4a}$;

$R^6$ is H or $C_{1-6}$ alkyl optionally substituted by one or more OH;

$R^{1a}$ and $R^{1b}$ are, each independently, halo, CN, $NO_2$, $OR^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-4}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^{4a}$ is halo, CN, $NO_2$, OH, $C_{1-4}$ alkoxy, $C_{1-4}$ haloalkoxy, amino, $C_{1-4}$ alkylamino or $C_{2-8}$ dialkylamino;

$Cy^2$ is:

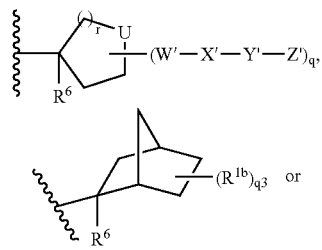

-continued

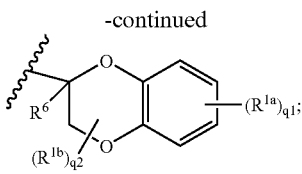

U is CH$_2$, NH or O;

W' and W" are each, independently, absent, C$_{1-6}$ alkylenyl, C$_{2-6}$ alkenylenyl, C$_{2-6}$ alkynylenyl, O, S, NR$^e$, CO, COO, CONR$^e$, SO, SO$_2$, SONR$^e$, or NR$^e$CONR$^f$, wherein said C$_{1-6}$ alkylenyl, C$_{2-6}$ alkenylenyl or C$_{2-6}$ alkynylenyl is optionally substituted by 1, 2 or 3 halo, OH, C$_{1-4}$ alkoxy, C$_{1-4}$ haloalkoxy, amino, C$_{1-4}$ alkylamino or C$_{2-8}$ dialkylamino;

X' and X" are each, independently, absent, C$_{1-6}$ alkylenyl, C$_{2-6}$ alkenylenyl, C$_{2-6}$ alkynylenyl, aryl, cycloalkyl, heteroaryl or heterocycloalkyl, wherein said C$_{1-6}$ alkylenyl, C$_{2-6}$ alkenylenyl, C$_{2-6}$ alkynylenyl, cycloalkyl, heteroaryl or heterocycloalkyl is optionally substituted by one or more halo, CN, NO$_2$, OH, C$_{1-4}$ alkoxy, C$_{1-4}$ haloalkoxy, amino, C$_{1-4}$ alkylamino or C$_{2-8}$ dialkylamino;

Y' and Y" are each, independently, absent, C$_{1-6}$ alkylenyl, C$_{2-6}$ alkenylenyl, C$_{2-6}$ alkynylenyl, O, S, NR$^e$, CO, COO, CONR$^e$, SO, SO$_2$, SONR$^e$, or NR$^e$CONR$^f$, wherein said C$_{1-6}$ alkylenyl, C$_{2-6}$ alkenylenyl or C$_{2-6}$ alkynylenyl is optionally substituted by 1, 2 or 3 halo, OH, C$_{1-4}$ alkoxy, C$_{1-4}$ haloalkoxy, amino, C$_{1-4}$ alkylamino or C$_{2-8}$ dialkylamino;

Z' and Z" are each, independently, H, halo, CN, NO$_2$, OH, C$_{1-4}$ alkoxy, C$_{1-4}$ haloalkoxy, amino, C$_{1-4}$ alkylamino or C$_{2-8}$ dialkylamino, C$_{1-6}$ alkyl, C$_{2-6}$ alkenyl, C$_{2-6}$ alkynyl, aryl, cycloalkyl, heteroaryl or heterocycloalkyl, wherein said C$_{1-6}$ alkyl, C$_{2-6}$ alkenyl, C$_{2-6}$ alkynyl, aryl, cycloalkyl, heteroaryl or heterocycloalkyl is optionally substituted by 1, 2 or 3 halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

wherein two —W'—X'—Y'—Z' together with the atom to which they are both attached optionally form a 3-20 membered cycloalkyl group or 3-20 membered heterocycloalkyl group, each optionally substituted by 1, 2 or 3-W"—X"—Y"—Z";

wherein two —W'—X'—Y'—Z' together with two adjacent atoms to which they are attached optionally form a 3-20 membered cycloalkyl group or 3-20 membered heterocycloalkyl group, each optionally substituted by 1, 2 or 3-W"—X"—Y"—Z";

or wherein two —W'—X'—Y'—Z' together with two adjacent atoms to which they are attached optionally form a 5- or 6-membered aryl or 5- or 6-membered heteroaryl group, each optionally substituted by 1, 2 or 3-W"—X"—Y"—Z";

wherein —W'—X'—Y'—Z' is other than H;

wherein —W"—X"—Y"—Z" is other than H;

R$^a$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^b$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^c$ and R$^d$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group;

R$^e$ and R$^f$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^e$ and R$^f$ together with the N atom to which they are attached form a 4-, 5-, 6- or 7-membered heterocycloalkyl group;

n is 0, 1, 2, or 3;

q1 is 0, 1, 2, 3 or 4;

q2 is 0, 1, 2 or 3;

q3 is 1, 2, 3, 4 or 5;

q is 0, 1, 2, 3, 4 or 5; and r is 1 or 2.

In some embodiments, when n is 0, Cy$^2$ is other than 1-[3-(2-methoxyphenoxy)benzyl]-piperidine-4-yl, 1-[3-(2-methoxyphenoxy)benzyl]-pyrrolidin-3-yl, 1,2,2,6,6-pentamethyl-piperidin-4-yl or cyclohexyl substituted by one NR$^c$R$^d$.

In some embodiments, when n is 0 and Cy$^2$ is cyclohexyl, R$^1$ is other than 3,5-di-tert-butyl-4-hydroxyphenyl.

In some embodiments:

Cy$^2$ is:

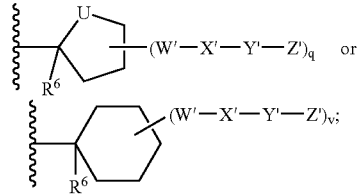

—W'—X'—Y'—Z' is independently halo, CN, NO$_2$, OR$^a$, C$_{1-4}$ alkoxy, C$_{1-4}$ haloalkoxy, amino, C$_{1-4}$ alkylamino, C$_{2-8}$ dialkylamino, C$_{1-6}$ alkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl, wherein said C$_{1-4}$ alkoxy, C$_{1-4}$ haloalkoxy, C$_{1-6}$ alkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R, or S(O)$_2$NR$^c$R$^d$;

R$^a$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^b$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl; and R$^c$ and R$^d$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group;

U is CH$_2$ or O; and v is 2, 3, 4 or 5.

In some embodiments:

Cy$^2$ is:

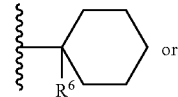

-continued

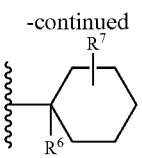

R⁷ is halo, CN, NO₂, OH, OR$^a$, SR$^a$, C(O)R$^b$, C(O)NR$^c$R$^d$, C(O)OR$^a$, OC(O)R$^b$, OC(O)NR$^c$R$^d$, S(O)R$^b$, S(O)NR$^c$R$^d$, S(O)₂R$^b$, S(O)₂NR$^c$R$^d$, $C_{1-4}$ alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-4}$ alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO₂, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)₂R$^b$, or S(O)₂NR$^c$R$^d$;

R$^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

R$^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; and R$^c$ and R$^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group.

In some embodiments, when n is 0 and Cy² is cyclohexyl, R¹ is other than 3,5-di-tert-butyl-4-hydroxyphenyl.

In some embodiments:
Cy² is:

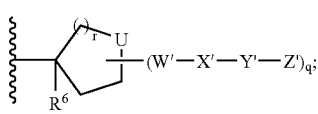

q is 2, 3, 4 or 5; and two —W'—X'—Y'—Z' together with the atom to which they are both attached form a 3-20 membered cycloalkyl group or 3-20 membered heterocycloalkyl group optionally substituted by 1, 2 or 3-W"—X"—Y"—Z".

In some embodiments:
Cy² is:

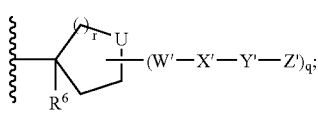

q is 2, 3, 4 or 5; and two —W'—X'—Y'—Z' together with two adjacent atoms to which they are attached optionally form a 5- or 6-membered aryl or 5- or 6-membered heteroaryl group, each optionally substituted by 1, 2 or 3-W"—X"—Y"—Z".

In some embodiments:
R⁶ is H;
Cy² is:

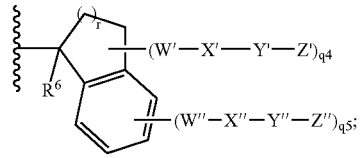

r is 1 or 2;

—W'—X'—Y'—Z' and —W"—X"—Y"—Z" are each halo, CN, NO₂, OR$^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO₂, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)₂R$^b$, or S(O)₂NR$^c$R$^d$;

R$^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

R$^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

R$^c$ and R$^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group;

q4 is 0, 1, 2 or 3; and
q5 is 0, 1, 2 or 3.

In some embodiments, n is 0 or 1

The present invention further provides compounds of Formula IIa:

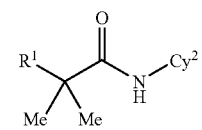

IIa or pharmaceutically acceptable salts or prodrugs thereof, wherein constituent variables are defined hereinabove:

R¹ is phenyl optionally substituted by 1, 2, 3, 4 or 5 R$^{1a}$;

R⁶ is H or $C_{1-6}$ alkyl optionally substituted by one or more OH;

R⁷ is halo, CN, NO₂, OH, OR$^a$, SR$^a$, C(O)R$^b$, C(O)NR$^c$R$^d$, C(O)OR$^a$, OC(O)R$^b$, OC(O)NR$^c$R$^d$, S(O)R$^b$, S(O)NR$^c$R$^d$, S(O)₂R$^b$, S(O)₂NR$^c$R$^d$, C alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkyl or heterocycloalkyl, wherein said $C_{1-4}$ alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkyl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

Cy$^2$ is:

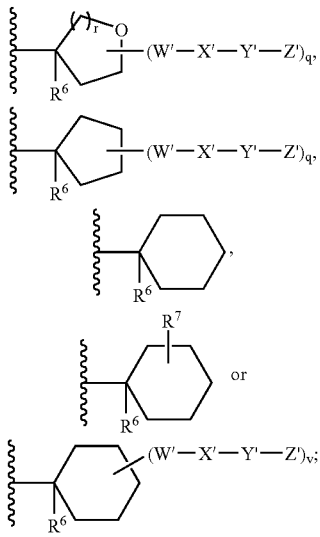

R$^{1a}$ is halo, CN, NO$_2$, OR$^a$, C$_{1-4}$ alkoxy, C$_{1-4}$ haloalkoxy, amino, C$_{1-4}$ alkylamino, C$_{2-8}$ dialkylamino, C$_{1-6}$ alkyl, C$_{2-6}$ alkenyl, C$_{2-6}$ alkynyl, aryl, cycloalkyl, heteroaryl or heterocycloalkyl, wherein said C$_{1-4}$ alkoxy, C$_{1-4}$ haloalkoxy, C$_{1-6}$ alkyl, C$_{2-6}$ alkenyl, C$_{2-6}$ alkynyl, aryl, cycloalkyl, heteroaryl or heterocycloalkyl is optionally substituted by 1, 2 or 3 halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

W' and W" are each, independently, absent, C$_{1-6}$ alkylenyl, C$_{2-6}$ alkenylenyl, C$_{2-6}$ alkynylenyl, O, S, NR$^e$, CO, COO, CONR$^e$, SO, SO$_2$, SONR$^e$, or NR$^e$CONR$^f$, wherein said C$_{1-6}$ alkylenyl, C$_{2-6}$ alkenylenyl or C$_{2-6}$ alkynylenyl is optionally substituted by 1, 2 or 3 halo, OH, C$_{1-4}$ alkoxy, C$_{1-4}$ haloalkoxy, amino, C$_{1-4}$ alkylamino or C$_{2-8}$ dialkylamino;

X' and X" are each, independently, absent, C$_{1-6}$ alkylenyl, C$_{2-6}$ alkenylenyl, C$_{2-6}$ alkynylenyl, aryl, cycloalkyl, heteroaryl or heterocycloalkyl, wherein said C$_{1-6}$ alkylenyl, C$_{2-6}$ alkenylenyl, C$_{2-6}$ alkynylenyl, cycloalkyl, heteroaryl or heterocycloalkyl is optionally substituted by one or more halo, CN, NO$_2$, OH, C$_{1-4}$ alkoxy, C$_{1-4}$ haloalkoxy, amino, C$_{1-4}$ alkylamino or C$_{2-8}$ dialkylamino;

Y' and Y" are each, independently, absent, C$_{4-6}$ alkylenyl, C$_{2-6}$ alkenylenyl, C$_{2-6}$ alkynylenyl, O, S, NR$^e$, CO, COO, CONR$^e$, SO, SO$_2$, SONR$^e$, or NR$^e$CONR$^f$, wherein said C$_{1-6}$ alkylenyl, C$_{2-6}$ alkenylenyl or C$_{2-6}$ alkynylenyl is optionally substituted by 1, 2 or 3 halo, OH, C$_{1-4}$ alkoxy, C$_{1-4}$ haloalkoxy, amino, C$_{1-4}$ alkylamino or C$_{2-8}$ dialkylamino;

Z' and Z" are each, independently, H, halo, CN, NO$_2$, OH, C$_{1-4}$ alkoxy, C$_{1-4}$ haloalkoxy, amino, C$_{1-4}$ alkylamino or C$_{2-8}$ dialkylamino, C$_{1-6}$ alkyl, C$_{2-6}$ alkenyl, C$_{2-6}$ alkynyl, aryl, cycloalkyl, heteroaryl or heterocycloalkyl, wherein said C$_{1-6}$ alkyl, C$_{2-6}$ alkenyl, C$_{2-6}$ alkynyl, aryl, cycloalkyl, heteroaryl or heterocycloalkyl is optionally substituted by 1, 2 or 3 halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

wherein two —W'—X'—Y'—Z' together with the atom to which they are both attached optionally form a 3-20 membered cycloalkyl group or 3-20 membered heterocycloalkyl group, each optionally substituted by 1, 2 or 3-W"—X"—Y"—Z";

wherein two —W'—X'—Y'—Z' together with two adjacent atoms to which they are attached optionally form a 3-20 membered cycloalkyl group or 3-20 membered heterocycloalkyl group, each optionally substituted by 1, 2 or 3-W"—X"—Y"—Z";

or wherein two —W'—X'—Y'—Z' together with two adjacent atoms to which they are attached optionally form a 5- or 6-membered aryl or heteroaryl group, each optionally substituted by 1, 2 or 3 wherein —W'—X'—Y'—Z' is other than H;

wherein —W"—X"—Y"—Z" is other than H;

R$^a$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^b$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^c$ and R$^d$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group;

R$^e$ and R$^f$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^e$ and R$^f$ together with the N atom to which they are attached form a 4-, 5-, 6- or 7-membered heterocycloalkyl group;

q is 0, 1, 2, 3, 4 or 5;

r is 1 or 2;

t is 2 or 3; and v is 2, 3, 4 or 5.

In some embodiments, when Cy$^2$ is cyclohexyl, R$^1$ is other than 3,5-di-tert-butyl-4-hydroxyphenyl.

The present invention further provides compounds of Formula IIaa:

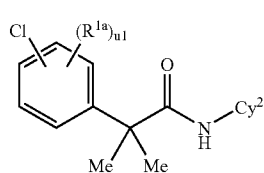

or pharmaceutically acceptable salts or prodrugs thereof, wherein constituent variables are defined hereinabove, and u1 is 0, 1, 2, 3 or 4.

In some embodiments, u1 is 0 or 1.

The present invention further provides compounds of Formula IIb:

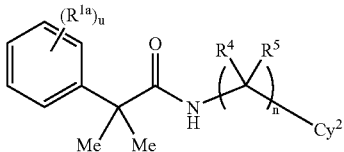

IIb or pharmaceutically acceptable salts or prodrugs thereof, wherein constituent variables are defined hereinabove:

$R^4$ and $R^5$ are each, independently, H, halo, OH, CN, $C_{1-4}$ alkyl, $C_{1-4}$ alkoxy, wherein said $C_{1-4}$ alkyl or $C_{1-4}$ alkoxy is optionally substituted with one or more $R^{4a}$;

$R^6$ is H or $C_{1-6}$ alkyl optionally substituted by one or more OH;

$R^{1a}$ and $R^{1b}$ are, each independently, halo, CN, $NO_2$, OR, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, OR, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^{4a}$ is halo, CN, $NO_2$, OH, $C_{1-4}$ alkoxy, $C_{1-4}$ haloalkoxy, amino, $C_{1-4}$ alkylamino or $C_{2-8}$ dialkylamino;

$Cy^2$ is:

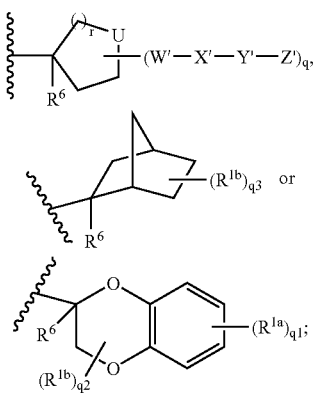

U is $CH_2$, NH or O;

W' and W" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-4}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

X' and X" are each, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

Y' and Y" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z' and Z" are each, independently, H, halo, CN, $NO_2$, OH, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein two —W'—X'—Y'—Z' together with the atom to which they are both attached optionally form a 3-20 membered cycloalkyl group or 3-20 membered heterocycloalkyl group, each optionally substituted by 1, 2 or 3-W"—X"—Y"—Z";

wherein two —W'—X'—Y'—Z' together with two adjacent atoms to which they are attached optionally form a 3-20 membered cycloalkyl group or 3-20 membered heterocycloalkyl group, each optionally substituted by 1, 2 or 3-W"—X"—Y"—Z";

or wherein two —W'—X'—Y'—Z' together with two adjacent atoms to which they are attached optionally form a 5- or 6-membered aryl or 5- or 6-membered heteroaryl group, each optionally substituted by 1, 2 or 3-W"—X"—Y"—Z";

wherein —W'—X'—Y'—Z' is other than H;

wherein —W"—X"—Y"—Z" is other than H;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-4}$ alkyl, $C_1$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^e$ and $R^f$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^e$ and $R^f$ together with the N atom to which they are attached form a 4-, 5-, 6- or 7-membered heterocycloalkyl group;

n is 1, 2 or 3;

q1 is 0, 1, 2, 3 or 4;

q2 is 0, 1, 2 or 3;

q3 is 1, 2 or 3;

q is 0, 1, 2, 3, 4 or 5;

r is 1 or 2; and u is 0, 1, 2, 3, 4 or 5.

In some embodiments, n is 1.

The present invention further provides compounds of Formula III:

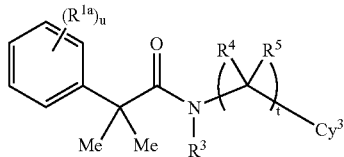

or pharmaceutically acceptable salts or prodrugs thereof, wherein constituent variables are defined hereinabove.

In some embodiments:

t is 2 or 3; and u is 0, 1, 2, 3, 4 or 5.

In some embodiments, at least one of $R^4$ and $R^5$ is other than H.

The present invention further provides compounds of Formula IIIa:

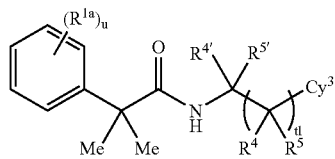

or pharmaceutically acceptable salts or prodrugs thereof, wherein constituent variables are defined hereinabove:

$R^{4'}$ is halo, OH, CN, $C_{1-4}$alkyl, $C_{1-4}$ alkoxy, wherein said $C_{1-4}$ alkyl or $C_{1-4}$ alkoxy is optionally substituted with one or more halo, CN, $NO_2$, OH, $C_{1-4}$ alkoxy, or $C_{1-4}$ haloalkoxy; and $R^{5'}$ is H, halo, OH, CN, $C_{1-4}$alkyl, $C_{1-4}$ alkoxy, wherein said $C_{1-4}$ alkyl or $C_{1-4}$ alkoxy is optionally substituted with one or more $R^{4a}$; and t1 is 1 or 2.

In some embodiments, t1 is 1.

In some embodiments, t1 is 2.

In some embodiments, t1 is 2.

In some embodiments, $R^{4'}$ is OH, $C_{1-4}$alkyl, $C_{1-4}$ alkoxy, wherein said $C_{1-4}$ alkyl or $C_{1-4}$ alkoxy is optionally substituted with one or more OH, $C_{1-4}$ alkoxy, or $C_{1-4}$ haloalkoxy.

In some embodiments, $R^{4'}$ is $C_{1-4}$ alkyl optionally substituted with one or more OH or $C_{1-4}$ alkoxy.

The present invention further provides compounds of Formula IV:

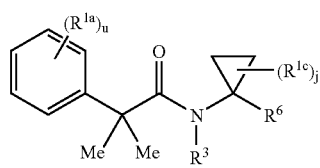

or pharmaceutically acceptable salts or prodrugs thereof, wherein constituent variables are defined hereinabove.

In some embodiments:

$R^3$ is H, $C_{1-6}$ alkyl or $C_{3-6}$ cycloalkyl;

$R^6$ is H or $C_{1-6}$ alkyl optionally substituted by one or more OH;

$R^{1a}$ is halo, CN, $NO_2$, $OR^a$, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^{1c}$ is halo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, phenyl, benzyl, $C(O)OR^g$ or $OR^g$;

$R^a$ is H, $C_{1-6}$ alkyl, $C_{1-4}$ haloalkyl, $C_{2-6}$ alkenyl, $C_{2-6}$ alkynyl, aryl, cycloalkyl, heteroaryl or heterocycloalkyl;

$R^b$ is H, $C_{1-4}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-4}$ alkyl, $C_{1-4}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^g$ is H, $C_{1-6}$ alkyl, $C_{1-6}$ haloalkyl, $C_{2-6}$ alkenyl, $C_{2-6}$ alkynyl, aryl, heteroaryl, cycloalkyl, arylalkyl, heteroarylalkyl or cycloalkylalkyl;

u is 0, 1, 2, 3, 4 or 5; and j is 0, 1, 2 or 3.

In some embodiments, $R^3$ is H.

In some embodiments, $R^6$ is H.

In some embodiments, w is 0 or 1.

In some embodiments, $R^{1c}$ is OH, $C_{1-4}$ alkyl, $C_{1-4}$ haloalkyl, $C_{1-4}$ hydroxyalkyl, $C_{1-4}$ alkoxy, $C_{1-4}$ haloalkoxy, phenyl or benzyl.

In some embodiments, $R^{1c}$ is phenyl or benzyl.

The present invention further provides compounds of Formula V:

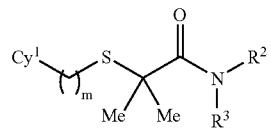

or pharmaceutically acceptable salts or prodrugs thereof, wherein constituent variables are defined hereinabove.

In some embodiments:

$Cy^1$ is aryl, heteroaryl, cycloalkyl or heterocycloalkyl, each optionally substituted by 1, 2, 3, 4 or 5-W—X—Y—Z; and m is 0, 1, or 2.

In some embodiments, $Cy^1$ is aryl optionally substituted by 1, 2, 3, 4 or 5-W—X—Y—Z.

In some embodiments, $Cy^1$ is aryl substituted by 1, 2 or 3-W—X—Y—Z.

In some embodiments, $Cy^1$ is unsubstituted aryl.

In some embodiments, $Cy^1$ is phenyl substituted by 1, 2 or 3-W—X—Y—Z.

In some embodiments, $Cy^1$ is phenyl.

In some embodiments, m is 0 or 1.

In some embodiments, m is 0 and $Cy^1$ is phenyl.

In some embodiments, m is 1 and $Cy^1$ is phenyl substituted by 1 halo.

In some embodiments, $R^2$ is $(CR^4R^5)_nCy^2$.

In some embodiments, $R^2$ is $(CR^4R^5)_nCy^2$, and wherein n is 0 or 1.

In some embodiments:
$R^2$ is —$(CR^4R^5)_nCy^2$;
$Cy^2$ is:

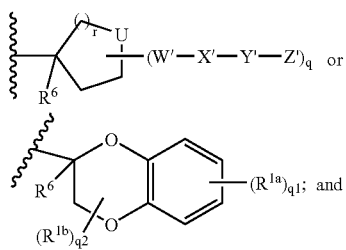

n is 1.
In some embodiments:
$R^2$ is —$(CR^4R^5)_nCy^2$;
$Cy^2$ is:

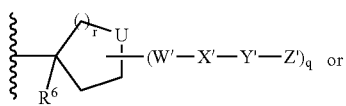

n is 0.
In some embodiments, $R^2$ is —$(CR^4R^5)_tCy^3$.
In some embodiments:
$R^2$ is $(CR^4R^5)(CR^4R^5)_{t1}Cy^3$;
$R^{4'}$ is halo, OH, CN, $C_{1-4}$alkyl, $C_{1-4}$ alkoxy, wherein said $C_{1-4}$ alkyl or $C_{1-4}$ alkoxy is optionally substituted with one or more halo, CN, $NO_2$, OH, $C_{1-4}$ alkoxy, or $C_{1-4}$ haloalkoxy;
$R^{5'}$ is H, halo, OH, CN, $C_{1-4}$alkyl, $C_{1-4}$ alkoxy, wherein said $C_{1-4}$ alkyl or $C_{1-4}$ alkoxy is optionally substituted with one or more halo, CN, $NO_2$, OH, $C_{1-4}$ alkoxy, $C_{1-4}$ haloalkoxy, amino, $C_{1-4}$ alkylamino or $C_{2-8}$ dialkylamino; and
t1 is 1 or 2.

In some embodiments, $R^2$ is

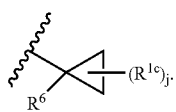

In some embodiments:
$R^2$ is:

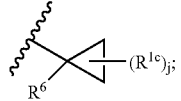

$R^{1c}$ is halo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, phenyl, or benzyl; and
j is 0, 1 or 2.

In some embodiments, $R^3$ is H.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R. In another example, when an optionally multiple substituent is designated in the form:

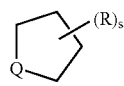

then it is understood that substituent R can occur s number of times on the ring, and R can be a different moiety at each occurrence. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" refers to a divalent alkyl linking group.

As used herein, "alkenyl" refers to an alkyl group having one or more double carbon-carbon bonds. Example alkenyl groups include ethenyl, propenyl, and the like. The term "alkenylenyl" refers to a divalent linking alkenyl group. An example $C_1$ alkenylenyl is —CH=.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) ring systems as well as 2-ring, 3-ring, 4-ring spiro system (e.g., having 8 to 20 ring-forming atoms). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo, pryido or thieno derivatives of pentane, pentene, hexane, and the like. Carbon atoms of the cycloalkyl group can be optionally oxidized, e.g. bear an oxo or sulfildo group to form CO or CS.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. Heterocycloalkyl groups can be mono- or polycyclic (e.g., having 2, 3, 4 or more fused rings or having a 2-ring, 3-ring, 4-ring spiro system (e.g., having 8 to 20 ring-forming atoms)). Heteroatoms or carbon atoms of the heterocycloalkyl group can be optionally oxidized, e.g., bearing one or two oxo or sulfildo groups to form SO, $SO_2$, CO, NO, etc. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, as well as radicals of 3H-isobenzofuran-1-one, 1,3-dihydro-isobenzofuran, 2,3-dihydro-benzo[d]isothiazole 1,1-dioxide, and the like.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used here, "haloalkoxy" refers to an O-haloalkyl group. An example haloalkoxy group is $OCF_3$.

As used herein, "arylalkyl" refers to alkyl substituted by aryl and "cycloalkylalkyl" refers to alkyl substituted by cycloalkyl. An example arylalkyl group is benzyl.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The compounds of the invention can be prepared, for example, using the reaction pathways and techniques as described below.

A series of carboxamides of formula 2 can be prepared by the method outlined in Scheme 1. Carboxylic acids 1 can be coupled to an appropriate amine (primary or secondary) using a coupling reagent such as BOP to provide the desired product 2.

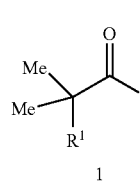

Scheme 1

A series of carboxylic acids of formula 1 can be prepared by the method outlined in Scheme 2. Mono-methylation of alpha-substituted methyl ester 3 with methyl bromide or methyl iodide provides mono-methylated carboxylates 4, which upon treatment with a second methyl bromide or methyl iodide in the presence of a suitable base such as sodium hydride and in a suitable solvent such as DMSO yields bis(methylated) carboxylates 5. Finally basic hydrolysis of 5 gives the corresponding carboxylic acids 1.

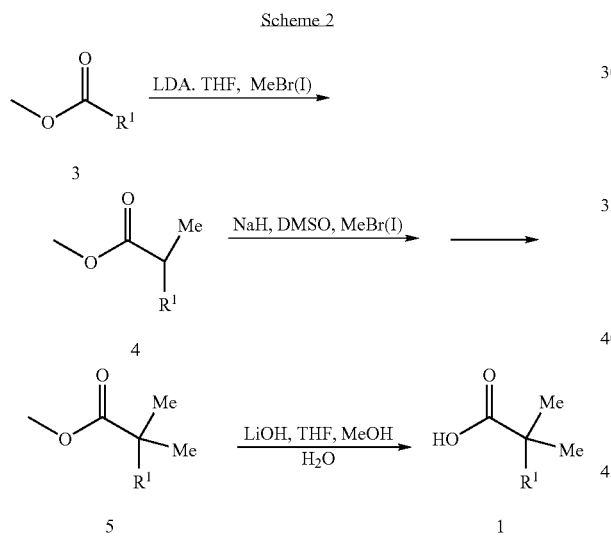

Scheme 2

A series of carboxylic acids of formula 8 can be prepared by the method outlined in Scheme 3. Alpha-substituted acetonitriles 6 can be treated with either a suitable base such as sodium hydride and excess of methyl bromide or methyl iodide in a suitable solvent such as DMF, or sequentially with two steps of methylation in suitable conditions with methyl bromide or methyl iodide, as depicted below, to provide substituted (bis)methylated carbonitriles 7. Basic hydrolysis affords the desired carboxylic acids 8.

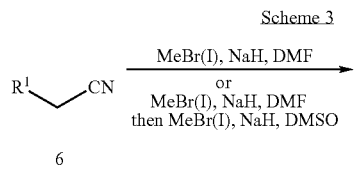

Scheme 3

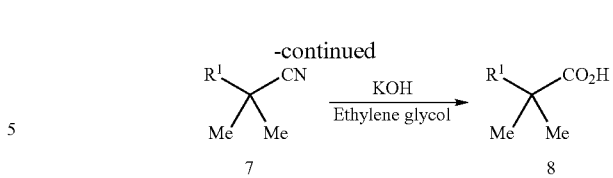

Primary amines of formula 10 (wherein Rx can be suitable substituents such as alkyl, haloalkyl, cycloalkyl or aryl; U is, e.g., $CH_2$, O, NMe, NBoc, etc., n, e.g., is 1 or 2, m is, e.g., 1 or 2) can be prepared from an appropriate cyclic ketone 9 under a variety of protocols, one of which is shown in Scheme 4. The ketone of compound 9 undergoes reductive amination with ammonium formamide to afford the amine compound 10.

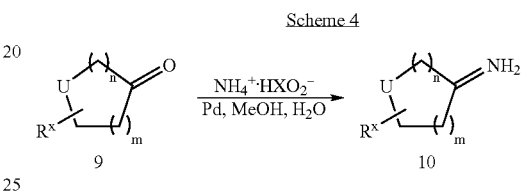

Scheme 4

Alternatively, primary amines 10 can be prepared from the appropriate alcohols 11 via mesylation, followed by conversion of the mesylates 12 to the corresponding azides 13, which upon reduction yield the desired primary amines 10, as shown in scheme 5.

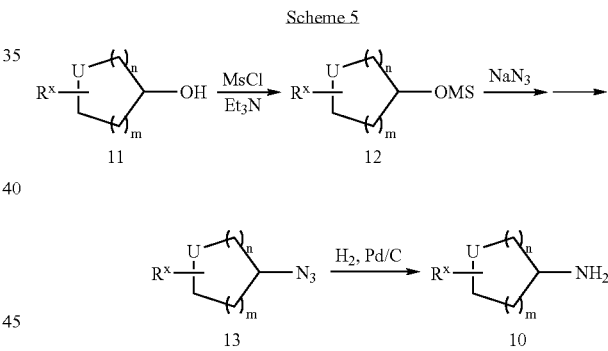

Scheme 5

Carboxamides of formula 14 can be prepared as shown in Scheme 6 (where U, $R^x$, n and m are as defined in Scheme 4) using BOP or any other suitable coupling agent.

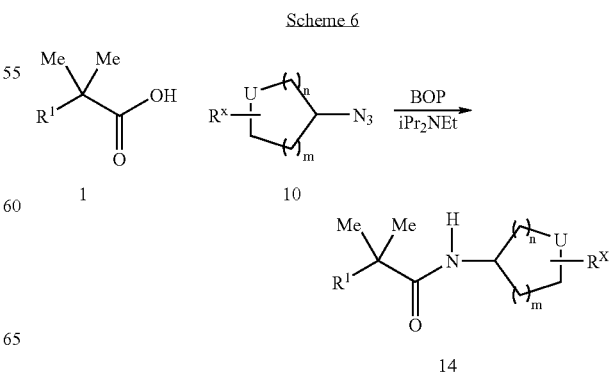

Scheme 6

Carboxamides of formula 18 can be prepared according to the method outlined in Scheme 7 (where $R^x$, n and m are as defined in Schemes 4 and 5; $R'$ is, e.g., alkyl, alkylcarbonyl, aminocarbonyl, alkylsulfonyl, alkoxycarbonyl, carbocycle, heterocycle, etc.). Coupling of carboxylic acids 1 with an appropriate primary amine 15 provides carboxamides 16. Cleavage of the N-Boc group with TFA gives 17 which can be converted by routine methods to carboxamides 18.

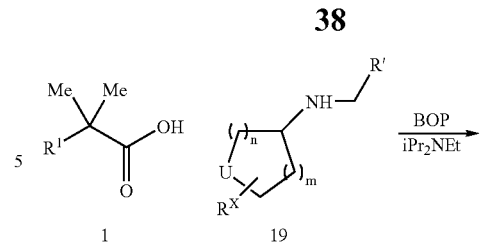

Scheme 7

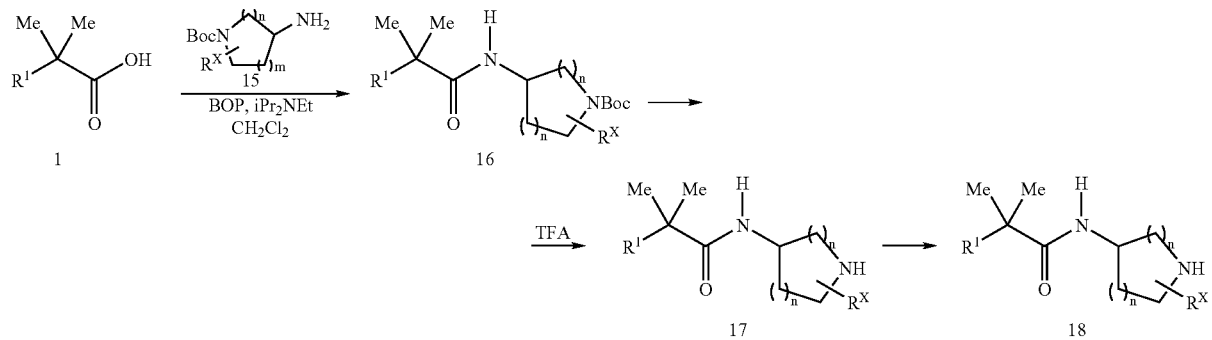

According to Scheme 8 ($R'$ is, e.g., alkyl, cycloalkyl, aryl, heteroaryl, heterocycloalkyl, arylalkyl, heteroarylalkyl, cycloalkylalkyl, heterocycloalkylalkyl, etc.; m is, e.g., 1 or 2; n is, e.g., 1 or 2), a secondary amine of formula 19 can be prepared from the reaction of an appropriate cyclic amine 10 with a suitable aldehyde R'CHO, wherein $R'$ is, e.g., alkyl, cycloalkyl, aryl, heteroaryl, heterocycloalkyl, arylalkyl, or the like.

Scheme 8

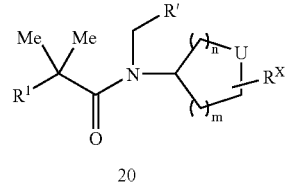

Carboxamides of formula 20 can be prepared in a standard fashion by using a suitable coupling reagent and a suitable base as shown in Scheme 9 ($R'$ is as defined in Scheme 8 and U, RX, n and m are as defined in Schemes 4 and 5).

-continued

Alternatively, carboxamides of formula 22 can be prepared following the sequence outlined in Scheme 10 (X is halo). Standard coupling of carboxylic acids 1 with an appropriate primary amine $R^2NH_2$ provides carboxamides 21 which upon alkylation with a suitable bromide or iodide $R^3X$ (wherein $R^3$ can be alkyl or cycloalkyl) can be converted to the desired compounds 22.

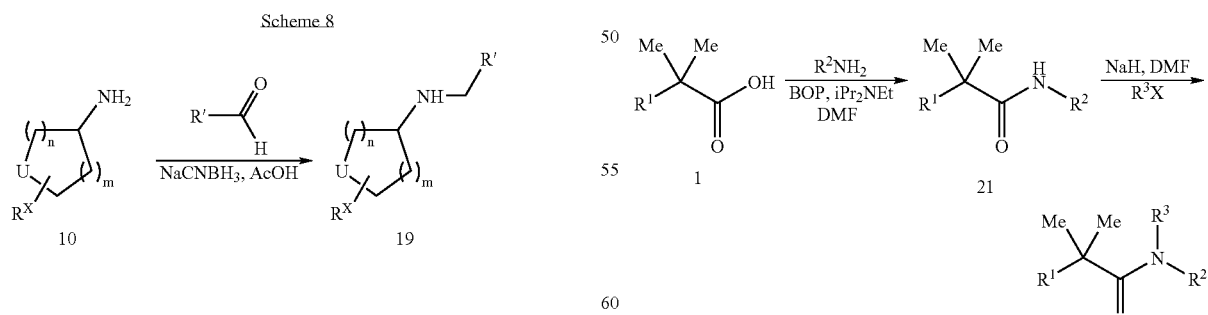

Primary amines of formula 25 and secondary amines of formula 26 can be prepared according to the method outlined in Scheme 11 (Ar is an aromatic moiety such as phenyl or pyridyl; R' is as defined in Scheme 8; and R is, e.g., alkyl, cycloalkyl, arylalkyl, etc.). A suitable bromide such as 23 can be converted to the corresponding azide 24 first, and then to the desired primary amine 25 via hydrogenation. Finally reductive amination of the appropriate aldehyde R'CHO with the primary amine 25 yields secondary amines of formula 26.

Scheme 11

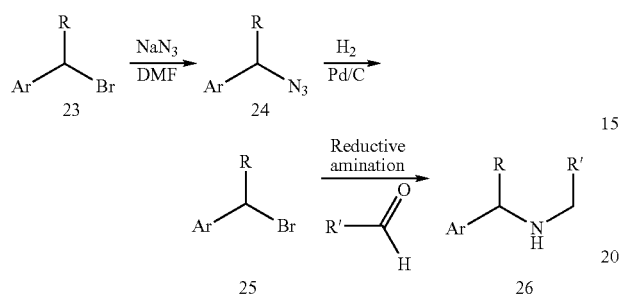

Amines of formula 32 can be prepared according to the method outlined in Scheme 12 wherein $R^{iii}$ and $R^{iv}$ are each, e.g., H, halo, alkyl, haloalkyl, alkoxy, aryl, heteroaryl, or other suitable substituents. An appropriate substituted o-hydroxycetophenones 27, available by Fries rearrangement, can react with epichlorohydrin and a suitable base to give the corresponding ethers 28. Subjecting 28 to Baeyer-Villiger oxidation provides the acetoxy intermediates 29, which can be saponified and cyclized in one step to provide alcohols 30. Oxidation of the alcohol 30 to the corresponding aldehydes 31 with TPAP and NMO, followed by reductive amination with an desired amine $R^3NH_2$ leads to the formation of compounds 32 wherein $R^3$ can be H, alkyl, cycloalkyl.

Scheme 12

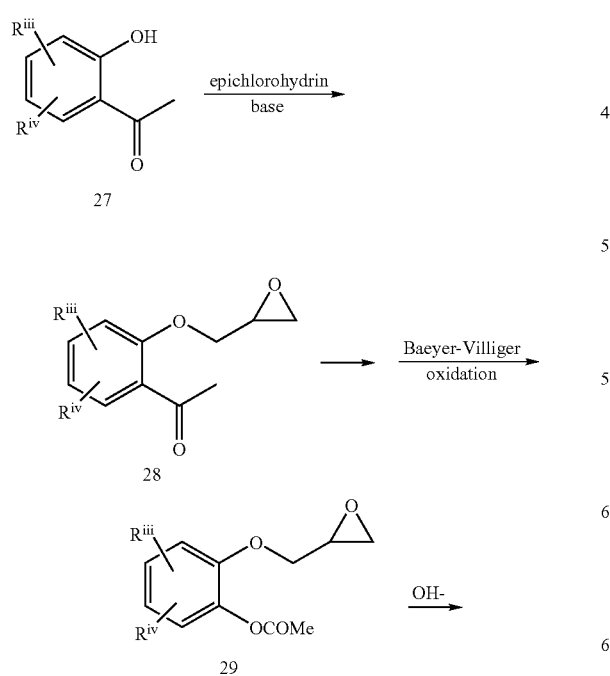

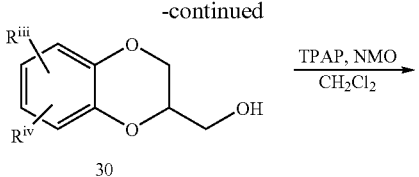

Primary amines 36 and secondary amines 37 can be prepared according to the method outlined in Scheme 13 ($R^{iii}$ and $R^{iv}$ are as defined in Scheme 12; R' is as defined in Scheme 8; $R^v$ is H, alkyl, haloalkyl, aryl, heteroaryl, etc.). Reaction of a substituted indole 33 with an Fmoc protected amino acid chloride 34, followed by cleavage of the Fmoc group with piperidine in DMF provides a ketone compound 35. Reduction of the carbonyl group of 35 with $NaBH_4$ gives a primary amine 36, which upon treatment with an appropriate aldehyde R'CHO under reductive amination conditions provides a secondary amine 37.

Scheme 13

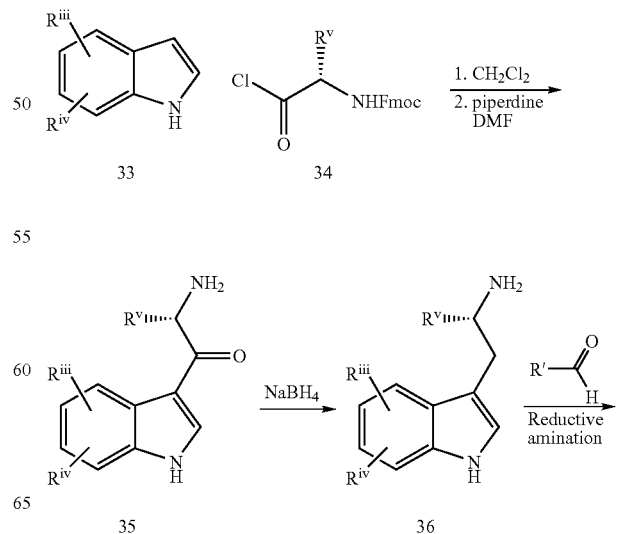

41

-continued

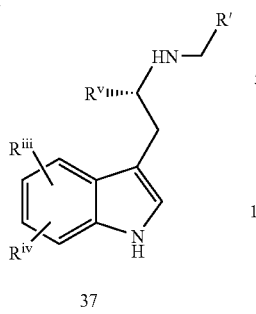

37

A series of compounds 42 can be prepared by the method outlined in Scheme 14. Compound 38 can be methylated in the standard fashion as has been described previously to give the desired bis(methylated) product 39. Both benzyl (Bn) groups of 39 can be removed by hydrogenation to give the deprotected compound 40. Treatment with a primary or secondary amines $NHR^2R^3$ ($R^2$ can be alkyl, cycloalkyl, etc.; and $R^3$ can be H, alkyl, cycloalkyl, etc) can provide amides of formula 41. The free hydroxyl group of 41 can be converted to a variety of ether analogs 42 by routine methods wherein R can be alkyl, aryl, cycloalkyl, arylalkyl or other suitable groups.

Scheme 14

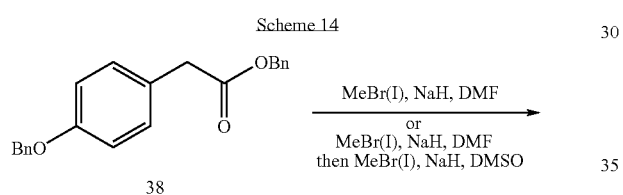

38

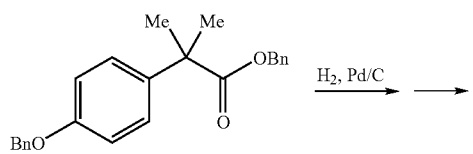

39

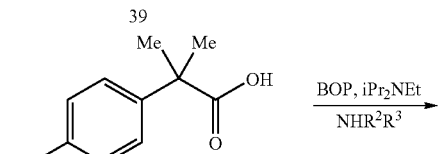

40

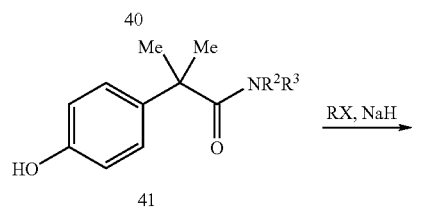

41

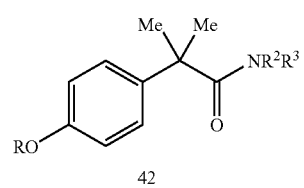

42

42

A series of compounds 44 can be prepared by the method outlined in Scheme 15 (Ar is aryl, heteroaryl or a derivative thereof). Phenols 41 can be converted to the corresponding triflates 43 which then can undergo Pd catalyzed Suzuki coupling to provide compounds 44 wherein $R^2$ can be alkyl, cycloalkyl or the like and $R^3$ can be H, alkyl, cycloalkyl.

Scheme 15

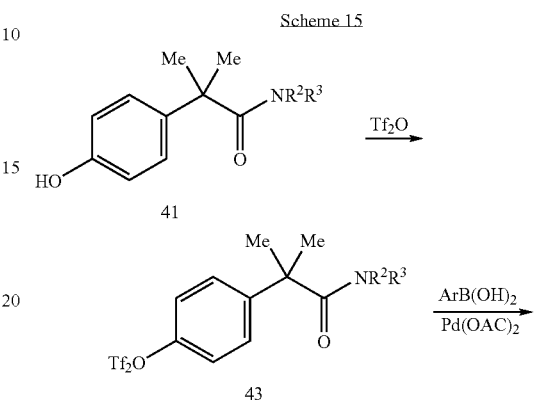

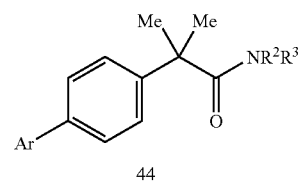

44

A series of compounds 45 can be prepared by the method outlined in Scheme 16 (Ar can be, for example, aryl or heteroaryl or derivatives thereof). The free phenol group of 41 can be coupled with $ArB(OH)_2$ directly to provide the aryl or heteroaryl ether coupling product 45 wherein $R^2$ can be alkyl, cycloalkyl or the like and $R^3$ can be H, alkyl, cycloalkyl.

Scheme 16

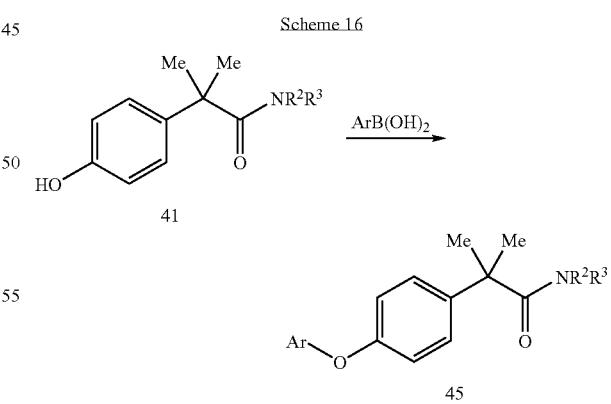

A series of 4-heterocycloalkyl- or heterocylcoalkylalkyl-ether compounds 46 and 47 can be prepared by the method outlined in Scheme 17. The free phenol of 41 can be treated with a variety of heterocycloalkyl triflates or heterocycloalkylalkyl halides to provide heterocycloalkyl- or heterocylcoalkylalkyl-ether compounds 46 and 47.

Scheme 17

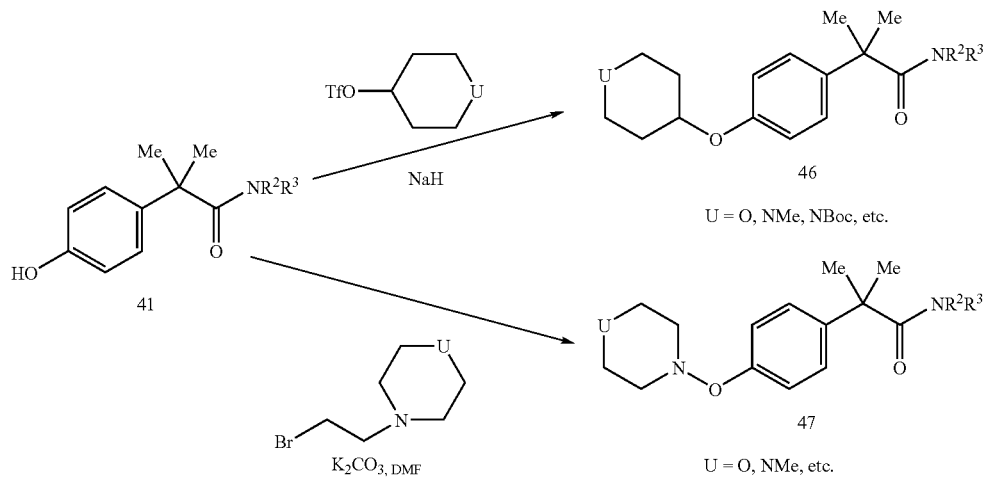

A series of carboxamides of formula 48 are prepared by the method outlined in Scheme 18 (L is, e.g., —(CH$_2$)$_m$—O— or —(CH$_2$)$_m$—S—; m is, e.g., 0, 1, or 2; Cy$^1$ is, e.g., aryl, heteroaryl, cycloalkyl, heterocycloalkyl, or derivatives thereof). Carboxylic acids of formula 1a can be coupled to an amine NHR$^2$R$^3$ using a suitable coupling reagent such as BOP to provide the desired compounds 48 wherein R$^2$ can be alkyl, cycloalkyl or the like and R$^3$ can be H, alkyl, cycloalkyl.

Scheme 18

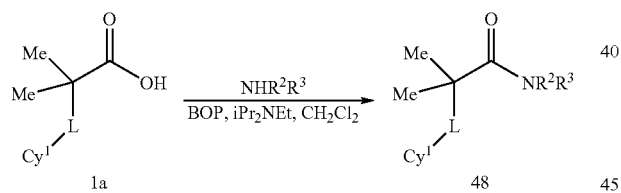

As shown in Scheme 19, a series of carboxylic acids of formula 52 can be prepared according to the method outlined, wherein L$^1$ is S or O and R can be aryl, arylalkyl, heteroaryl, heteroarylalkyl, cycloalkyl, cycloalkylalyl, heterocycloalkyl, heterocycloalkylakyl or derivative thereof. Reaction of an appropriate thiol or alcohol 49 with methyl bromoacetate in the presence of a suitable base such as potassium or sodium carbonate, triethylamine or sodium hydride in a solvent such as tetrahydrofuran, acetonitrile or dichloromethane provides thioethers or ethers 50. Treatment of 50 with excess of methyl bromide or methyl iodide in the presence of a suitable base such as sodium hydride or LDA and in a suitable solvent such as DMF or THF provides methyl esters 51, which upon basic hydrolysis yield the desired carboxylic acids 52.

Scheme 19

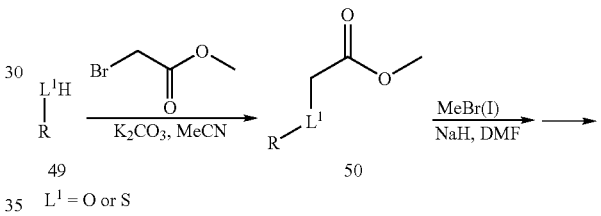

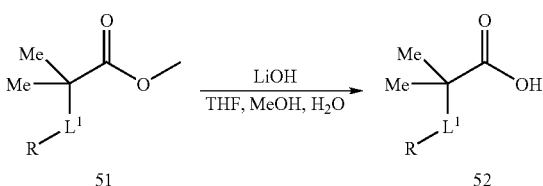

The di-methylation steps can take place sequentially as shown in Scheme 20 (R can be, e.g., aryl, arylalkyl, heteroaryl, heteroarylalkyl, cycloalkyl, cycloalkylalyl, heterocycloalkyl, heterocycloalkylakyl or derivatives thereof). Methylation of ethers or thioethers 50 with one equivalent of methyl bromide or methyl iodide in the presence of a suitable base such as NaH, LDA or LiHMDS in a suitable solvent such as DMF or THF, followed by a second alkylation with MeBr (I) in the presence of a base such as NaH and in a solvent such as DMSO provides di-methylated esters 53, which upon basic hydrolysis yield the desired carboxylic acids 54.

-continued

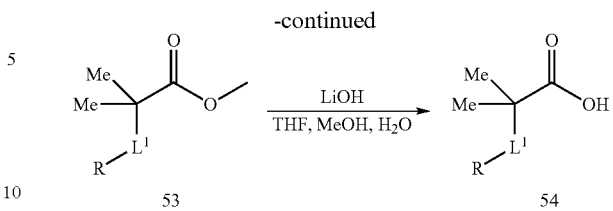

Scheme 20

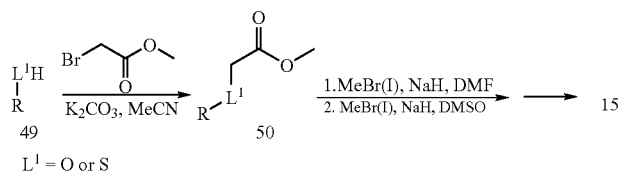

Alternatively, starting with an appropriate cyclo-ketone or cyclo-thioketone 55 (wherein the ring can be carbocyclic or heterocyclic) and following Scheme 21, a series of carboxylic acids of formula 58 wherein the ring is aromatic or non-aromatic can be prepared.

Scheme 21

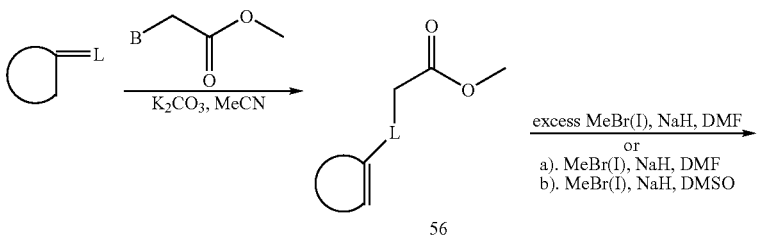

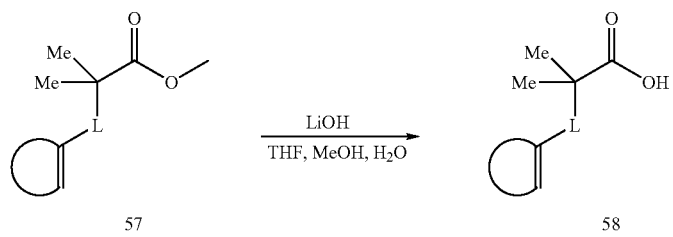

A series of carboxylic acids of formula 63 wherein $L^1$ is O or S can be prepared by the method outlined in Scheme 22. O- or S-alkylation of compounds 59 with a suitable chloride or bromide provides methyl esters 60. Methylation of the ester 60 with methyl bromide or methyl iodide in the presence of LDA yields mono-methylated esters 61, which can undergo a second methylation with another methyl bromide or methyl iodide in the presence of NaH and in DMSO to provide the corresponding di-methylated esters 62. Finally, basic hydrolysis yields the desired carboxylic acids 63 wherein $Cy^1$ is a cyclic moiety such as aryl or heteroaryl.

-continued

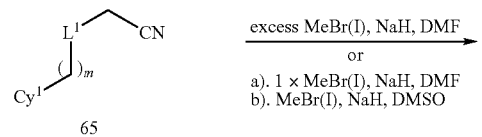

Scheme 21

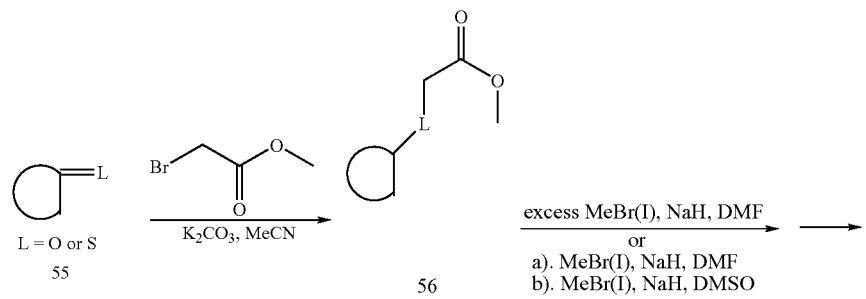

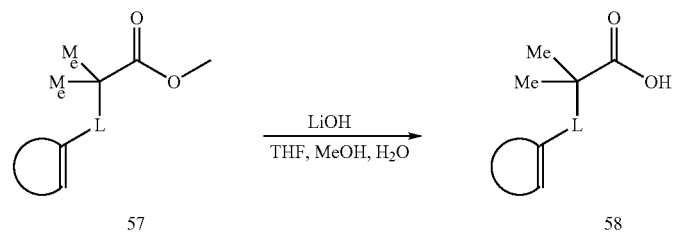

Alternatively, a series of carboxylic acids of formula 67, wherein $L^1$ is O or S and m is 1 or 2, can be prepared according to Scheme 23. Reaction of an appropriate alcohol or thiol 64 wherein $Cy^1$ is a cyclic moiety such as aryl or heteroaryl with chloroacetonitrile in the presence of sodium ethoxide under refluxing conditions provides nitriles 65. Methylation(s) of 65 in the standard fashion as depicted in Scheme 23 provides nitriles 66, which upon basic hydrolysis provide the desired carboxylic acids 67.

-continued

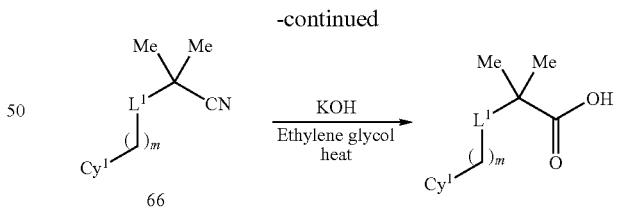

Scheme 23

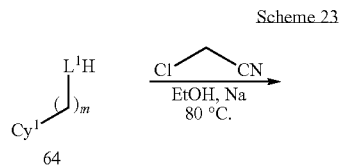

According to Scheme 24, alternatively, especially when $Cy^1$ is heteroaryl, carboxylic acids 73 can be prepared by the reaction of an appropriate alcohol $Cy^1CH_2OH$ with thioglycolic acid 68 in the presence of a Lewis acid such as zinc trifluoromethanesulfonate, under refluxing conditions. Then 69 can be processed to the desired carboxylic acids 73 in the standard fashion as shown in Scheme 24. Di-methylation of the α-position to the carbonyl can be accomplished either in 2 steps as shown in Scheme 24 or in one step as shown in Scheme 21.

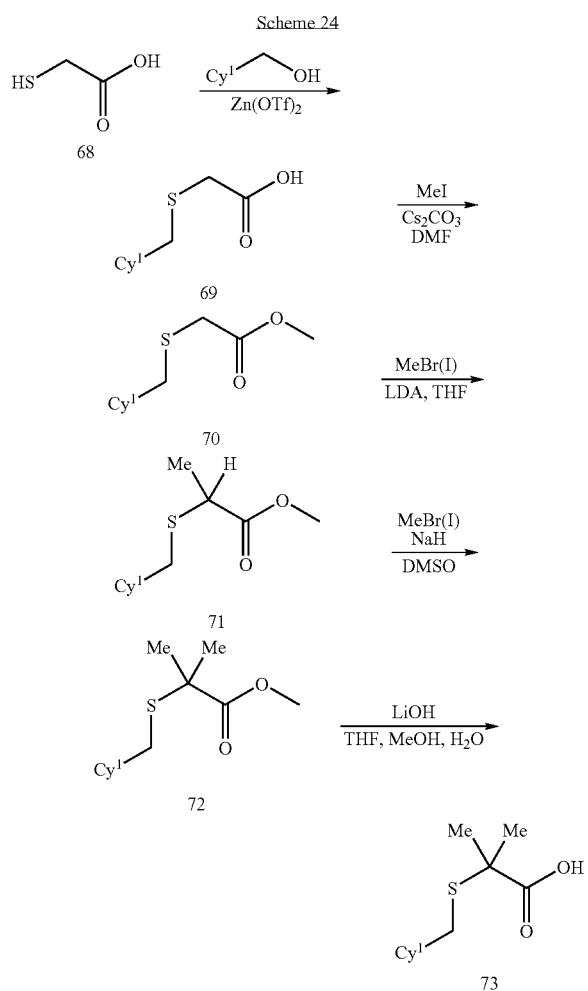

Scheme 24

Methods

Compounds of the invention can modulate activity of 11βHSD1 and/or MR. The term "modulate" is meant to refer to an ability to increase or decrease activity of an enzyme or receptor. Accordingly, compounds of the invention can be used in methods of modulating 11βHSD1 and/or MR by contacting the enzyme or receptor with any one or more of the compounds or compositions described herein. In some embodiments, compounds of the present invention can act as inhibitors of 11βHSD1 and/or MR. In further embodiments, the compounds of the invention can be used to modulate activity of 11βHSD1 and/or MR in an individual in need of modulation of the enzyme or receptor by administering a modulating amount of a compound of the invention.

The present invention further provides methods of inhibiting the conversion of cortisone to cortisol in a cell, or inhibiting the production of cortisol in a cell, where conversion to or production of cortisol is mediated, at least in part, by 11βHSD1 activity. Methods of measuring conversion rates of cortisone to cortisol and vice versa, as well as methods for measuring levels of cortisone and cortisol in cells, are routine in the art.

The present invention further provides methods of increasing insulin sensitivity of a cell by contacting the cell with a compound of the invention. Methods of measuring insulin sensitivity are routine in the art.

The present invention further provides methods of treating disease associated with activity or expression, including abnormal activity and overexpression, of 11βHSD1 and/or MR in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the enzyme or receptor. An 11βHSD1-associated disease can also include any disease, disorder or condition that can be prevented, ameliorated, or cured by modulating enzyme activity.

Examples of 11βHSD1-associated diseases include obesity, diabetes, glucose intolerance, insulin resistance, hyperglycemia, hypertension, hyperlipidemia, cognitive impairment, dementia, glaucoma, cardiovascular disorders, osteoporosis, and inflammation. Further examples of 11βHSD1-associated diseases include metabolic syndrome, type 2 diabetes, androgen excess (hirsutism, menstrual irregularity, hyperandrogenism) and polycystic ovary syndrome (PCOS).

The present invention further provides methods of modulating MR activity by contacting the MR with a compound of the invention, pharmaceutically acceptable salt, prodrug, or composition thereof. In some embodiments, the modulation can be inhibition. In further embodiments, methods of inhibiting aldosterone binding to the MR (optionally in a cell) are provided. Methods of measuring MR activity and inhibition of aldosterone binding are routine in the art.

The present invention further provides methods of treating a disease associated with activity or expression of the MR. Examples of diseases associated with activity or expression of the MR include, but are not limited to hypertension, as well as cardiovascular, renal, and inflammatory pathologies such as heart failure, atherosclerosis, arteriosclerosis, coronary artery disease, thrombosis, angina, peripheral vascular disease, vascular wall damage, stroke, dyslipidemia, hyperlipoproteinaemia, diabetic dyslipidemia, mixed dyslipidemia, hypercholesterolemia, hypertriglyceridemia, and those associated with type 1 diabetes, type 2 diabetes, obesity metabolic syndrome, insulin resistance and general aldosterone-related target organ damage.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or cell comprising the eye.

As used herein, the term "contacting" refers to the bringing together of indicated moieties in an in vitro system or an in vivo system. For example, "contacting" the 11βHSD1 enzyme with a compound of the invention includes the administration of a compound of the present invention to an individual or patient, such as a human, having 11βHSD1, as well as, for example, introducing a compound of the invention into a sample containing a cellular or purified preparation containing the 11βHSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease (non-limiting examples are preventing metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS);

(2) inhibiting the disease; for example, inhibiting a disease, condition or disorder in an individual who is experiencing or displaying the pathology or symptomatology of the disease, condition or disorder (i.e., arresting further development of the pathology and/or symptomatology) such as inhibiting the development of metabolic syndrome, hypertension, obesity, insulin resistance, hyperglycemia, hyperlipidemia, type 2 diabetes, androgen excess (hirsutism, menstrual irregularity, hyperandrogenism) or polycystic ovary syndrome (PCOS), stabilizing viral load in the case of a viral infection; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS), or lowering viral load in the case of a viral infection.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, antibodies, immune suppressants, anti-inflammatory agents and the like.

Labeled Compounds and Assay Methods

Another aspect of the present invention relates to radiolabeled compounds of the invention that would be useful not only in radio-imaging but also in assays, both in vitro and in vivo, for localizing and quantitating the enzyme in tissue samples, including human, and for identifying ligands by inhibition binding of a radio-labeled compound. Accordingly, the present invention includes enzyme assays that contain such radio-labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro receptor labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the enzyme. Accordingly, the ability of a test compound to compete with the radio-labeled compound for binding to the enzyme directly correlates to its binding affinity.

Kits

The present invention also includes pharmaceutical kits useful, for example, in the treatment or prevention of 11βHSD1-associated diseases or disorders, obesity, diabetes

EXAMPLES

Example 1

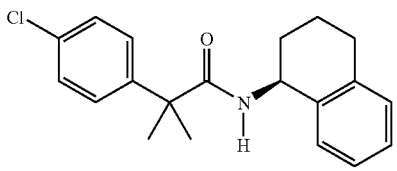

2-(4-chlorophenyl)-N-Cyclohexyl-2-methylpropanamide

BOP (200 μL, 0.25 M in DMF, 50 μmol) was added to a solution of 2-(4-chlorophenyl)-2-methylpropanoic acid (200 μL, 0.25 M in DMF, 50 μmol) at RT, followed by addition of N-methyl morpholine (40 μL). The mixture was stirred at RT for 15 min, then a solution of cyclohexylamine in DMF (200 μL, 0.25 M in DMF, 50 μmol) was added. The resulting mixture was stirred at RT for 3 h, and then was adjusted by TFA to PH=2.0, and diluted with DMSO (1100 μL). The resulting solution was purified by prep.-HPLC to afford the desired product 2-(4-chlorophenyl)-N-cyclohexyl-2-methylpropanamide. LCMS: (M+H)$^+$=280.0/282.0.

Example 2

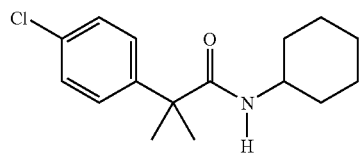

2-(4-Chlorophenyl)-2-methyl-N-[(1S)-1,2,3,4-tetrahydronaphthalen-1-yl]propanamide This compound was prepared using procedures analogous to those for example 1. LCMS: (M+H)$^+$=328.0/330.0.

Example 3

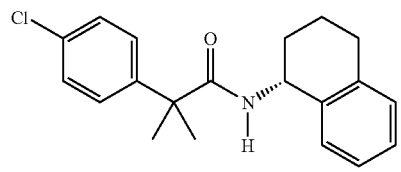

2-(4-Chlorophenyl)-2-methyl-N-[(1R)-1,2,3,4-tetrahydronaphthalen-1-yl]propanamide This compound was prepared using procedures analogous to those for example 1. LCMS: (M+H)$^+$=328.0/330.0.

Example 4

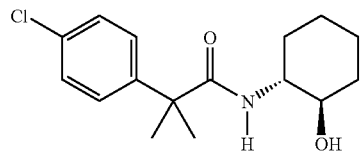

2-(4-Chlorophenyl)-N-[(1R,2R)-2-(benzyloxy)cyclohexyl]-2-methylpropanamide

This compound was prepared using procedures analogous to those for example 1. LCMS: (M+H)$^+$=296.0/298.0.

Example 5

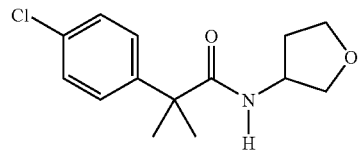

2-(4-Chlorophenyl)-2-methyl-N-(tetrahydrofuran-3-yl)propanamide

This compound was prepared using procedures analogous to those for example 1. LCMS: (M+H)$^+$=268.0/270.0.

Example 6

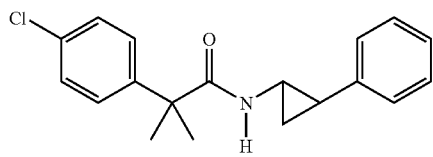

2-(4-Chlorophenyl)-2-methyl-N-(2-phenylcyclopropyl)propanamide

This compound was prepared using procedures analogous to those for example 1. LCMS: (M+H)$^+$=314.0/316.0.

Example 7

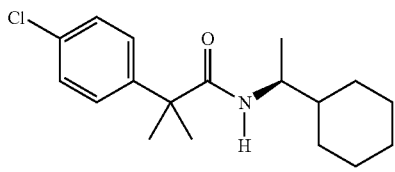

2-(4-Chlorophenyl)-N-[(1S)-1-cyclohexylethyl]-2-methylpropanamide

This compound was prepared using procedures analogous to those for example 1. LCMS: (M+H)$^+$=308.1/310.1.

Example 8

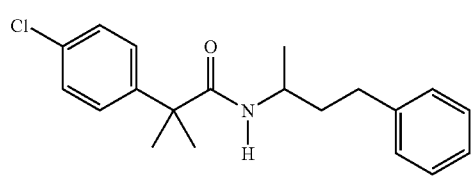

2-(4-Chlorophenyl)-N-(1-methyl-3-phenylpropyl)-2-methylpropanamide

This compound was prepared using procedures analogous to those for example 1. LCMS: (M+H)$^+$=330.0/332.0.

Example 9

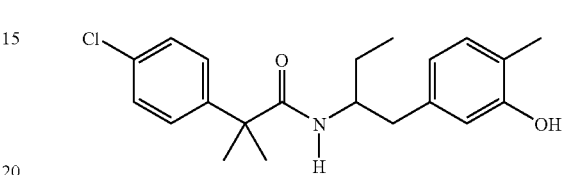

2-(4-Chlorophenyl)-N-[1-(3-hydroxy-4-methylbenzyl)propyl]-2-methylpropanamide

This compound was prepared using procedures analogous to those for example 1. LCMS: (M+H)$^+$=360.1/362.1.

Example 10

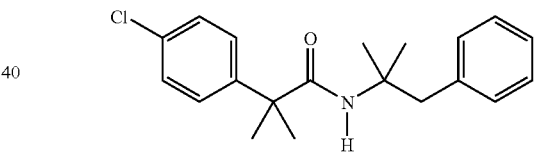

2-(4-Chlorophenyl)-N-(1,1-dimethyl-2-phenylethyl)-2-methylpropanamide

This compound was prepared using procedures analogous to those for example 1. LCMS: (M+H)$^+$=330.0/332.0.

Example 11

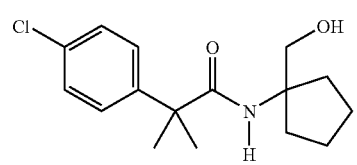

2-(4-Chlorophenyl)-N-[1-(hydroxymethyl)cyclopentyl]-2-methylpropanamide

This compound was prepared using procedures analogous to those for example 1. LCMS: (M+H)$^+$=296.0/298.0.

Example 12

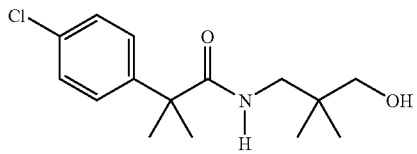

2-(4-Chlorophenyl)-N-(3-hydroxy-2,2-dimethylpropyl)-2-methylpropanamide

This compound was prepared using procedures analogous to those for example 1. LCMS: (M+H)$^+$=284.0/286.0.

Example 13

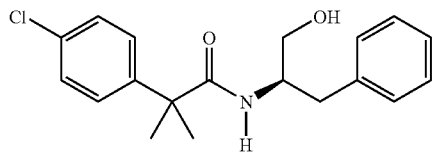

N-[(1R)-1-Benzyl-2-hydroxyethyl]-2-(4-chlorophenyl)-2-methylpropanamide

This compound was prepared using procedures analogous to those for example 1. LCMS: (M+H)$^+$=332.0/334.0.

Example 14

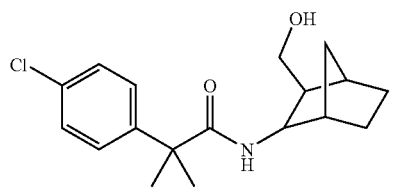

2-(4-Chlorophenyl)-N-[3-(hydroxymethyl)bicyclo[2.2.1]hept-2-yl]-2-methylpropanamide This compound was prepared using procedures analogous to those for example 1. LCMS: (M+H)$^+$=322.0/324.0.

Example 15

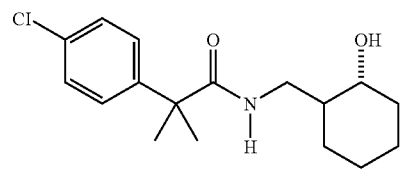

2-(4-Chlorophenyl)-N-{[(trans)-2-hydroxycyclohexyl]methyl}-2-methylpropanamide

This compound was prepared using procedures analogous to those for example 1. LCMS: (M+H)$^+$=310.1/312.0.

Example 16

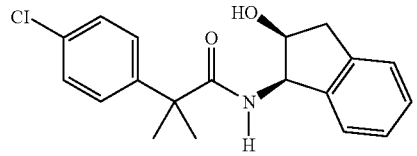

2-(4-Chlorophenyl)-N-[(1R,2S)-2-hydroxy-2,3-dihydro-1H-inden-1-yl]-2-methylpropanamide This compound was prepared using procedures analogous to those for example 1. LCMS: (M+H)$^+$=330.0/332.0.

Example 17

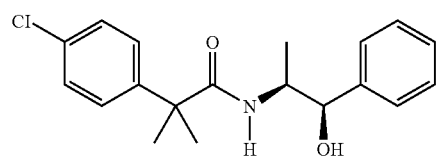

2-(4-Chlorophenyl)-N-[(1S,2R)-2-hydroxy-1-methyl-2-phenylethyl]-2-methylpropanamide This compound was prepared using procedures analogous to those for example 1. LCMS: (M+H)$^+$=332.0/334.0; (M−H$_2$O+H)$^+$=314.0/316.0.

Example 18

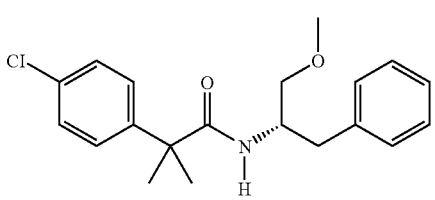

N-[(1S)-1-Benzyl-2-methoxyethyl]-2-(4-chlorophenyl)-2-methylpropanamide

This compound was prepared using procedures analogous to those for example 1. LCMS: (M+H)$^+$=346.0/348.0.

Example 19

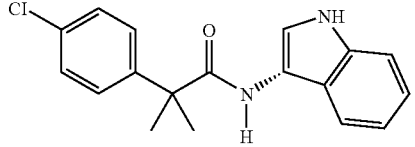

2-(4-Chlorophenyl)-N-[(1S)-2-hydroxy-1-(1H-indol-3-ylmethyl)ethyl]-2-methyl propanamide This compound was prepared using procedures analogous to those for example 1. LCMS: (M+H)$^+$=371.1/373.1.

Example 20

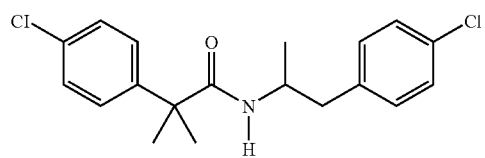

2-(4-Chlorophenyl)-N-[2-(4-chlorophenyl)-1-methylethyl]-2-methyl-2-propanamide

This compound was prepared using procedures analogous to those for example 1. LCMS: (M+H)$^+$=350.0/352.0.

Example 21

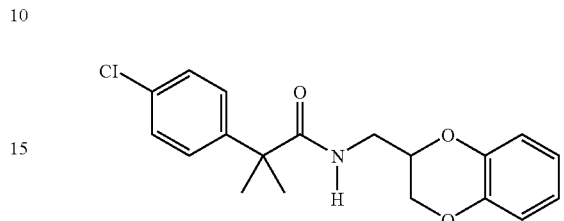

2-(4-Chlorophenyl)-N-(2,3-dihydro-1,4-benzodioxin-2-ylmethyl)-2-methylpropanamide This compound was prepared using procedures analogous to those for example 1. LCMS: (M+H)$^+$=346.0/348.0.

Example 22

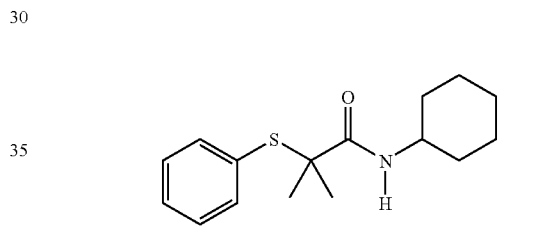

N-Cyclohexyl-2-methyl-2-(phenylthio)propanamide

Step 1. Methyl 2-methyl-2-(phenylthio)propanoate

Sodium hydride (60% in mineral oil, 1.08 g, 27.1 mmol) was suspended in DMF (20 mL) and cooled to 0° C. A solution of methyl(phenylthio)acetate (2.15 g, 11.8 mmol) in THF (40 mL) was added via cannula at 0° C. After stirring for 10 min at 0° C., methyl iodide (3.67 mL, 59.0 mmol) was added dropwise at 0° C. The reaction mixture was stirred at rt overnight. It was quenched by the addition of water and EtOAc. After stirring for a few min to dissolve all solids, the layers were separated. The organic layer was dried over MgSO$_4$, filtered and concentrated. The residue was flash chromatographed (silica, hexanes:ether, 2:1) to provide the desired product (2.25 g, 90.7% yield).

Step 2. 2-Methyl-2-(phenylthio)propanoic acid

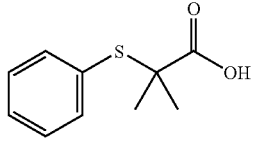

Methyl 2-methyl-2-(phenylthio)propanoate (1.126 g, 5.35 mmol) was dissolved in THF (15 mL) and methanol (5 mL). That solution was treated with an aqueous solution of lithium hydroxide monohydrate (1.12 g, 26.8 mmol in 5 mL of water). The reaction mixture was stirred at rt overnight. The volatiles were removed and the remaining aqueous solution was acidified with a 1 N HCl solution to pH 2. Ethyl acetate was added and the layers were separated. The organic layer was dried over MgSO$_4$, filtered and concentrated to provide the desired carboxylic acid as a white solid (1.020 g, 97.1% yield).

Step 3.

2-Methyl-2-(phenylthio)propanoic acid was converted to the final compound using procedures analogous to those for example 1. LCMS: (M+H)$^+$=278.0.

Example 23

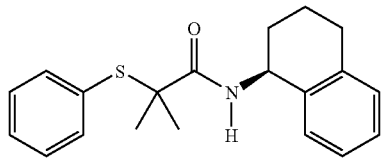

2-Methyl-2-(phenylthio)-N-[(1S)-1,2,3,4-tetrahydronaphthalen-1-yl]propanamide

This compound was prepared using procedures analogous to those for example 22. LCMS: (M+H)$^+$=326.0.

Example 24

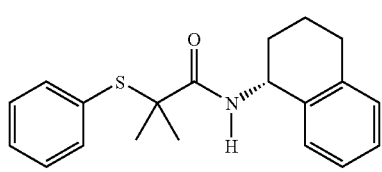

2-Methyl-2-(phenylthio)-N-[(1R)-1,2,3,4-tetrahydronaphthalen-1-yl]propanamide

This compound was prepared using procedures analogous to those for example 22. LCMS: (M+H)$^+$=326.0.

Example 25

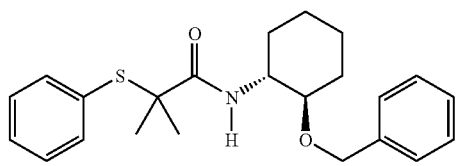

N-[(1R,2R)-2-(Benzyloxy)cyclohexyl]-2-methyl-2-(phenylthio)propanamide

This compound was prepared using procedures analogous to those for example 22. LCMS: (M+H)$^+$=384.1.0.

Example 26

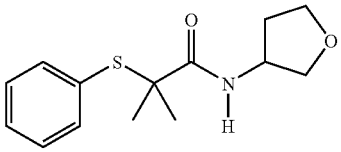

2-Methyl-2-(phenylthio)-N-(tetrahydrofuran-3-yl)propanamide

This compound was prepared using procedures analogous to those for example 22. LCMS: (M+H)$^+$=266.0.

Example 27

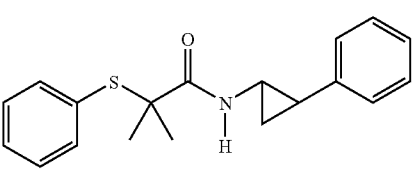

2-Methyl-N-(2-phenylcyclopropyl)-2-(phenylthio)propanamide

This compound was prepared using procedures analogous to those for example 22. LCMS: (M+H)$^+$=312.0.

Example 28

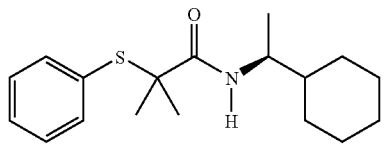

N-[(1S)-1-Cyclohexylethyl]-2-methyl-2-(phenylthio)propanamide

This compound was prepared using procedures analogous to those for example 22. LCMS: (M+H)$^+$=306.1.

Example 29

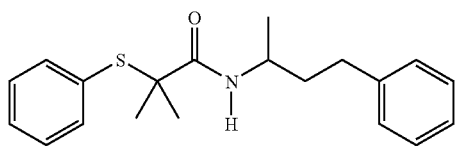

N-(1-Methyl-3-phenylpropyl)-2-methyl-2-(phenylthio)propanamide

This compound was prepared using procedures analogous to those for example 22. LCMS: (M+H)$^+$=328.0.

Example 30

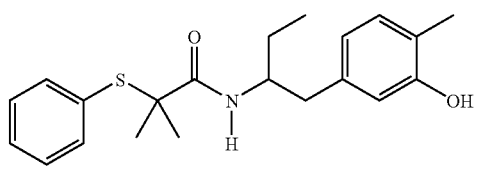

N-[1-(3-Hydroxy-4-methylbenzyl)propyl]-2-methyl-2-(phenylthio)propanamide

This compound was prepared using procedures analogous to those for example 22. LCMS: (M+H)$^+$=358.1.

Example 31

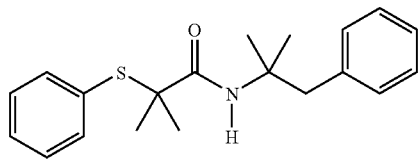

N-(1,1-Dimethyl-2-phenylethyl)-2-methyl-2-(phenylthio)propanamide

This compound was prepared using procedures analogous to those for example 22. LCMS: (M+H)$^+$=328.0.

Example 32

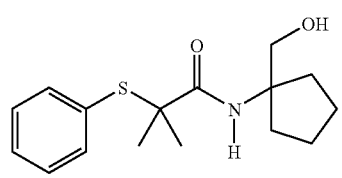

N-[1-(Hydroxymethyl)cyclopentyl]-2-methyl-2-(phenylthio)propanamide

This compound was prepared using procedures analogous to those for example 22. LCMS: (M+H)$^+$=294.0.

Example 33

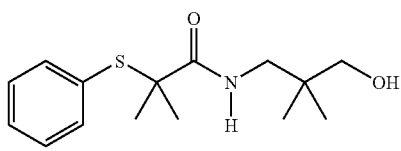

N-(3-Hydroxy-2,2-dimethylpropyl)-2-methyl-2-(phenylthio)propanamide

This compound was prepared using procedures analogous to those for example 22. LCMS: (M+H)$^+$=282.0.

Example 34

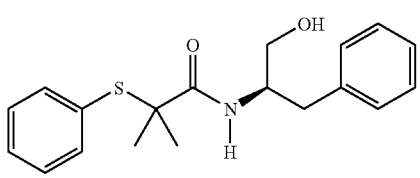

N-[(1R)-1-Benzyl-2-hydroxyethyl]-2-methyl-2-(phenylthio)propanamide

This compound was prepared using procedures analogous to those for example 22. LCMS: (M+H)⁺=330.0.

Example 35

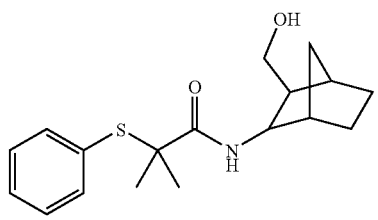

N-[3-(Hydroxymethyl)bicyclo[2.2.1]hept-2-yl]-2-methyl-2-(phenylthio)propanamide

This compound was prepared using procedures analogous to those for example 22. LCMS: (M+H)⁺=320.1.

Example 36

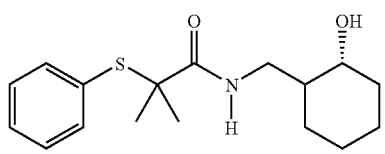

N-{[(trans)-2-Hydroxycyclohexyl]methyl}-2-methyl-2-(phenylthio)propanamide

This compound was prepared using procedures analogous to those for example 22. LCMS: (M+H)⁺=308.0.

Example 37

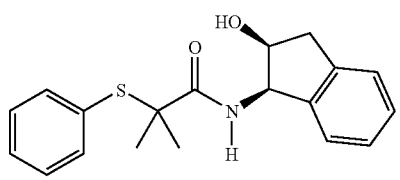

N-[(1R,2S)-2-Hydroxy-2,3-dihydro-1H-inden-1-yl]-2-methyl-2-(phenylthio)propanamide This compound was prepared using procedures analogous to those for example 22. LCMS: (M+H)⁺=328.0.

Example 38

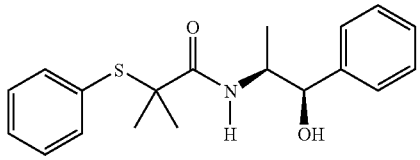

N-[(1S,2R)-2-Hydroxy-1-methyl-2-phenylethyl]-2-methyl-2-(phenylthio)propanamide

This compound was prepared using procedures analogous to those for example 22. LCMS: (M+H)⁺=330.0; (M−H₂O+H)⁺=312.0.

Example 39

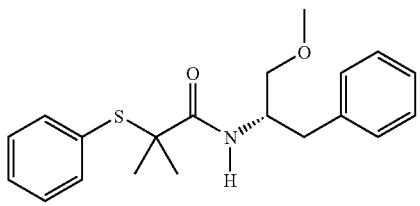

N-[(1S)-1-Benzyl-2-methoxyethyl]-2-methyl-2-(phenylthio)propanamide

This compound was prepared using procedures analogous to those for example 22. LCMS: M+H)⁺=344.1.

Example 40

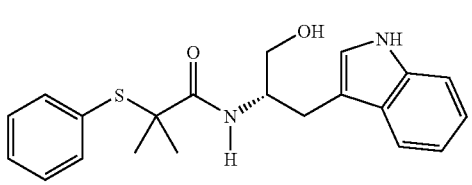

69

N-[(1S)-2-Hydroxy-1-(1H-indol-3-ylmethyl)ethyl]-2-methyl-2-(phenylthio)propanamide This compound was prepared using procedures analogous to those for example 22. LCMS: (M+H)$^+$=369.1.

Example 41

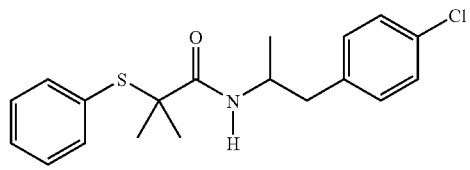

N-[2-(4-Chlorophenyl)-1-methylethyl]-2-methyl-2-(phenylthio)propanamide

This compound was prepared using procedures analogous to those for example 22. LCMS: (M+H)$^+$=348.0/350.0.

Example 42

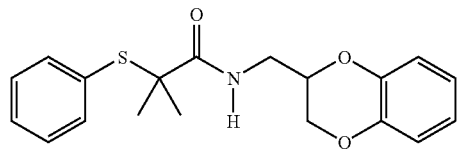

N-(2,3-Dihydro-1,4-benzodioxin-2-ylmethyl)-2-methyl-2-(phenylthio)propanamide

This compound was prepared using procedures analogous to those for example 22. LCMS: (M+H)$^+$=344.0.

Example 43

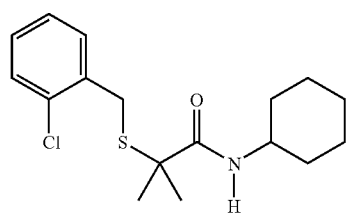

70

2-[2-Chlorobenzyl)thio]-N-Cyclohexyl-2-methylpropanamide

This compound was prepared using procedures analogous to those for example 22. LCMS: (M+H)$^+$=326.0/328.0.

Example 44

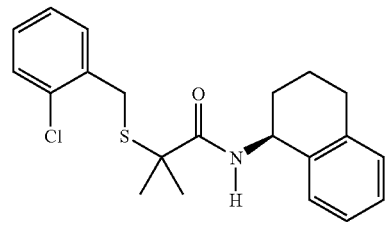

2-[(2-Chlorobenzyl)thio]-2-methyl-N-[(1S)-1,2,3,4-tetrahydronaphthalen-1-yl]propanamide This compound was prepared using procedures analogous to those for example 22. LCMS: (M+H)$^+$=374.0/376.0.

Example 45

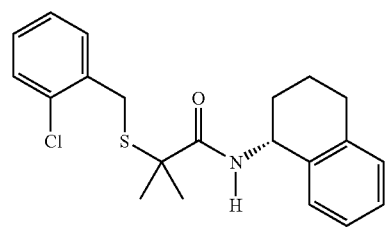

2-[(2-Chlorobenzyl)thio]-2-methyl-N-[(1R)-1,2,3,4-tetrahydronaphthalen-1-yl]propanamide This compound was prepared using procedures analogous to those for example 22. LCMS: (M+H)$^+$=374.0/376.0.

Example 46

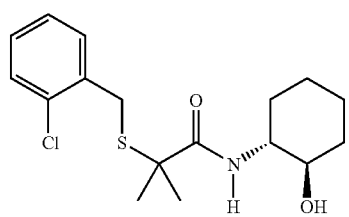

71

2-[(2-Chlorobenzyl)thio]-N-[(1R,2R)-2-(benzyloxy)cyclohexyl]-2-methylpropanamide This compound was prepared using procedures analogous to those for example 22. LCMS: (M+H)$^+$=342.0/344.1.

Example 47

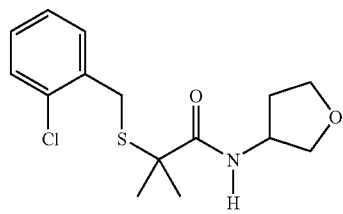

2-[(2-Chlorobenzyl)thio]-2-methyl-N-(tetrahydrofuran-3-yl)propanamide

This compound was prepared using procedures analogous to those for example 22. LCMS: (M+H)$^+$=314.0/316.0.

Example 48

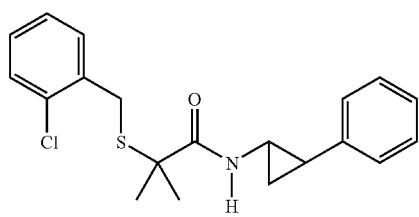

2-[(2-Chlorobenzyl)thio]-2-methyl-N-(2-phenylcyclopropyl)propanamide

This compound was prepared using procedures analogous to those for example 22. LCMS: (M+H)$^+$=360.0/362.0.

Example 49

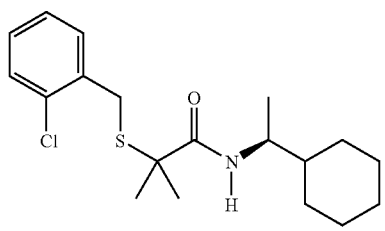

72

2-[(2-Chlorobenzyl)thio]-N-[(1S)-1-cyclohexylethyl]-2-methylpropanamide

This compound was prepared using procedures analogous to those for example 22. LCMS: (M+H)$^+$=354.1/356.1.

Example 50

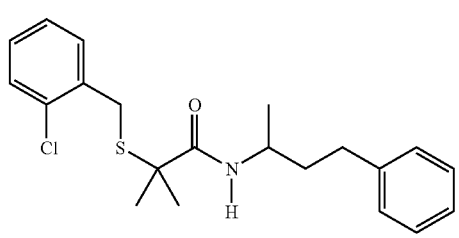

2-[(2-Chlorobenzyl)thio]-N-(1-methyl-3-phenylpropyl)-2-methylpropanamide

This compound was prepared using procedures analogous to those for example 22. LCMS: (M+H)$^+$=376.0/378.0.

Example 51

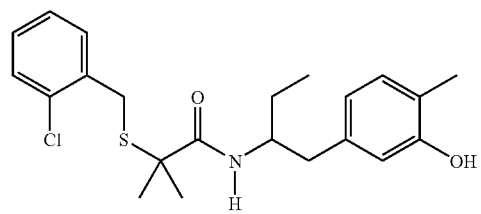

2-[(2-Chlorobenzyl)thio]-N-[1-(3-hydroxy-4-methylbenzyl)propyl]-2-methylpropanamide This compound was prepared using procedures analogous to those for example 22. LCMS: (M+14)$^+$=406.1/408.0.

Example 52

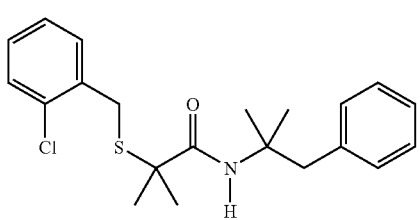

Example 53

2-[(2-Chlorobenzyl)thio]-N-(1,1-dimethyl-2-phenyl-ethyl)-2-methylpropanamide

This compound was prepared using procedures analogous to those for example 22. LCMS: (M+H)⁺=376.0/378.0.

Example 54

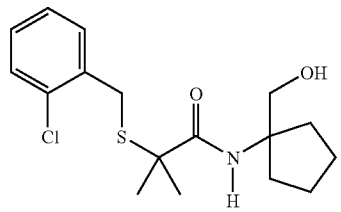

2-[(2-Chlorobenzyl)thio]-N-[1-(hydroxymethyl)cyclopentyl]-2-methylpropanamide

This compound was prepared using procedures analogous to those for example 22. LCMS: (M+H)⁺=342.0/344.0.

Example 55

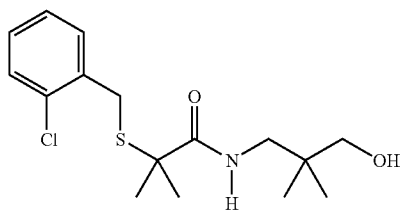

2-[(2-Chlorobenzyl)thio]-N-(3-hydroxy-2,2-dimethylpropyl)-2-methylpropanamide

This compound was prepared using procedures analogous to those for example 22. LCMS: (M+H)⁺=330.0/332.0.

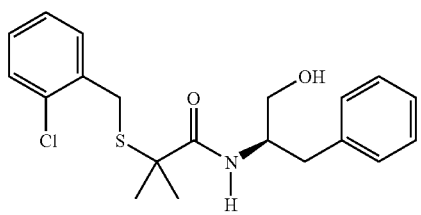

Example 56

N-[(1R)-1-Benzyl-2-hydroxyethyl]-2-[(2-chlorobenzyl)thio]-2-methylpropanamide

This compound was prepared using procedures analogous to those for example 22. LCMS: (M+H)⁺=378.0/380.0.

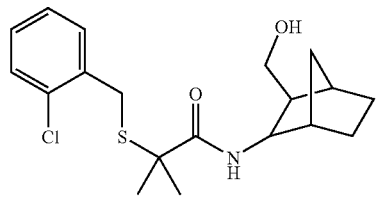

2-[(2-Chlorobenzyl)thio]-N-[3-(hydroxymethyl)bicyclo[2.2.1]hept-2-yl]-2-methylpropanamide This compound was prepared using procedures analogous to those for example 1. LCMS: (M+H)⁺=368.1/370.1.

Example 57

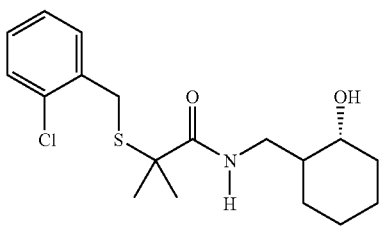

2-[(2-Chlorobenzyl)thio]-N-{[(trans)-2-hydroxycyclohexyl]methyl}-2-methylpropanamide This compound was prepared using procedures analogous to those for example 1. LCMS: (M+H)⁺=356.0/358.0.

Example 58

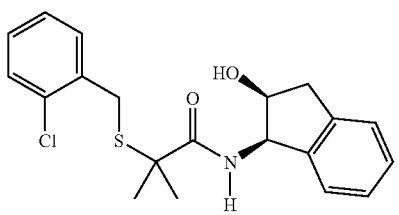

75

2-[(2-Chlorobenzyl)thio]-N-[(1R,2S)-2-hydroxy-2,3-dihydro-1H-inden-1-yl]-2-methylpropanamide This compound was prepared using procedures analogous to those for example 1. LCMS: $(M+H)^+=376.0/378.0$.

Example 59

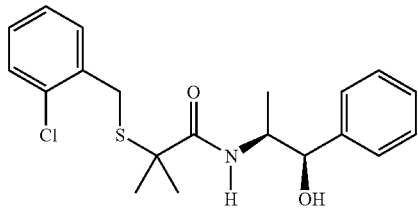

2-[(2-Chlorobenzyl)thio]-N-[(1S,2R)-2-hydroxy-1-methyl-2-phenylethyl]-2-methylpropanamide This compound was prepared using procedures analogous to those for example 1. LCMS: $(M+H)^+=378.1/380.0$; $(M-H_2O+H)^+=360.0/362.0$.

Example 60

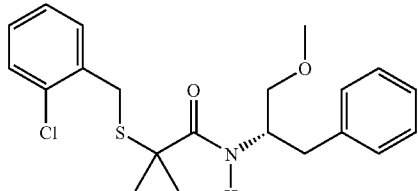

N-[(1S)-1-Benzyl-2-methoxyethyl]-2-[(2-chlorobenzyl)thio]-2-methylpropanamide

This compound was prepared using procedures analogous to those for example 1. LCMS: $(M+H)^+=392.0/394.0$.

Example 61

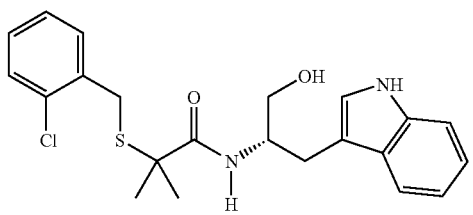

76

2-[(2-Chlorobenzyl)thio]-N-[(1S)-2-hydroxy-1-(1H-indol-3-ylmethyl)ethyl]-2-methyl propanamide This compound was prepared using procedures analogous to those for example 1. LCMS: $(M+H)^+=417.0/419.0$.

Example 62

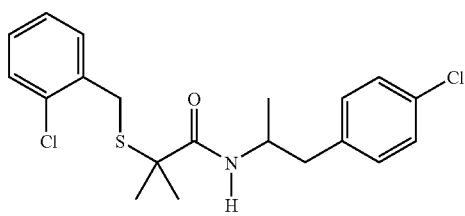

2-[(2-Chlorobenzyl)thio]-N-[2-(4-chlorophenyl)-1-methylethyl]-2-methyl-2-propanamide This compound was prepared using procedures analogous to those for example 1. LCMS: $(M+H)^+=396.0/398.0$.

Example 63

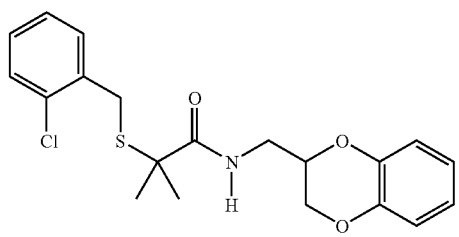

2-[(2-Chlorobenzyl)thio]-N-(2,3-dihydro-1,4-benzodioxin-2-ylmethyl)-2-methylpropanamide This compound was prepared using procedures analogous to those for example 1. LCMS: $(M+H)^+=392.0/394.0$.

Example 65

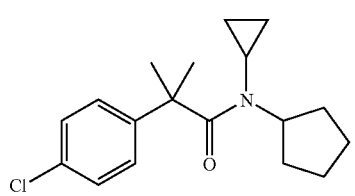

2-(4-Chlorophenyl)-N-cyclopentyl-N-cyclopropyl-2-methylpropanamide

This compound was prepared using procedures analogous to those for example 1. LCMS: (M+H)$^+$=306.1/308.1.

Example 66

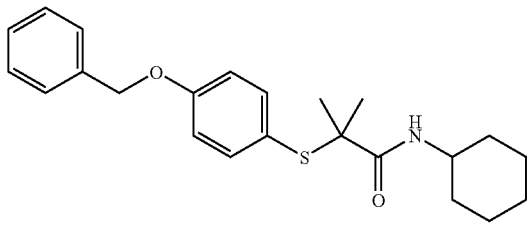

2-{[4-(Benzyloxy)phenyl]thio}-N-cyclohexyl-2-methylpropanamide

Step 1. Ethyl [(4-hydroxyphenyl)thio]acetate

A solution of 4-mercaptophenol in dry acetone was treated successively with excess of potassium carbonate and ethyl bromoacetate. The reaction mixture was refluxed overnight. After allowing the reaction mixture to cool to rt, it was filtered through celite and washed with acetone. The filtrate was concentrated and the residue was partitioned between water and EtOAc. The layers were separated and the organic layer was dried over MgSO$_4$, filtered and concentrated in-vacuo. The residue was purified by flash chromatography (silica, hexanes:ether, 3:1 to 1:1) to provide the desired thioether.

Step 2. Ethyl {[4-(benzyloxy)phenyl]thio}acetate

A solution of ethyl [(4-hydroxyphenyl)thio]acetate was dissolved in dry acetone and treated successively with potassium carbonate and benzyl bromide. The reaction mixture was refluxed overnight. After allowing the reaction mixture to cool to rt it was filtered through celite and washed with acetone. The filtrate was concentrated and the residue was partitioned between water and EtOAc. The layers were separated and the organic layer was dried over MgSO$_4$, filtered and concentrated in-vacuo. The residue was purified by flash chromatography (silica, hexanes:ether, 3:1 to 1:1) to provide the desired benzyl ether.

Step 3. Ethyl 2-{[4-(benzyloxy)phenyl]thio}-2-methylpropanoate

To a dry flask flushed with N$_2$ was added NaH (60% in mineral oil) and suspended in dry DMF (15 mL). After cooling in an ice-water bath, a solution of the acetate in DMF (20 mL) was added and the mixture was stirred at rt for 0.5 h. MeI (excess) was added and the reaction mixture was stirred at rt overnight. The reaction mixture was poured into a saturated NH$_4$Cl solution and extracted with EtOAc. The organic layer was washed with water, brine, dried over MgSO$_4$, filtered and concentrated in-vauo. The residue was purified by flash chromatography (silica, hexanes:ether, 8:1) to provide 0.821 g of the desired dimethylated product. The product was confirmed by $^1$H NMR.

Step 4. 2-{[4-(Benzyloxy)phenyl]thio}-N-cyclohexyl-2-methylpropanamide

The title compound was prepared by using a procedure that was analogous to that described for the synthesis of example 22, steps 2 and 3. LCMS: (M+H)$^+$=384.2.

Example 67

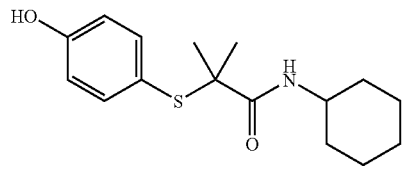

N-Cyclohexyl-2-[(4-hydroxyphenyl)thio]-2-methylpropanamide

2-{[4-(Benzyloxy)phenyl]thio}-N-cyclohexyl-2-methylpropanamide (prepared as example 66) was dissolved in chloroform under an atmosphere of nitrogen. To the solution was added excess TMSI via a dry syringe. The solution was stirred at rt for 16 h. The remaining TMSI was destroyed by adding a few drops of water and the intermediate trimethylsilyl ethers formed were hydrolyzed with MeOH (4 equiv). After stirring for a few min., the volatiles were removed in-vacuo and the resulting residue was dissolved in EtOAc. The solution was washed successively with an aq. sodium bisulfite solution, a saturated aq. NaHCO$_3$ solution, brine, dried over MgSO$_4$, filtered and concentrated. The residue was purified by flash chromatography (silica, hexanes:EtOAc, 4:1 to 2:1 to neat EtOAc) to provide the desired product as a white solid. LCMS: (M+H)$^+$=294.2.

Example 68

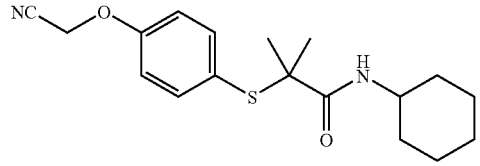

2-{[4-(Cyanomethoxy)phenyl]thio}-N-cyclohexyl-2-methylpropanamide

N-Cyclohexyl-2-[(4-hydroxyphenyl)thio]-2-methylpropanamide (prepared as example 67) was dissolved in DMF and to this was added potassium carbonate and bromoacetonitrile and the resulting solution was heated to 80° C. for 2 h. The reaction mixture was poured into water and extracted with EtOAC, dried over MgSO$_4$ and concentrated. The product was purified by flash chromatography, eluting with hexane/EtOAc, to provide 19.4 mg of the desired product. LCMS: (M+H)$^+$=333.2.

Example 69

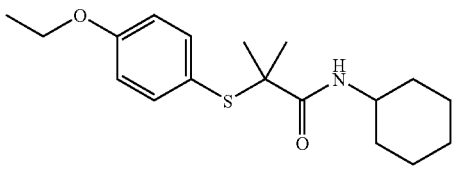

N-Cyclohexyl-2-[(4-ethoxyphenyl)thio]-2-methyl-propanamide

N-Cyclohexyl-2-[(4-hydroxyphenyl)thio]-2-methylpropanamide (prepared as example 67) was dissolved in DMF and to the solution was added iodoethane. The solution was cooled in an ice-water bath and treated with NaH (60% in mineral oil). After stirring in the ice-water bath for half an hour and at rt for 2 h, water was added followed by EtOAc. After stirring for 10 min., the layers were separated and the organic layer was washed with brine, dried over MgSO$_4$, filtered and concentrated. The residue was purified by flash chromatography (silica, hexanes:EtOAc, 6:1) to provide the desired product as a white solid. LCMS: (M+H)$^+$=322.2.

Example 70

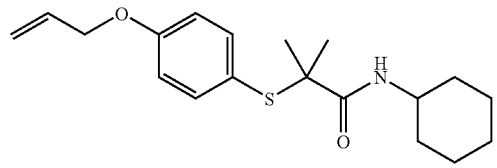

2-{[4-(Allyloxy)phenyl]thio}-N-cyclohexyl-2-methylpropanamide

The title compound was prepared by using a procedure that was analogous to that described for the synthesis of example 69. LCMS: (M+H)$^+$=334.2.

Example 71

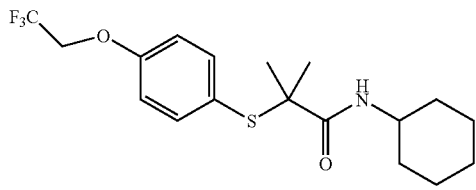

N-Cyclohexyl-2-methyl-2-{[4-(2,2,2-trifluoroethoxy)phenyl]thio}propanamide

The title compound was prepared by using a procedure that was analogous to that described for the synthesis of example 69. LCMS: (M+H)$^+$=376.2.

Example 72

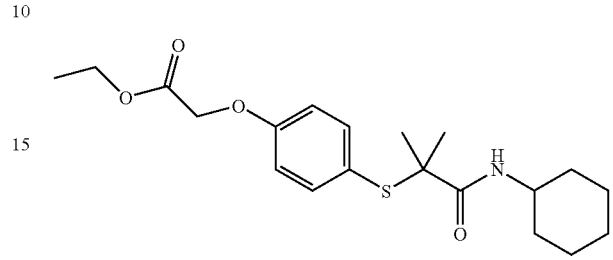

Ethyl (4-{[2-(cyclohexylamino)-1,1-dimethyl-2-oxoethyl]thio}phenoxy)acetate

The title compound was prepared by using a procedure that was analogous to that described for the synthesis of example 68. LCMS: (M+H)$^+$=380.2.

Example 73

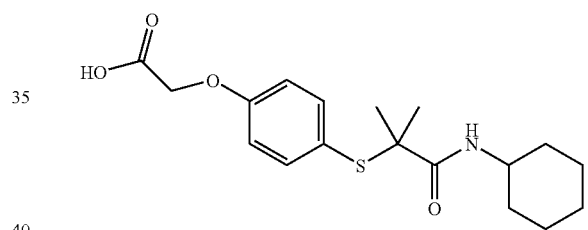

(4-{[2-(Cyclohexylamino)-1,1-dimethyl-2-oxoethyl]thio}phenoxy)acetic acid

Ethyl (4-{[2-(cyclohexylamino)-1,1-dimethyl-2-oxoethyl]thio}phenoxy)acetate (prepared as example 72) was dissolved in THF/MeOH and treated with an aq. LiOH/H$_2$O solution. The reaction mixture was stirred at rt for 16 h. The volatiles were removed in-vacuo and the residual aq. solution was acidified to pH=2 with a 1 N HCl solution. EtOAc was added and the layers were separated. The organic layer was dried over MgSO$_4$, filtered and concentrated to provide the desired carboxylic acid as a white solid. LCMS: (M+H)$^+$=352.2.

Example 74

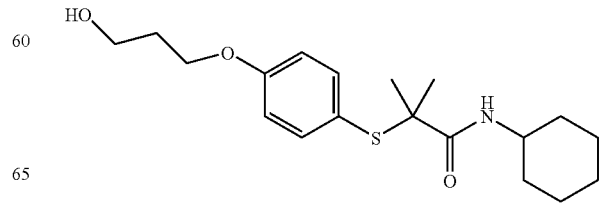

N-Cyclohexyl-2-{[4-(3-hydroxypropoxy)phenyl]thio}-2-methylpropanamide

2-{[4-(Allyloxy)phenyl]thio}-N-cyclohexyl-2-methylpropanamide was dissolved in THF and treated with 9-BBN at rt under $N_2$. After stirring at rt for 18 h, ethanol, 1N NaOH and a 30% $H_2O_2$ solution were added successively to the reaction mixture. After stirring for a few hours, the reaction mixture was acidified with 1N HCl to pH 2. Water and $CH_2Cl_2$ were added and the layers were separated. The organic layer was dried over $MgSO_4$, filtered and concentrated. The residue was purified by flash chromatography (silica, hexanes:EtOAc, 2:1 to 1:1) to provide the desired alcohol as a white solid. LCMS: $(M+H)^+=352.2$.

Example 75

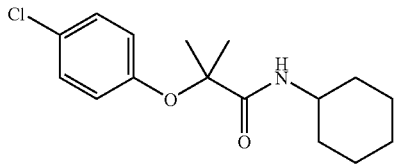

2-(4-Chlorophenoxy)-N-cyclohexyl-2-methylpropanamide

Step 1. Clofibrate

Ethyl 2-bromo-2-methyl-propanoate and p-chlorophenol was dissolved in dry acetone and treated with potassium carbonate. After stirring at rt for 30 min., the mixture was refluxed for 16 h. The reaction mixture was poured into water and extracted with DCM. The organic layer was dried over $MgSO_4$, filtered and concentrated. The residue was purified by flash chromatography (silica, hexanes:EtOAc, 9:1, 6:1 to 3:1) to give the desired product, which was used in the following step without further purification.

Step 2. 2-(4-Chlorophenoxy)-N-cyclohexyl-2-methylpropanamide

The title compound was prepared by using a procedure that was analogous to that described for the synthesis of example 22, steps 2 and 3. LCMS: $(M+H)^+=296.1/298.1$.

Example A

Enzymatic Assay of 11βHSD1

All in vitro assays were performed with clarified lysates as the source of 11βHSD1 activity. HEK-293 transient transfectants expressing an epitope-tagged version of full-length human 11βHSD1 were harvested by centrifugation. Roughly $2\times10^7$ cells were resuspended in 40 mL of lysis buffer (25 mM Tris-HCl, pH 7.5, 0.1 M NaCl, 1 mM $MgCl_2$ and 250 mM sucrose) and lysed in a microfluidizer. Lysates were clarified by centrifugation and the supernatants were aliquoted and frozen.

Inhibition of 11βHSD1 by test compounds was assessed in vitro by a Scintillation Proximity Assay (SPA). Dry test compounds were dissolved at 5 mM in DMSO. These were diluted in DMSO to suitable concentrations for the SPA assay. 0.8 μL of 2-fold serial dilutions of compounds were dotted on 384 well plates in DMSO such that 3 logs of compound concentration were covered. 20 μL of clarified lysate was added to each well. Reactions were initiated by addition of 20 μL of substrate-cofactor mix in assay buffer (25 mM Tris-HCl, pH 7.5, 0.1 M NaCl, 1 mM $MgCl_2$) to final concentrations of 400 μM NADPH, 25 nM $^3$H-cortisone and 0.007% Triton X-100. Plates were incubated at 37° C. for one hour. Reactions were quenched by addition of 40 μL of anti-mouse coated SPA beads that had been pre-incubated with 10 μM carbenoxolone and a cortisol-specific monoclonal antibody. Quenched plates were incubated for a minimum of 30 minutes at RT prior to reading on a Topcount scintillation counter. Controls with no lysate, inhibited lysate, and with no mAb were run routinely. Roughly 30% of input cortisone is reduced by 11βHSD1 in the uninhibited reaction under these conditions.

Test compounds having an $IC_{50}$ value less than about 20 μM according to this assay were considered active.

Example B

Cell-Based Assays for HSD Activity

Peripheral blood mononuclear cells (PBMCs) were isolated from normal human volunteers by Ficoll density centrifugation. Cells were plated at $4\times10^5$ cells/well in 200 μL of AIM V (Gibco-BRL) media in 96 well plates. The cells were stimulated overnight with 50 ng/ml recombinant human IL-4 (R&D Systems). The following morning, 200 nM cortisone (Sigma) was added in the presence or absence of various concentrations of compound. The cells were incubated for 48 hours and then supernatants were harvested. Conversion of cortisone to cortisol was determined by a commercially available ELISA (Assay Design).

Test compounds having an $IC_{50}$ value less than about 20 μM according to this assay were considered active.

Example C

Cellular Assay to Evaluate MR Antagonism

Assays for MR antagonism were performed essentially as described (Jausons-Loffreda et al. J Biolumin and Chemilumin, 1994, 9: 217-221). Briefly, HEK293/MSR cells (Invitrogen Corp.) were co-transfected with three plasmids: 1) one designed to express a fusion protein of the GAL4 DNA binding domain and the mineralocorticoid receptor ligand binding domain, 2) one containing the GAL4 upstream activation sequence positioned upstream of a firefly luciferase reporter gene (pFR-LUC, Stratagene, Inc.), and 3) one containing the *Renilla* luciferase reporter gene cloned downstream of a thymidine kinase promoter (Promega). Transfections were performed using the FuGENE6 reagent (Roche). Transfected cells were ready for use in subsequent assays 24 hours post-transfection.

In order to evaluate a compound's ability to antagonize the MR, test compounds were diluted in cell culture medium (E-MEM, 10% charcoal-stripped FBS, 2 mM L-glutamine) supplemented with 1 nM aldosterone and applied to the transfected cells for 16-18 hours. After the incubation of the cells with the test compound and aldosterone, the activity of firefly luciferase (indicative of MR agonism by aldosterone) and *Renilla* luciferase (normalization control) were determined using the Dual-Glo Luciferase Assay System (Promega). Antagonism of the mineralocorticoid receptor was determined by monitoring the ability of a test compound to attenuate the aldosterone-induced firefly luciferase activity.

What is claimed is:

1. A compound of Formula I:

or pharmaceutically acceptable salt thereof, wherein:

$R^1$ is phenyl, $Cy^1$-$(CH_2)_m$—O— or $Cy^1$-$(CH_2)_m$—S—, wherein said phenyl is optionally substituted by 1, 2, 3, 4 or 5 $R^{1a}$;

$R^2$ is —$(CR^4R^5)_n Cy^2$, —$(CR^4R^5)_t Cy^3$ or $Cy^4$;

$R^3$ is H, $C_{1-6}$ alkyl or $C_{3-6}$ cycloalkyl;

$R^4$ and $R^5$ are each, independently, H, halo, OH, CN, $C_{1-4}$ alkyl, $C_{1-4}$ alkoxy, wherein said $C_{1-4}$ alkyl or $C_{1-4}$ alkoxy is optionally substituted with one or more $R^{4a}$;

$R^6$ is H or $C_{1-6}$ alkyl optionally substituted by one or more OH;

each $R^{1a}$ is independently halo, CN, $NO_2$, $OR^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^{1c}$ is halo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, phenyl, benzyl, $C(O)OR^g$ or $OR^g$;

$R^{4a}$ is halo, CN, $NO_2$, OH, $C_{1-4}$ alkoxy, $C_{1-4}$ haloalkoxy, amino, $C_{1-4}$ alkylamino or $C_{2-8}$ dialkylamino;

$Cy^1$ is aryl, heteroaryl, cycloalkyl or heterocycloalkyl, each optionally substituted by 1, 2, 3, 4 or 5-W—X—Y—Z;

$Cy^2$ is:

$Cy^3$ is phenyl optionally substituted by one or more $R^{1a}$;

$Cy^4$ is:

U is $CH_2$;

W, W' and W" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

X, X' and X" are each, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

Y, Y' and Y" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z, Z' and Z" are each, independently, H, halo, CN, $NO_2$, OH, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein two —W—X—Y—Z together with two adjacent atoms to which they are attached optionally form a 3-20 membered cycloalkyl group or 3-20 membered heterocycloalkyl group, each optionally substituted by 1, 2 or 3-W'—X'—Y'—Z';

or wherein two —W—X—Y—Z together with two adjacent atoms to which they are attached optionally form a 5- or 6-membered aryl or 5- or 6-membered heteroaryl group, each optionally substituted by 1, 2 or 3-W"—X"—Y"—Z";

wherein —W—X—Y—Z is other than H;

wherein —W'—X'—Y'—Z' is other than H;

wherein —W"—X"—Y"—Z" is other than H;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^e$ and $R^f$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^e$ and $R^f$ together with the N atom to which they are attached form a 4-, 5-, 6- or 7-membered heterocycloalkyl group;

$R^g$ is H, $C_{1-6}$ alkyl, $C_{1-6}$ haloalkyl, $C_{2-6}$ alkenyl, $C_{2-6}$ alkynyl, aryl, heteroaryl, cycloalkyl, arylalkyl, heteroarylalkyl or cycloalkylalkyl;

j is 0, 1, 2, or 3;

m is 0, 1, or 2;

n is 0, 1, 2, or 3;

q is 0, 1, 2, 3, 4 or 5;

r is 1 or 2; and t is 2 or 3;

with the provisos:

a) when $R^1$ is phenyl optionally substituted by 1, 2, 3, 4 or 5 $R^{1a}$ and $R^2$ is $(CR^4R^5)_jCy^3$, at least one of $R^4$ and $R^5$ is other than H;

b) when $R^1$ is phenyl optionally substituted by 1, 2, 3, 4 or 5 $R^{1a}$ and $R^2$ is $Cy^2$, $Cy^2$ is other than cyclohexyl substituted by one $NR^cR^d$; and c) when $R^2$ is cyclohexyl, $R^1$ is other than 3,5-di-tert-butyl-4-hydroxyphenyl.

2. The compound of claim 1 having the structure of formula II:

or pharmaceutically acceptable salt thereof, wherein:

$R^1$ is phenyl optionally substituted by 1, 2, 3, 4 or 5 $R^{1a}$;

$R^3$ is H, $C_{1-6}$ alkyl or $C_{3-6}$ cycloalkyl;

$R^4$ and $R^5$ are each, independently, H, halo, OH, CN, $C_{1-4}$ alkyl, $C_{1-4}$ alkoxy, wherein said $C_{1-4}$ alkyl or $C_{1-4}$ alkoxy is optionally substituted with one or more $R^{4a}$;

$R^6$ is H or $C_{1-6}$ alkyl optionally substituted by one or more OH;

each $R^{1a}$ is independently halo, CN, $NO_2$, $OR^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{2-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$ or $S(O)_2NR^cR^d$;

$R^{4a}$ is halo, CN, $NO_2$, OH, $C_{1-4}$ alkoxy, $C_{1-4}$ haloalkoxy, amino, $C_{1-4}$ alkylamino or $C_{2-8}$ dialkylamino;

$Cy^2$ is:

U is $CH_2$;

each W' is, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

each X' is, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

each Y' is, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

each Z' is, independently, H, halo, CN, $NO_2$, OH, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein —W'—X'—Y'—Z' is other than H;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^e$ and $R^f$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^e$ and $R^f$ together with the N atom to which they are attached form a 4-, 5-, 6- or 7-membered heterocycloalkyl group;

n is 0, 1, 2, or 3;
q is 0, 1, 2, 3, 4 or 5; and
r is 1 or 2;
with the provisos:
a) when n is 0, $Cy^2$ is other than 1-[3-(2-methoxyphenoxy) benzyl]-piperidine-4-yl, 1-[3-(2-methoxyphenoxy)benzyl]-pyrrolidin-3-yl, 1,2,2,6,6-pentamethyl-piperidin-4-yl or cyclohexyl substituted by one $NR^cR^d$; and
b) when n is 0 and $Cy^2$ is cyclohexyl, $R^1$ is other than 3,5-di-tert-butyl-4-hydroxyphenyl.

3. The compound of claim 2 having the structure of formula IIa:

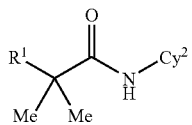

or pharmaceutically acceptable salt thereof, wherein:
$R^1$ is phenyl optionally substituted by 1, 2, 3, 4 or 5 $R^{1a}$;
$R^6$ is H or $C_{1-6}$ alkyl optionally substituted by one or more OH;
$R^7$ is halo, CN, $NO_2$, OH, $OR^a$, $SR^a$, $C(O)R^b$, $C(O)NR^cR^d$, $C(O)OR^a$, $OC(O)R^b$, $OC(O)NR^cR^d$, $S(O)R^b$, $S(O)NR^cR^d$, $S(O)_2R^b$, $S(O)_2NR^cR^d$, $C_{1-4}$ alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkyl or heterocycloalkyl, wherein said $C_{1-4}$ alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkyl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;
$Cy^2$ is:

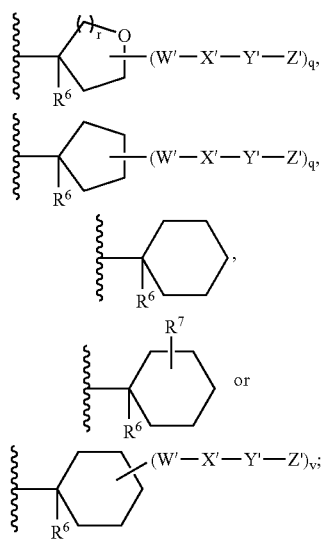

$R^{1a}$ is halo, CN, $NO_2$, $OR^a$, $C_{1-4}$ alkoxy, $C_{1-4}$ haloalkoxy, amino, $C_{1-4}$ alkylamino, $C_{2-4}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$ or $S(O)_2NR^cR^d$;

each W' is, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

each X' is, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

each Y' is, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

each Z' is, independently, H, halo, CN, $NO_2$, OH, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein —W'—X'—Y'—Z is other than H;
$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;
$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;
$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;
or $R^c$ and $R^d$ together with the N atom to which they are attached form a 4-, 5-, 6- or 7-membered heterocycloalkyl group;
$R^e$ and $R^f$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;
or $R^e$ and $R^f$ together with the N atom to which they are attached form a 4-, 5-, 6- or 7-membered heterocycloalkyl group;
q is 0, 1, 2, 3, 4 or 5;
r is 1 or 2;
t is 2 or 3; and
v is 2, 3, 4 or 5;
with the proviso that when $Cy^2$ is cyclohexyl, $R^1$ is other than 3,5-di-tert-butyl-4-hydroxyphenyl.

4. The compound of claim 2 having the structure of Formula IIaa:

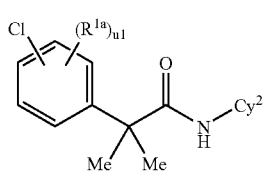

or pharmaceutically acceptable salt thereof, wherein:

$R^6$ is H or $C_{1-6}$ alkyl optionally substituted by one or more OH;

$R^7$ is halo, CN, $NO_2$, OH, $OR^a$, $SR^a$, $C(O)R^b$, $C(O)NR^cR^d$, $C(O)OR^a$, $OC(O)R^b$, $OC(O)NR^cR^d$, $S(O)R^b$, $S(O)NR^cR^d$, $S(O)_2R^b$, $S(O)_2NR^cR^d$, $C_{1-4}$ alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkyl or heterocycloalkyl, wherein said $C_{1-4}$ alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkyl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$Cy^2$ is:

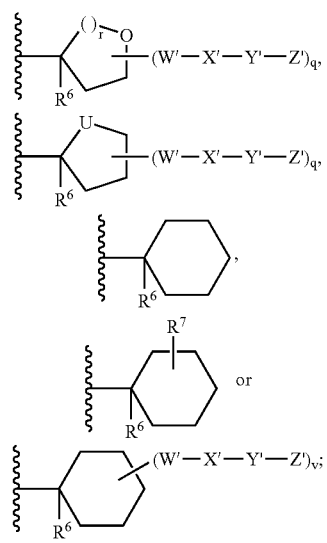

$R^{1a}$ is halo, CN, $NO_2$, $OR^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

each W' is, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

each X' is, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

each Y' is, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z' is, independently, H, halo, CN, $NO_2$, OH, $C_{1-4}$ alkoxy, $C_{1-4}$ halo alkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein —W'—X'—Y'—Z is other than H;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^e$ and $R^f$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^e$ and $R^f$ together with the N atom to which they are attached form a 4-, 5-, 6- or 7-membered heterocycloalkyl group;

q is 0, 1, 2, 3, 4 or 5;

r is 1 or 2;

v is 2, 3, 4 or 5; and u1 is 0, 1, 2, 3 or 4.

5. The compound of claim 2 having the structure of Formula IIb:

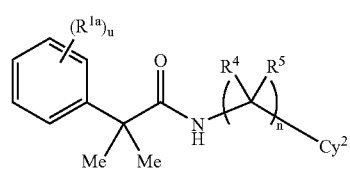

or pharmaceutically acceptable salt thereof, wherein:

$R^4$ and $R^5$ are each, independently, H, halo, OH, CN, $C_{1-4}$alkyl, $C_{1-4}$ alkoxy, wherein said $C_{1-4}$ alkyl or $C_{1-4}$ alkoxy is optionally substituted with one or more $R^{4a}$;

$R^6$ is H or $C_{1-6}$ alkyl optionally substituted by one or more OH;

each $R^{1a}$ is independently halo, CN, $NO_2$, $OR^a$, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$ or $S(O)_2NR^cR^d$;

$R^{4a}$ is halo, CN, $NO_2$, OH, $C_{1-4}$ alkoxy, $C_{1-4}$ haloalkoxy, amino, $C_{1-4}$ alkylamino or $C_{2-8}$ dialkylamino;

$Cy^2$ is:

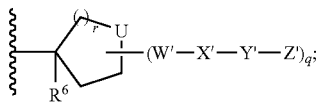

U is $CH_2$;

each W' is, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

each X' is, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

each Y' is, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_4$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

each Z' is, independently, H, halo, CN, $NO_2$, OH, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein —W'—X'—Y'—Z' is other than H;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^e$ and $R^f$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^e$ and $R^f$ together with the N atom to which they are attached form a 4-, 5-, 6- or 7-membered heterocycloalkyl group;

n is 1, 2 or 3;

q is 0, 1, 2, 3, 4 or 5;

r is 1 or 2; and u is 0, 1, 2, 3, 4 or 5.

6. The compound of claim 1 having the structure of Formula III:

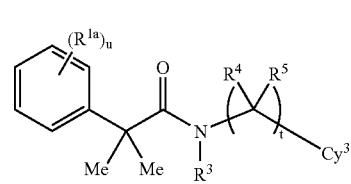

or pharmaceutically acceptable salt thereof, wherein:

$R^3$ is H, $C_{1-6}$ alkyl or $C_{3-6}$ cycloalkyl;

$R^4$ and $R^5$ are each, independently, H, halo, OH, CN, $C_{1-4}$alkyl, $C_{1-4}$ alkoxy, wherein said $C_{1-4}$ alkyl or $C_{1-4}$ alkoxy is optionally substituted with one or more $R^{4a}$;

$R^{1a}$ is each independently, halo, CN, $NO_2$, $OR^a$, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ ethyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^{4a}$ is halo, CN, $NO_2$, OH, $C_{1-4}$ alkoxy, $C_{1-4}$ haloalkoxy, amino, $C_{1-4}$ alkylamino or $C_{2-8}$ dialkylamino;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

t is 2 or 3; and u is 0, 1, 2, 3, 4 or 5;

with the proviso that at least one of $R^4$ and $R^5$ is other than H.

7. The compound of claim 3 having the structure of Formula IIIa:

$$\text{IIIa}$$

[Structure: phenyl with $(R^{1a})_u$ substituents, connected to C(Me)(Me)-C(O)-NH-C(R^{4'})(R^{5'})-(CR^4R^5)_{t1}-Cy^3]

or pharmaceutically acceptable salt thereof, wherein:

$R^4$ and $R^5$ are each, independently, H, halo, OH, CN, $C_{1-4}$alkyl, $C_{1-4}$ alkoxy, wherein said $C_{1-4}$ alkyl or $C_{1-4}$ alkoxy is optionally substituted with one or more $R^{4a}$;

$R^{4'}$ is halo, OH, CN, $C_{1-4}$alkyl, $C_{1-4}$ alkoxy, wherein said $C_{1-4}$ alkyl or $C_{1-4}$ alkoxy is optionally substituted with one or more halo, CN, $NO_2$, OH, $C_{1-4}$ alkoxy, or $C_{1-4}$ haloalkoxy;

$R^{5'}$ is H, halo, OH, CN, $C_{1-4}$alkyl, $C_{1-4}$ alkoxy, wherein said $C_{1-4}$ alkyl or $C_{1-4}$ alkoxy is optionally substituted with one or more $R^{4a}$;

$R^{1a}$ is independently, halo, CN, $NO_2$, $OR^a$, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^{4a}$ is halo, CN, $NO_2$, OH, $C_{1-4}$ alkoxy, $C_{1-4}$ haloalkoxy, amino, $C_{1-4}$ alkylamino or $C_{2-8}$ dialkylamino;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

t1 is 1 or 2; and u is 0, 1, 2, 3, 4 or 5.

8. The compound of claim 1 having the structure of formula IV:

$$\text{IV}$$

[Structure: phenyl with $(R^{1a})_u$, connected to C(Me)(Me)-C(O)-N(R^3)-cyclopropyl with $R^6$ and $(R^{1c})_j$]

or pharmaceutically acceptable salt thereof, wherein:

$R^3$ is H, $C_{1-6}$ alkyl or $C_{3-6}$ cycloalkyl;

$R^6$ is H or $C_{1-6}$ alkyl optionally substituted by one or more OH;

$R^{1a}$ is halo, CN, $NO_2$, $OR^a$, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^{1c}$ is halo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, phenyl, benzyl, $C(O)OR^g$ or $OR^g$;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^g$ is H, $C_{1-6}$ alkyl, $C_{1-6}$ haloalkyl, $C_{2-6}$ alkenyl, $C_{2-6}$ alkynyl, aryl, heteroaryl, cycloalkyl, arylalkyl, heteroarylalkyl or cycloalkylalkyl;

u is 0, 1, 2, 3, 4 or 5; and j is 0, 1, 2 or 3.

9. The compound of claim 1 having the structure of Formula V:

$$\text{V}$$

[Structure: $Cy^1$-(CH_2)_m-S-C(Me)(Me)-C(O)-N(R^2)(R^3)]

or pharmaceutically acceptable salt thereof, wherein:

$R^2$ is $(CR^4R^5)_nCy^2$, $(CR^4R^5)_tCy^3$, or $Cy^4$;

$R^3$ is H, $C_{1-6}$ alkyl or $C_{3-6}$ cycloalkyl;

$R^4$ and $R^5$ are each, independently, H, halo, OH, ON, $C_{1-4}$alkyl, $C_{1-4}$ alkoxy, wherein said $C_{1-4}$ alkyl or $C_{1-4}$ alkoxy is optionally substituted with one or more $R^{4a}$;

$R^6$ is H, $C_{1-6}$ alkyl optionally substituted by one or more OH;

each $R^{1a}$ is, independently, halo, CN, $NO_2$, $OR^a$, $C_{1-4}$ alkoxy, $C_{1-4}$haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^{1c}$ is halo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, phenyl, benzyl, $C(O)OR^g$ or $OR^g$;

$R^{4a}$ is halo, ON, $NO_2$, OH, $C_{1-4}$ alkoxy, $C_{1-4}$ haloalkoxy, amino, $C_{1-4}$ alkylamino or $C_{2-8}$ dialkylamino;

$Cy^1$ is aryl, heteroaryl, cycloalkyl or heterocycloalkyl, each optionally substituted by 1, 2, 3, 4 or 5-W—X—Y—Z;

$Cy^2$ is:

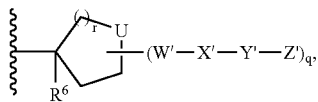

$Cy^3$ is phenyl optionally substituted by one or more $R^{1a}$;
$Cy^4$ is:

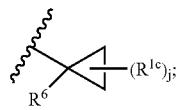

U is $CH_2$;

W, W' and W'' are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

X, X' and X'' are each, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

Y, Y' and Y'' are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl or $C_{2-6}$ alkynylenyl is optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z, Z' and Z'' are each, independently, H, halo, CN, $NO_2$, OH, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein two —W—X—Y—Z together with two adjacent atoms to which they are attached optionally form a 3-20 membered cycloalkyl group or 3-20 membered heterocycloalkyl group, each optionally substituted by 1, 2 or 3-W''—X''—Y''—Z'';

or wherein two —W—X—Y—Z together with two adjacent atoms to which they are attached optionally form a 5- or 6-membered aryl or 5- or 6-membered heteroaryl group, each optionally substituted by 1, 2 or 3-W''—X''—Y''—Z'';

wherein —W—X—Y—Z is other than H;
wherein —W'—X'—Y'—Z' is other than H;
wherein —W''—X''—Y''—Z'' is other than H;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^e$ and $R^f$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^e$ and $R^f$ together with the N atom to which they are attached form a 4-, 5-, 6- or 7-membered heterocycloalkyl group;

$R^g$ is H, $C_{1-6}$ alkyl, $C_{1-6}$ haloalkyl, $C_{2-6}$ alkenyl, $C_{2-6}$ alkynyl, aryl, heteroaryl, cycloalkyl, arylalkyl, heteroarylalkyl or cycloalkylalkyl;

m is 0, 1, or 2;
n is 0, 1, 2, or 3;
t is 2 or 3;
q is 0, 1, 2, 3, 4 or 5;
r is 1 or 2; and
j is 0, 1, 2, or 3.

10. The compound of claim 1, or a pharmaceutically acceptable salt thereof, wherein $R^1$ is phenyl optionally substituted by 1, 2, 3, 4 or 5 halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, $C_{1-6}$ haloalkyl, aryl, cycloalkyl, heteroaryl or heterocycloalkyl.

11. The compound of claim 1, or a pharmaceutically acceptable salt thereof, wherein $R^1$ is phenyl substituted by 1, 2 or 3 halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, $C_{1-6}$ haloalkyl, aryl, cycloalkyl, heteroaryl or heterocycloalkyl.

12. The compound of claim 1, or a pharmaceutically acceptable salt thereof, wherein $R^1$ is phenyl substituted by 1, 2 or 3 halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, or $C_{1-6}$ haloalkyl.

13. The compound of claim 1, or a pharmaceutically acceptable salt thereof, wherein $R^1$ is 4-chlorophenyl optionally substituted by 1 or 2 halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, or $C_{1-6}$ haloalkyl.

14. The compound of claim 1, or a pharmaceutically acceptable salt thereof, wherein:
$R^2$ is $(CR^4R^5)_nCy^2$;
$Cy^2$ is:

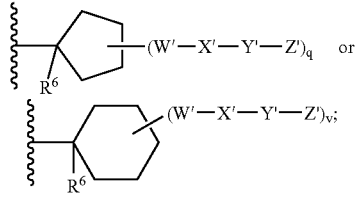

—W'—X'—Y'—Z' is independently halo, CN, $NO_2$, $OR^a$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-4}$ alkoxy, $C_{1-4}$ haloalkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group; and v is 2, 3, 4 or 5.

15. The compound of claim 1, or a pharmaceutically acceptable salt thereof, wherein:
$R^2$ is $(CR^4R^5)_nCy^2$;
$Cy^2$ is:

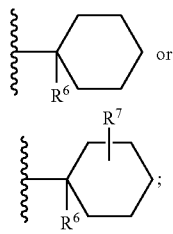

$R^7$ is halo, CN, $NO_2$, OH, $OR^a$, $SR^a$, $C(O)R^b$, $C(O)NR^cR^d$, $C(O)OR^a$, $OC(O)R^b$, $OC(O)NR^cR^d$, $S(O)R^b$, $S(O)NR^cR^d$, $S(O)_2R^b$, $S(O)_2NR^cR^d$, $C_{1-4}$ alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-4}$ alkoxy, $C_{1-6}$ alkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted by 1, 2 or 3 halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^a$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; and $R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

with the proviso that when n is 0 and $Cy^2$ is cyclohexyl, $R^1$ is other than 3,5-di-tert-butyl-4-hydroxyphenyl.

16. The compound of claim 1, or a pharmaceutically acceptable salt thereof, wherein $R^2$ is $(CR^4R^5)_nCy^2$, and n is 1, 2 or 3.

17. The compound of claim 1, or a pharmaceutically acceptable salt thereof, wherein $R^2$ is $(CR^4R^5)_tCy^3$ and t is 2.

18. The compound of claim 1, or a pharmaceutically acceptable salt thereof, wherein $R^2$ is $(CR^4R^5)_tCy^3$ and t is 3.

19. The compound of claim 1, or a pharmaceutically acceptable salt thereof, wherein:

$R^2$ is $(CR^4R^5)(CR^4R^5)_{t1}Cy^3$;

$R^{4'}$ is halo, OH, CN, $C_{1-4}$ alkyl, $C_{1-4}$ alkoxy, wherein said $C_{1-4}$ alkyl or $C_{1-4}$ alkoxy is optionally substituted with one or more halo, CN, $NO_2$, OH, $C_{1-4}$ alkoxy, or $C_{1-4}$ haloalkoxy;

$R^{5'}$ is, H, halo, OH, CN, $C_{1-4}$ alkyl, $C_{1-4}$ alkoxy, wherein said $C_{1-4}$ alkyl or $C_{1-4}$ alkoxy is optionally substituted with one or more halo, CN, $NO_2$, OH, $C_{1-4}$ alkoxy, $C_{1-4}$ haloalkoxy, amino, $C_{1-4}$ alkylamino or $C_{2-8}$ dialkylamino; and t1 is 1 or 2.

20. The compound of claim 1, or a pharmaceutically acceptable salt thereof, wherein $R^2$ is:

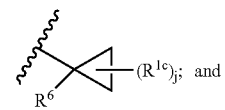

$R^6$ is H or $C_{1-6}$ alkyl.

21. The compound of claim 1, or a pharmaceutically acceptable salt thereof, wherein:
$R^2$ is:

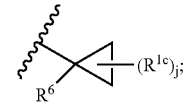

$R^{1c}$ is halo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, phenyl, or benzyl; and j is 0, 1 or 2.

22. A compound selected from:
2-(4-chlorophenyl)-N-cyclohexyl-2-methylpropanamide;
2-(4-chlorophenyl)-N-[(1R,2R)-2-(benzyloxy)cyclohexyl]-2-methylpropanamide;
2-(4-chlorophenyl)-2-methyl-N-(2-phenylcyclopropyl)propanamide;
2-(4-chlorophenyl)-N-[(1S)-1-cyclohexylethyl]-2-methylpropanamide;
2-(4-chlorophenyl)-N-(1-methyl-3-phenylpropyl)-2-methylpropanamide;
2-(4-chlorophenyl)-N-[1-(3-hydroxy-4-methylbenzyl)propyl]-2-methylpropanamide;
2-(4-chlorophenyl)-N-(1,1-dimethyl-2-phenylethyl)-2-methylpropanamide;
2-(4-chlorophenyl)-N-[1-(hydroxymethyl)cyclopentyl]-2-methylpropanamide;
2-(4-chlorophenyl)-N-(3-hydroxy-2,2-dimethylpropyl)-2-methylpropanamide;
N-[(1R)-1-benzyl-2-hydroxyethyl]-2-(4-chlorophenyl)-2-methylpropanamide;
2-(4-chlorophenyl)-N-{[(trans)-2-hydroxycyclohexyl]methyl}-2-methylpropanamide;
2-(4-chlorophenyl)-N-[(1S,2R)-2-hydroxy-1-methyl-2-phenylethyl]-2-methylpropanamide;

N-[(1S)-1-benzyl-2-methoxyethyl]-2-(4-chlorophenyl)-2-methylpropanamide; and 2-(4-chlorophenyl)-N-cyclopentyl-N-cyclopropyl-2-methylpropanamide, and pharmaceutically acceptable salts thereof.

23. A compound of claim 1 selected from:

N-Cyclohexyl-2-methyl-2-(phenylthio)propanamide;

N-[(1R,2R)-2-(benzyloxy)cyclohexyl]-2-methyl-2-(phenylthio)propanamide;

2-methyl-N-(2-phenylcyclopropyl)-2-(phenylthio)propanamide;

N-[(1S)-1-cyclohexylethyl]-2-methyl-2-(phenylthio)propanamide;

N-(1-methyl-3-phenylpropyl)-2-methyl-2-(phenylthio)propanamide;

N-[1-(3-hydroxy-4-methylbenzyl)propyl]-2-methyl-2-(phenylthio)propanamide;

N-(1,1-dimethyl-2-phenylethyl)-2-methyl-2-(phenylthio)propanamide;

N-[1-(hydroxymethyl)cyclopentyl]-2-methyl-2-(phenylthio)propanamide;

N-[(1R)-1-benzyl-2-hydroxyethyl]-2-methyl-2-(phenylthio)propanamide;

N-{[(trans)-2-hydroxycyclohexyl]methyl}-2-methyl-2-(phenylthio)propanamide;

N-[(1S,2R)-2-hydroxy-1-methyl-2-phenylethyl]-2-methyl-2-(phenylthio)propanamide;

N-[2-(4-chlorophenyl)-1-methylethyl]-2-methyl-2-(phenylthio)propanamide;

2-[(2-chlorobenzyl)thio]-N-Cyclohexyl-2-methylpropanamide;

2-{[4-(benzyloxy)phenyl]thio}-N-cyclohexyl-2-methylpropanamide;

N-cyclohexyl-2-[(4-hydroxyphenyl)thio]-2-methylpropanamide;

2-{([4-(cyanomethoxy)phenyl]thio}-N-cyclohexyl-2-methylpropanamide;

N-cyclohexyl-2-[(4-ethoxyphenyl)thio]-2-methylpropanamide;

2-{[4-(allyloxy)phenyl]thio}-N-cyclohexyl-2-methylpropanamide;

N-cyclohexyl-2-methyl-2-{[4-(2,2,2-trifluoroethoxy)phenyl]thio}propanamide;

ethyl (4-{[2-(cyclohexylamino)-1,1-dimethyl-2-oxoethyl]thio}phenoxy)acetate;

(4-{[2-(cyclohexylamino)-1,1-dimethyl-2-oxoethyl]thio}phenoxy)acetic acid;

N-cyclohexyl-2-{[4-(3-hydroxypropoxy)phenyl]thio}-2-methylpropanamide;

2-[(2-chlorobenzyl)thio]-2-methyl-N-(2-phenylcyclopropyl)propanamide;

2-[(2-chlorobenzyl)thio]-N-[(1S)-1-cyclohexylethyl]-2-methylpropanamide;

2-[(2-chlorobenzyl)thio]-N-(1-methyl-3-phenylpropyl)-2-methylpropanamide;

2-[(2-chlorobenzyl)thio]-N-(1,1-dimethyl-2-phenylethyl)-2-methylpropanamide;

2-[(2-chlorobenzyl)thio]-N-[1-(hydroxymethyl)cyclopentyl]-2-methylpropanamide;

2-[(2-chlorobenzyl)thio]-N-(3-hydroxy-2,2-dimethylpropyl)-2-methylpropanamide;

2-[(2-chlorobenzyl)thio]-N-{[(trans)-2-hydroxycyclohexyl]methyl}-2-methylpropanamide;

2-[(2-chlorobenzyl)thio]-N-[(1S,2R)-2-hydroxy-1-methyl-2-phenylethyl]-2-methylpropanamide; and 2-[(2-chlorobenzyl)thio]-N-[2-(4-chlorophenyl)-1-methylethyl]-2-methyl-2-propanamide;

pharmaceutically acceptable salts thereof.

24. A composition comprising a compound of claim 1, 22, or 23, or a pharmaceutically acceptable salt thereof, and a pharmaceutically acceptable carrier.

25. A compound according to claim 1, or a pharmaceutically acceptable salt thereof, wherein $R^1$ is $Cy^1$-$(CH_2)_m$—O—.

26. A compound according to claim 1, or a pharmaceutically acceptable salt thereof, wherein $R^1$ is $Cy^1$-$(CH_2)_m$—S—.

27. A compound according to claim 1, or a pharmaceutically acceptable salt thereof, wherein $R^2$ is $Cy^4$.

28. The compound of claim 14, or a pharmaceutically acceptable salt thereof, wherein $Cy^2$ is:

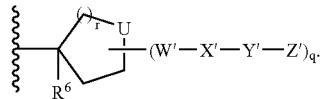

* * * * *

UNITED STATES PATENT AND TRADEMARK OFFICE
CERTIFICATE OF CORRECTION

PATENT NO. : 7,687,665 B2
APPLICATION NO. : 11/159865
DATED : March 30, 2010
INVENTOR(S) : Wenqing Yao et al.

It is certified that error appears in the above-identified patent and that said Letters Patent is hereby corrected as shown below:

Col. 83, line 63 (claim 1) replace

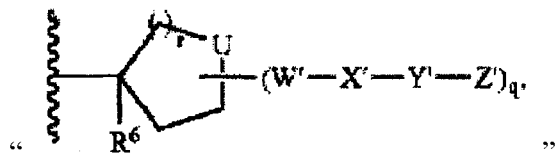

with

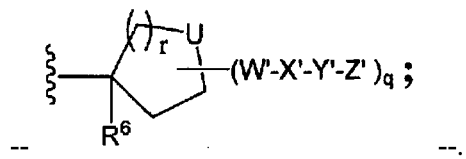

Col. 84, line 50-51 (claim 1), replace "1, 2 or 3-W'-X'-Y'-Z';" with
-- 1, 2 or 3 –W"-X"-Y"-Z"; --.

Col. 85, line 59 (claim 2), replace "$C_{2-6}$ alkyl" with -- $C_{1-6}$ alkyl --.

Col. 85, line 66 (claim 2), replace "$S(O)_2R^b$ or $S(O)_2NR^cR^d$;"
with -- $S(O)_2R^b$, or $S(O)_2NR^cR^d$; --.

Col. 86, line 6 (claim 2) replace

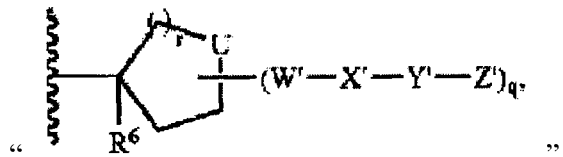

Signed and Sealed this
Seventh Day of June, 2011

David J. Kappos
*Director of the United States Patent and Trademark Office* with

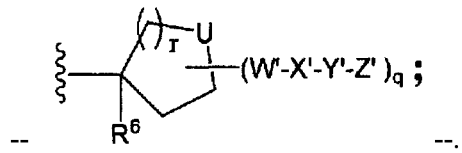

Col. 87, line 45 (claim 3), immediately below "Cy² is:" delete

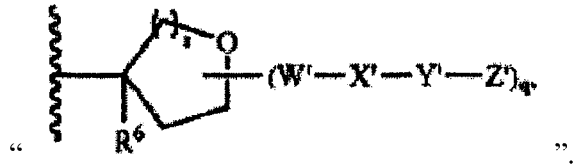

Col. 87, line 67 (claim 3), replace "$C_{2-4}$ dialkylamino" with -- $C_{2-8}$ dialkylamino --.

Col. 88, lines 9-10 (claim 3), replace "$S(O)_2R^b$ or $S(O)_2NR^cR^d$;" with -- $S(O)_2R^b$, or $S(O)_2NR^cR^d$; --.

Col. 88, line 44 (claim 3), replace "wherein –W'-X'-Y'-Z is other than H;" with -- wherein –W'-X'-Y'-Z' is other than H; --.

Col. 89, line 35-40 (claim 4), immediately below "Cy² is:" replace

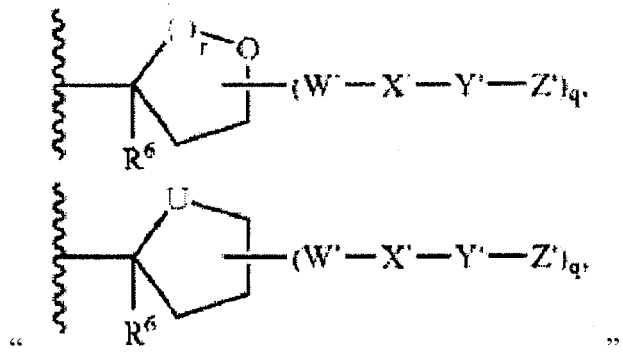

with

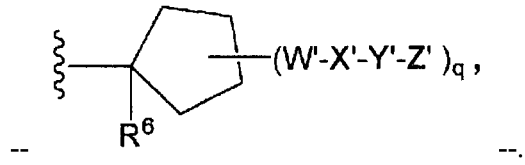

Col. 90 line 6 (claim 4), replace "$C_{1-4}$haloalkoxy" with -- $C_{1-4}$ haloalkoxy --.

Col. 90, line 22 (claim 4), replace "Z'" with -- each Z' --.

Col. 90, line 23 (claim 4), replace "$C_{1-4}$halo alkoxy," with -- $C_{1-4}$ haloalkoxy, --.

Col. 90, line 34 (claim 4), replace "wherein –W'-X'-Y'-Z is other than H;"

with -- wherein –W'-X'-Y'-Z' is other than H; --.

Col. 91, line 19 (claim 5), replace "S(O)$_2$R$^b$ or S(O)$_2$NR$^c$R$^d$;"
with -- S(O)$_2$R$^b$, or S(O)$_2$NR$^c$R$^d$; --.

Col. 91, line 47 (claim 5), replace "SO$_4$," with -- SO$_2$, --.

Col. 92, line 44-45 (claim 6), replace "C$_{1-6}$ ethyl," with -- C$_{1-6}$ alkyl, --.

Col. 94, line 28 (claim 8), replace "is 0, 1, 2 or 3" with -- j is 0, 1, 2 or 3 --.

Col. 94, line 43 (claim 9), replace "ON," with -- CN, --.

Col. 94 line 49 (claim 9), replace "C$_{1-4}$haloalkoxy" with -- C$_{1-4}$ haloalkoxy --.

Col. 94, line 63 (claim 9), replace "ON," with -- CN, --.

Col. 94, line 66-67 (claim 9), replace "1, 2, 3, 4 or 5-W-X-Y-Z;"
with -- 1, 2, 3, 4 or 5 –W-X-Y-Z; --.

Col. 95, line 5 (claim 9), replace

"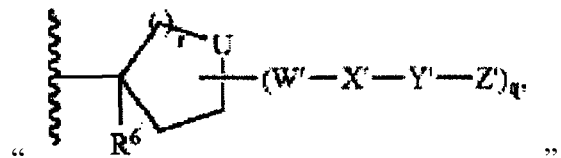"

with

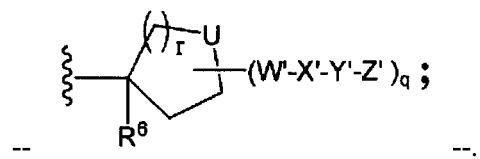
-- --.

Col. 95, line 57-58 (claim 9), replace "1, 2 or 3-W''-X''-Y''-Z'';"
with -- 1, 2 or 3 –W''-X''-Y''-Z''; --.

Col. 95, line 62-63 (claim 9), replace "1, 2 or 3-W''-X''-Y''-Z'';"
with -- 1, 2 or 3 –W''-X''-Y''-Z''; --.

Col. 96, line 41 (claim 12), replace "orC$_{1-6}$ haloalkyl" with -- or C$_{1-6}$ haloalkyl --.

Col. 99, line 36-37 (claim 23), replace

"2-{([4-(cyanomethoxy)phenyl]thio}-N-cyclohexyl-2-methylpropanamide;" with
-- 2-{[4-(cyanomethoxy)phenyl]thio}-N-cyclohexyl-2-methylpropanamide; --.
Col. 100, line 23 (claim 23), replace "pharmaceutically" with -- and pharmaceutically --.
Col. 100, line 40 (claim 28), replace
"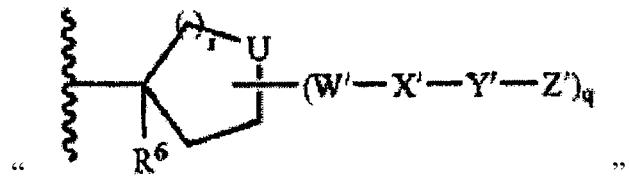"
with
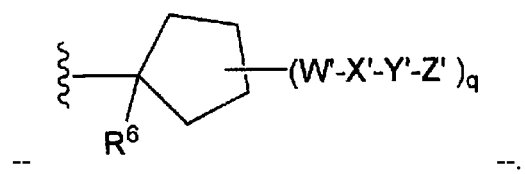
--          --.